(12) United States Patent
Thuring et al.

(10) Patent No.: US 8,143,419 B2
(45) Date of Patent: Mar. 27, 2012

(54) TRISUBSTITUTED 1,2,4-TRIAZOLES

(75) Inventors: Johannes Wilhelmus John F. Thuring, Antwerp (BE); Gregor James MacDonald, Zoersel (BE); Anne Simone Josephine Lesage, Halle-Zoersel (BE); Wei Zhuang, Antwerp (BE); Marcel Frans Leopold De Bruyn, Wortel (BE); Frans Alfons Maria Van Den Keybus, Essen (BE); Yves Emiel Maria Van Roosbroeck, Heist-op-den-Berg (BE); Theodorus Dinklo, Beerse (BE); James Edward Stewart Duffy, Cambridgehire (GB)

(73) Assignee: Janssen Pharmaceutica N. V., Beerse (BE)

( * ) Notice: Subject to any disclaimer, the term of this patent is extended or adjusted under 35 U.S.C. 154(b) by 75 days.

(21) Appl. No.: 12/297,059

(22) PCT Filed: Apr. 19, 2007

(86) PCT No.: PCT/EP2007/053829
§ 371 (c)(1),
(2), (4) Date: Oct. 14, 2008

(87) PCT Pub. No.: WO2007/118903
PCT Pub. Date: Oct. 25, 2007

(65) Prior Publication Data
US 2009/0253691 A1    Oct. 8, 2009

(30) Foreign Application Priority Data
Apr. 19, 2006 (EP) .................................... 06112754

(51) Int. Cl.
*A61K 31/41* (2006.01)
*C07D 249/08* (2006.01)

(52) U.S. Cl. ..................................... 548/264.8; 514/383
(58) Field of Classification Search ............... 548/264.8; 514/383, 338; 546/283.7
See application file for complete search history.

(56) References Cited

FOREIGN PATENT DOCUMENTS

| EP | 0248523 B1 | 10/1991 |
|---|---|---|
| EP | 1 070 708 A1 | 1/2001 |
| EP | 1044970 B1 | 1/2003 |
| WO | 01/44207 A2 | 6/2001 |
| WO | 03/094831 A3 | 11/2003 |
| WO | WO 2005/012263 A1 | 2/2005 |
| WO | 2005/051917 A1 | 6/2005 |
| WO | 2006/064375 A2 | 6/2005 |
| WO | 2007/031440 A2 | 3/2007 |
| WO | 2007/118903 A1 | 10/2007 |

OTHER PUBLICATIONS

Hcaplus Abstract 1974:437516, "Synthesis of triazolones and C-aminotriazoles by the thermal condensation of carbamidoamidrazones", 1974, Gol'din et. al.*
West, Anthony R., Solid State Chemistry and its Applications, Wiley, New York, 1988, pp. 358 & 365.*
Lin et. al., "Recent developments in neuronal nicotinic acetycholine receptor modulators", 1998, 8 (8), pp. 991-1015.*
Silverman, R. "The Organic Chemistry of Drug Design and Drug Action," 2004, Elsevier, pp. 29-32.*
Makara et al., "Solid-Phase Synthesis of 3-Alkylamino-1,2,4-triazoles", Organic Letters, vol. 4, No. 10, pp. 1751-1754 (2002).
Chen et al., "1-Alkyl-3-amino-5-aryl-1H-[1,2,4]triazoles: Novel Synthesis Via Cyclization of N-Acyl-S-methylisothioureas with Alkylhydrazines and Their Potent Corticotropic-Releasing Factor-1 (CRF₁) Receptor Antagonist Activities", Bioorganic & Medicinal Chemistry Letters, vol. 11, pp. 3165-3168 (2001).
International Search Report dated Jul. 27, 2007 for related International Application No. PCT/EP2007/053829.
Chen, et al., "1-Alkyl-3-amino-5-aryl-1H-[1,2,4]triazoles: Novel Synthesis via Cyclization of N-acyl-S-methyliosothiouzeas with Alkylhydrazines and Their Potent Corticotropin-Releasing Factor-1 (CFR1) Receptor Antagonist Activities", Bioorganic & Medicinal Chemistry Letters 11, pp. 3165-3168, (2001).
Makara, et al, "Solid-Phase Synthesis of 3-Alkylamino-1,2,4-triazoles", Organic Letters, vol. 4, No. 10, pp. 1751-1754, (2002).
Muccioli, et al., "Latest Advances in Cannadinoid Receptor Antagonists and Inverse Agonists", Expert Opinion on Therapeutic Patents, vol. 16, No. 10, pp 1405-1423, (2006).
Vippagunta, et al., "Crystalline Solids", Advanced Drug Delivery Reviews, vol. 48, pp. 3-26, (2001).
Silverman, R. The Organic Chemistry of Drug Design and Drug Action, Elsevier, pp. 29-32, (2004).

* cited by examiner

*Primary Examiner* — Janet Andres
*Assistant Examiner* — Heidi Reese
(74) *Attorney, Agent, or Firm* — Andrea Jo Kamage

(57) ABSTRACT

The present invention relates to 3-aniline-5-aryl triazole derivatives and analogues or pharmaceutically acceptable salts thereof, processes for preparing them, pharmaceutical compositions containing them and their use in therapy, according to Formula (I).

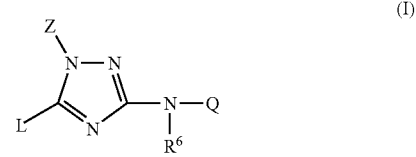

The invention particularly relates to positive allosteric modulators of nicotinic acetylcholine receptors, such positive allosteric modulator having the capability to increase the efficacy of nicotinic receptor agonists.

11 Claims, No Drawings

TRISUBSTITUTED 1,2,4-TRIAZOLES

CROSS REFERENCE TO RELATED APPLICATIONS

This application is a national stage application of Patent Application No. PCT/EP2007/053829, filed Apr. 19, 2007, which application claims priority from EPO Patent Application No. 06112754.4, filed Apr. 19, 2006, both of which are hereby incorporated by reference in their entirety.

The present invention relates to 3-aniline-5-aryl triazole derivatives and analogues or pharmaceutically acceptable salts thereof, processes for preparing them, pharmaceutical compositions containing them and their use in therapy. The invention particularly relates to positive allosteric modulators of nicotinic acetylcholine receptors, such positive allosteric modulators having the capability to increase the efficacy of nicotinic receptor agonists.

BACKGROUND PRIOR ART

EP 1044970 describes 3-alkylamino-1,2,4-triazoles as neuropeptide Y receptor ligands. The paper by Makara G. M., et al. (Organic Letters (2002) Vol. 4 (10); 1751-1754) describes the solid-phase synthesis of 3-alkylamino-1,2,4-triazoles and exemplifies the unsuccessful synthesis of N-(4-methoxyphenyl)-1-methyl-5(4-methylphenyl)-1H-1,2,4-triazol-3-amine [CAS No: 433710-55-5] and is silent about potential therapeutic applications of this compound, in particular about its use as a positive allosteric modulator of the α7 nicotinic acetylcholine receptor.

Chen Chen et al., in Bioorganic & Medicinal Chemistry Letters 11 (2001) 3165-3168 describes the synthesis of 1-alkyl-3-amino-5-aryl-1H-[1,2,4]triazoles, in particular N-(2-methoxyphenyl)-1-methyl-5-(2,4-dichlorophenyl)-1H-1,2,4-triazol-3-amine, and their use as corticotropin-releasing factor-1 (CRF1) antagonist.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors has been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors. and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit or memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and of particular note at the α7-nicotinic receptor, desensitization limits the duration of action of an applied agonist.

DESCRIPTION OF THE INVENTION

We have surprisingly found that certain novel compounds can increase the efficacy of agonists at nicotinic acetylcholine receptors (nAChR). Compounds having this type of action (hereinafter referred to as "positive allosteric modulators") are likely to be particularly useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur at prolonged application of agonists.

Positive nAChR modulators of the present invention useful for treatment or prophylaxis of psychotic disorders, intellectual impairment disorders or diseases or conditions in which modulation of the α7 nicotinic receptor is beneficial.

The present invention concerns 3-aniline-5-aryl triazole derivatives having positive allosteric modulator properties, in particular increasing the efficacy of agonists at the α7 nicotinic receptor. The invention further relates to methods for their preparation and pharmaceutical compositions comprising them. The invention also relates to the use of 3-aniline-5-aryl triazole derivatives for the manufacture of a medicament for the treatment or prophylaxis of psychotic disorders, intellectual impairment disorders or diseases or conditions in which modulation of the α7 nicotinic receptor is beneficial.

The compounds of the present invention differ structurally from the prior art compounds and pharmacologically by their activity as positive allosteric modulators of the α7 nicotinic acetylcholine receptor.

The present invention relates to a compound according to formula (I)

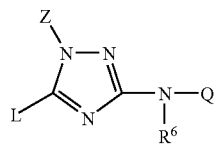

including all stereochemically isomeric forms thereof, wherein

Z is $C_{1-6}$alkyl or $C_{1-6}$alkyl substituted with one or more substituents independently selected from the group consisting of hydroxy, cyano, $C_{1-6}$alkyl-O—, $R^1R^2N$—C(=O)—, $R^7$—O—C(=O)—$NR^8$—, $R^{10}$—O—C(=O)—, $R^3$—C(=O)—$NR^4$—, HO—N—C(=NH)—, halo, oxo, polyhalo$C_{1-6}$alkyl and Het;

Q is phenyl, pyridinyl, indolinyl, benzodioxolyl, 1,4-benzodioxanyl, benzofuranyl, 2,3-dihydrobenzofuranyl, isoxazolyl, oxazolyl, thiazolyl, isothiazolyl, pyrimidinyl, or pyridazinyl, wherein each radical is optionally substituted with one, two or three substituents each independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, Het, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{11}$— and $R^{12}R^{13}N$—C(=O)—;

L is $C_{1-6}$alkyl optionally substituted with one or where possible two or more substituents each independently selected from the group consisting of halo, $C_{1-6}$alkyl-O—, $C_{1-6}$alkylthio, $C_{1-6}$alkyl-O—C(=O)—, polyhalo$C_{1-6}$alkyl and polyhalo$C_{1-6}$alkyl-O—; or is $C_{3-6}$cycloalkyl, phenyl, pyrimidinyl, pyridinyl, pyrimidazolyl, pyridazinyl, tetrahydropyranyl, imidazothiazolyl, benzodioxolyl, indolinyl, isoindolinyl, benzofuranyl, quinolinyl, isoquinolinyl, benzoxazolyl, 5,6,7,8,-tetrahydroquinolinyl, 5,6,7,8,-tetrahydroisoquinolinyl, 2,3-dihydropyrrolopyridinyl, furopyridinyl, 2,3-dihydrobenzofuranyl, benzodioxanyl, dihydrofuropyridinyl, 7-azaindolinyl, and 3,4-dihydro-2H-1,4-benzoxazinyl; wherein each of the aforementioned radicals is optionally substituted with one or two or more substituents, each substituent being independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, Het$^1$, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{14}$—, $R^{15}R^{16}N$—C(=O)—, morpholinyl, $CH_3O$—$C_{1-6}$alkyl-NH—, HO—$C_{1-6}$alkyl-NH—, benzyloxy, $C_{3-6}$cycloalkyl, $C_{3-6}$cycloalkyl-NH—, $C_{3-6}$cycloalkyl$C_{1-6}$alkyl-NH—, polyhalo$C_{1-6}$alkyl-C(=O)—$NR^{14}$, $C_{1-6}$alkyl-C(=O)—, and $C_{1-6}$alkyl-O—$C_{1-6}$alkyl-;

$R^1$ and $R^2$ each independently represent hydrogen, $C_{1-6}$alkyl, $C_{3-6}$cycloalkyl, $C_{1-4}$alkyl-O—$C_{1-6}$alkyl, Het$^2$, HO—$C_{1-6}$alkyl, polyhalo$C_{1-6}$alkyl, $C_{3-6}$cycloalkyl substituted with $C_{1-4}$alkyl, $C_{3-6}$cycloalkyl$C_{1-6}$alkyl, dimethylamino-$C_{1-4}$alkyl or 2-hydroxycyclopentan-1-yl;

or $R^1$ and $R^2$ taken together with the nitrogen atom to which they are attached form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano and $C_{1-6}$alkyl;

$R^3$ represents hydrogen, $C_{1-6}$alkyl, $C_{3-6}$cycloalkyl, Het$^3$ or $C_{1-6}$alkyl substituted with one or more substituents selected from the group consisting of hydroxy, cyano, $C_{1-4}$alkyl-O— and Het$^4$;

$R^4$ and $R^8$ each independently represent hydrogen, $C_{1-6}$alkyl, or $C_{3-6}$cycloalkyl; wherein each of these alkyl-radicals may be substituted with one or more substituents selected from the group consisting of hydroxy, cyano, and $C_{1-4}$alkyl-O—;

$R^6$ represents hydrogen, $C_{1-6}$alkyl, or where Q represents phenyl, $R^6$ may also be a $C_{2-6}$alkanediyl attached to said phenyl ring to form together with the nitrogen to which it is attached and said phenyl ring a fused bicyclic ring system containing 9 to 10 ring atoms such as indolinyl or tetrahydroquinolinyl, each optionally substituted with trifluoromethyl;

$R^7$ and $R^{10}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano, $C_{1-4}$alkyl-O—, Het$^4$ and $NH_2$—C($CH_3$)=N—;

$R^{11}$ and $R^{14}$ each independently represents hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—;

$R^{12}$ and $R^{13}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano or $C_{1-4}$alkyl-O—; or $R^{12}$ and $R^{13}$ taken together with the nitrogen atom to which they are attached may form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano, $C_{1-6}$alkyl or polyhalo$C_{1-6}$alkyl;

$R^{15}$ and $R^{16}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—; or $R^{15}$ and $R^{16}$ taken together with the nitrogen atom to which they are attached may form a heterocyclic radical selected from the group consisting of pyrrolidinyl, piperidinyl, piperazinyl, morpholinyl, thiomorpholinyl or pyrazolidinyl; wherein said heterocyclic radical is optionally substituted with 1, 2 or 3 substituents each independently selected from the group consisting of halo, hydroxy, amino, cyano, $C_{1-6}$alkyl and polyhalo$C_{1-6}$alkyl;

Het and Het$^1$ each independently represent piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

Het$^2$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl, pyrazolyl or tetrahydrofuranyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^3$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^4$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano or $C_{1-6}$alkyl;

an N-oxide, a pharmaceutically acceptable addition salt, a solvate, or a quaternary amine thereof, provided said compound is not N-(2-methoxyphenyl)-1-methyl-5-(2,4-dichlorophenyl)-1H-1,2,4-triazol-3-amine.

The present invention relates in particular to a compound according to formula (I)

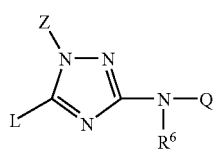

(I)

including all stereochemically isomeric forms thereof, wherein

Z is $C_{1-6}$alkyl or $C_{1-6}$alkyl substituted with one or more substituents independently selected from the group consisting of hydroxy, cyano, $C_{1-6}$alkyl-O—, $R^1R^2N$—C(=O)—, $R^7$—O—C(=O)—$NR^8$—, $R^{10}$—O—C(=O)— and $R^3$—C(=O)—$NR^4$—;

Q is phenyl, pyridinyl, indolinyl, benzodioxolyl, 1,4-benzodioxanyl, benzofuranyl, 2,3-dihydrobenzofuranyl, isoxazolyl, oxazolyl, thiazolyl, isothiazolyl, pyrimidinyl, or pyridazinyl; wherein each radical is optionally substituted with one, two or three substituents each independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, Het, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{11}$— and $R^{12}R^{13}N$—C(=O)—;

L is $C_{1-6}$alkyl optionally substituted with one or where possible two or more substituents each independently selected from the group consisting of halo, $C_{1-6}$alkyl-O—, $C_{1-6}$alkylthio, $C_{1-6}$alkyl-O—C(=O)—, polyhalo$C_{1-6}$alkyl and polyhalo$C_{1-6}$alkyl-O—; or is $C_{3-6}$cycloalkyl, phenyl, pyrimidinyl, pyridinyl, pyrimidazolyl, pyridazinyl, tetrahydropyranyl, imidazothiazolyl, benzodioxolyl, indolinyl, isoindolinyl, benzofuranyl, quinolinyl, isoquinolinyl, benzoxazolyl, 5,6,7,8,-tetrahydroquinolinyl, 5,6,7,8,-tetrahydroisoquinolinyl, 2,3-dihydropyrrolopyridinyl, furopyridinyl, or 2,3-dihydrobenzofuranyl; wherein each of the aforementioned radicals is optionally substituted with one or two or more substituents, each substituent being independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, $Het^1$, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{14}$— and $R^{15}R^{16}N$—C(=O)—;

$R^1$ and $R^2$ each independently represent hydrogen, $C_{1-6}$alkyl, $C_{3-6}$cycloalkyl, $C_{1-4}$alkyl-O—$C_{1-6}$alkyl or $Het^2$; or $R^1$ and $R^2$ taken together with the nitrogen atom to which they are attached form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano, $C_{1-6}$alkyl and polyhalo$C_{1-6}$alkyl;

$R^3$ represents hydrogen, $C_{1-6}$alkyl, $C_{3-6}$cycloalkyl, $Het^3$ or $C_{1-6}$alkyl substituted with one or more substituents selected from the group consisting of hydroxy, cyano, $C_{1-4}$alkyl-O— and $Het^4$;

$R^4$ and $R^8$ each independently represent hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—;

$R^6$ represents hydrogen, $C_{1-6}$alkyl, or where Q represents phenyl, $R^6$ may also be a $C_{2-6}$alkanediyl attached to said phenyl ring to form together with the nitrogen to which it is attached and said phenyl ring a fused bicyclic ring system containing 9 to 10 ring atoms such as indolinyl or tetrahydroquinolinyl;

$R^7$ and $R^{10}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano, $C_{1-4}$alkyl-O— and $Het^4$;

$R^{11}$ and $R^{14}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—;

$R^{12}$ and $R^{13}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano or $C_{1-4}$alkyl-O—; or $R^{12}$ and $R^{13}$ taken together with the nitrogen atom to which they are attached may form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano, $C_{1-6}$alkyl or polyhalo$C_{1-6}$alkyl;

$R^{15}$ and $R^{16}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—; or $R^{15}$ and $R^{16}$ taken together with the nitrogen atom to which they are attached may form a heterocyclic radical selected from the group consisting of pyrrolidinyl, piperidinyl, piperazinyl, morpholinyl, thiomorpholinyl or pyrazolidinyl; wherein said heterocyclic radical is optionally substituted with 1, 2 or 3 substituents each independently selected from the group consisting of halo, hydroxy, amino, cyano, $C_{1-6}$alkyl and polyhalo$C_{1-6}$alkyl;

Het and $Het^1$ each independently represent piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^2$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^3$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^4$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano or $C_{1-6}$alkyl;

an N-oxide, a pharmaceutically acceptable addition salt, a solvate, or a quaternary amine thereof;

provided that said compound is not
N-(2-methoxyphenyl)-1-methyl-5-(2,4-dichlorophenyl)-1H-1,2,4-triazol-3-amine, and
N-(4-methoxyphenyl)-1-methyl-5-(4-methylphenyl)-1H-1,2,4-triazol-3-amine.

A particular compound according to the present invention is a compound according to formula (I)

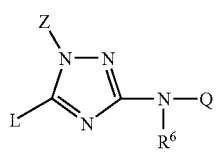

(I)

including all stereochemically isomeric forms thereof, wherein

Z is $C_{1-6}$alkyl or $C_{1-6}$alkyl substituted with one or more substituents independently selected from the group consisting of hydroxy, cyano, $C_{1-6}$alkyl-O—, $R^1R^2N$—C(=O)—, $R^7$—O—C(=O)—$NR^8$—, $R^{10}$—O—C(=O)—, $R^3$—C(=O)—$NR^4$—, HO—N=C(=NH)—, halo, oxo, polyhalo$C_{1-6}$alkyl and Het;

Q is phenyl, pyridinyl, benzodioxolyl, wherein each radical is optionally substituted with one, two or three substituents each independently selected from the group consisting of halo, cyano, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino;

L is phenyl, pyridinyl, benzodioxolyl, indolinyl, quinolinyl, 2,3-dihydropyrrolopyridinyl, furopyridinyl, benzodioxanyl, dihydrofuropyridinyl, 7-azaindolinyl, 3,4-dihydro-2H-1,4-benzoxazinyl; wherein each radical is optionally substituted with one or two or more substituents, each substituent being independently selected from the group consisting of halo, cyano, $C_{1-6}$alkyl, $C_{1-6}$alkyl-O—, polyhalo$C_{1-6}$alkyl, HO—$C_{1-6}$alkyl-, polyhalo$C_{1-6}$alkyl-O—, amino-$C_{1-6}$alkyl-, mono- or di($C_{1-6}$alkyl)amino, $R^{15}R^{16}N$—C(=O)—, morpholinyl, $CH_3O$—$C_{1-6}$alkyl-NH—, HO—$C_{1-6}$alkyl-NH—, benzyloxy, $C_{3-6}$cycloalkyl, $C_{3-6}$cycloalkyl-NH—, $C_{3-6}$cycloalkyl-$C_{1-6}$alkyl-NH—, polyhalo$C_{1-6}$alkyl-C(=O)—$NR^{14}$—, $C_{1-6}$alkyl-C(=O)—, and $C_{1-6}$alkyl-O—$C_{1-6}$alkyl-;

$R^1$ and $R^2$ each independently represent hydrogen, $C_{1-6}$alkyl, $C_{3-6}$cycloalkyl, $C_{1-4}$alkyl-O—$C_{1-6}$alkyl, $Het^2$, HO—$C_{1-6}$alkyl, polyhalo$C_{1-6}$alkyl, $C_{3-6}$cycloalkyl substituted with $C_{1-4}$alkyl, $C_{3-6}$cycloalkyl$C_{1-6}$alkyl, dimethylamino-$C_{1-4}$alkyl
or 2-hydroxycyclopentan-1-yl; or $R^1$ and $R^2$ taken together with the nitrogen atom to which they are attached form a heterocyclic radical selected from the group consisting of pyrrolidinyl, and morpholinyl;

$R^3$ represents hydrogen, $C_{1-6}$alkyl, $C_{3-6}$cycloalkyl, or $Het^3$;

$R^4$ and $R^8$ each independently represent hydrogen or $C_{1-6}$alkyl;

$R^6$ represents hydrogen, or where Q represents phenyl, $R^6$ may also be a $C_{2-6}$alkanediyl attached to said phenyl ring to form together with the nitrogen to which it is attached and said phenyl ring indolinyl substituted with trifluoromethyl;

$R^7$ and $R^{10}$ each independently represent $C_{1-6}$alkyl or $C_{3-6}$cycloalkyl;

$R^{11}$ and $R^{14}$ each independently represents hydrogen or $C_{1-6}$alkyl;

$R^{15}$ and $R^{16}$ each independently represent hydrogen or $C_{1-6}$alkyl; or $R^{15}$ and $R^{16}$ taken together with the nitrogen atom to which they are attached may form pyrrolidinyl; Het and $Het^1$ each independently represent oxazolyl optionally substituted with $C_{1-6}$alkyl;

$Het^2$ represents tetrahydrofuranyl;

$Het^3$ represents oxazolyl;

an N-oxide, a pharmaceutically acceptable addition salt, a solvate, or a quaternary amine thereof.

More particular a compounds according to the present invention is a compounds according to formula

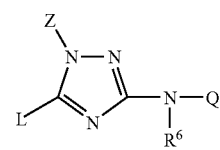

(I)

including all stereochemically isomeric forms thereof, wherein

Z is $C_{1-6}$alkyl substituted with hydroxy, $R^1R^2N$—C(=O)—, $R^3$—C(=O)—$NR^4$—;

Q is phenyl, pyridinyl, or benzodioxolyl; wherein each radical is optionally substituted with one, two or three substituents each independently selected from the group consisting of halo, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino;

L is phenyl, pyridinyl, benzodioxolyl, indolinyl, 2,3-dihydropyrrolopyridinyl, furopyridinyl, benzodioxanyl, dihydrofuropyridinyl, 7-azaindolinyl, or 3,4-dihydro-2H-1,4-benzoxazinyl; wherein each radical is optionally substituted with one or two or more substituents, each substituent being independently selected from the group consisting of halo, $C_{1-6}$alkyl, $C_{1-6}$alkyl-O—, HO—$C_{1-6}$alkyl-, mono- or di($C_{1-6}$alkyl)amino, $C_{3-6}$cycloalkyl, $C_{3-6}$cycloalkyl-NH—, $C_{3-6}$cycloalkyl-$C_{1-6}$alkyl-NH—, and $C_{1-6}$alkyl-O—$C_{1-6}$alkyl-;

$R^1$ and $R^2$ each independently represent hydrogen, $C_{1-6}$alkyl, or $C_{3-6}$cycloalkyl;

$R^3$ represents $C_{1-6}$alkyl;

$R^4$ represents hydrogen or $C_{1-6}$alkyl;

$R^6$ represents hydrogen;

an N-oxide, a pharmaceutically acceptable addition salt, a solvate, or a quaternary amine thereof.

Still a more particular compound according to the present invention is a compound according to formula (I)

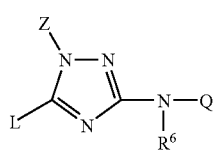

(I)

including all stereochemically isomeric forms thereof, wherein

Z is hydroxy$C_{2-3}$alkyl, or $R^1R^2N$—C(=O)—$C_{1-3}$alkyl;

Q is phenyl, or pyridinyl; wherein each radical is optionally substituted with one, two or three substituents each independently selected from the group consisting of halo, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino, or 2,2-difluoro-1,3-benzodioxol-5-yl;

L is phenyl, pyridinyl, indolinyl, 2,3-dihydropyrrolopyridinyl, benzodioxanyl, dihydrofuropyridinyl, 7-azaindolinyl, or 3,4-dihydro-2H-1,4-benzoxazinyl; wherein each radical is optionally substituted with one or two or more substituents, each substituent being independently selected from the group consisting of fluoro, chloro, $C_{1-2}$alkyl, $C_{1-2}$alkyl-O—, mono- or di($C_{1-2}$alkyl)amino, cyclopropyl, cyclopropyl-NH—, cyclopropylmethyl-NH—, and methyl-O-methyl-;

$R^1$ and $R^2$ each independently represent hydrogen, $C_{1-2}$alkyl, or $C_{3-5}$cycloalkyl;

$R^6$ represents hydrogen;

an N-oxide, a pharmaceutically acceptable addition salt, a solvate, or a quaternary amine thereof.

According to a particular embodiment of the invention, Z is selected from the group of hydroxyethyl; 2-hydroxypropyl; isopropylmethyl-NH—C(=O)—; methyl-NH—C(=O)-methyl; ethyl-NH—C(=O)-methyl; dimethylamino-C(=O)-ethyl-; pyrrolidinyl-C(=O)-ethyl-; isopropylamino-C(=O)-methyl-; and isoxazolecarboxamide-propyl wherein said isoxazole ring is optionally substituted with methyl According to another particular embodiment of the invention, Q is 2,2-difluoro-1,3-benzodioxol-5-yl.

According to another particular embodiment of the invention, L is a selected from the group consisting of phenyl, pyridinyl, or 1,4-benzodioxanyl; wherein said L is optionally substituted with one or more methyl or ethylamino substituents. In particular L is selected from 1,4-benzodioxanyl and pyridinyl; all of the aforementioned radicals, more in particular 4-pyridinyl, are substituted with one methyl or one ethylamino substituent.

Exemplary compounds according to the present invention are (S)-5-[2-(ethylamino)-4-pyridinyl]-α-methyl-3-[(3,4,5-trifluorophenyl)amino]-1H-1,2,4-triazole-1-ethanol, 3-[(2,2-difluoro-1,3-benzodioxol-5-yl)amino]-N,N-dimethyl-5-(4-pyridinyl)-1H-1,2,4-triazole-1-propanamide, 3-[(2,2-difluoro-1,3-benzodioxol-5-yl)amino]-N-ethyl-5-(2-methyl-4-pyridinyl)-1H-1,2,4-triazole-1-acetamide, 3-[(2,2-difluoro-1,3-benzodioxol-5-yl)amino]-N,N-dimethyl-5-(2-methyl-4-pyridinyl)-1H-1,2,4-triazole-1-propanamide, N-(cyclopropylmethyl)-3-[(2,2-difluoro-1,3-benzodioxol-5-yl)amino]-5-(2-methyl-4-pyridinyl)-1H-1,2,4-triazole-1-acetamide, including all stereochemically isomeric forms thereof, an N-oxide, a pharmaceutically acceptable addition salt, a solvate, or a quaternary amine thereof.

Other exemplary compounds according to the present invention are 5-(2,3-dihydro-1,4-benzodioxin-6-yl)-N-methyl-3-[[3-(trifluoromethyl)phenyl]-amino]-1H-1,2,4-triazole-1-acetamide, 5-(2,3-dihydro-1,4-benzodioxin-6-yl)-N-(1-methylethyl)-3-[[3-(trifluoromethyl)phenyl]amino]-1H-1,2,4-triazole-1-acetamide, 5-(4-pyridinyl)-3-[[3-(trifluoromethyl)phenyl]amino]-1H-1,2,4-triazole-1-ethanol, 5-(2,3-dihydro-1,4-benzodioxin-6-yl)-3-[[3-(trifluoromethyl)phenyl]amino]-1H-1,2,4-triazole-1-ethanol, 5-(2-chloro-4-pyridinyl)-3-[[3-(trifluoromethyl)phenyl]amino]-1H-1,2,4-triazole-1-ethanol, N,N-dimethyl-5-(4-pyridinyl)-3-[[3-(trifluoromethyl)phenyl]amino]-1H-1,2,4-triazole-1-propanamide, 5-(2,3-dihydro-1,4-benzodioxin-6-yl)-N,N-dimethyl-3-[[3-(trifluoromethyl)phenyl]-amino]-1H-1,2,4-triazole-1-propanamide, 5-methyl-N-[3-[5-(4-pyridinyl)-3-[[3-(trifluoromethyl)phenyl]amino]-1H-1,2,4-triazol-1-yl]propyl]-3-isoxazolecarboxamide, including all stereochemically isomeric forms thereof, an N-oxide, a pharmaceutically acceptable addition salt, a solvate, or a quaternary amine thereof.

As used hereinabove or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{3-6}$cycloalkyl is generic to cyclopropyl, cyclobutyl, cyclopentyl and cyclohexyl.

The L or Q radical as described above for the compounds according to formula (I) may be attached to the remainder of the molecule according to formula (I) through any ring carbon or heteroatom as appropriate. For example, when L is pyridinyl, it may be 2-pyridinyl, 3-pyridinyl or 4-pyridinyl.

Lines drawn into ring systems indicate that the bond may be attached to any suitable ring atom. When the ring system is a bicyclic ring system, the bond may be attached to any suitable ring atom of either of the two rings.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, for example methyl with one or more fluoro atoms, for example, difluoromethyl or trifluoromethyl, 1,1-difluoro-ethyl and the like. In case more than one halogen atoms are attached to an alkyl group within the definition of polyhalo$C_{1-4}$alkyl or polyhalo$C_{1-6}$alkyl, they may be the same or different.

The heterocycles mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl; benzodioxanyl includes 1,4 and 1,3 benzodioxanyl; tetrahydroquinolinyl includes 1,2,3,4-tetrahydroquinolinyl and 5,6,7,8-tetrahydroquinolinyl.

When any variable occurs more than one time in any constituent, each definition is independent.

It will be appreciated that some of the compounds according to formula (I) and their N-oxides, addition salts, solvates, quaternary amines and stereochemically isomeric forms thereof may contain one or more centers of chirality and exist as stereochemically isomeric forms.

The term "stereochemically isomeric forms" as used hereinbefore or hereinafter defines all the possible stereoisomeric forms which the compounds according to formula (I) and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds according to formula (I) are obviously intended to be embraced within the scope of this invention.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds according to formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvates refers to hydrates and alcoholates which the compounds according to formula (I) as well as the salts thereof, may form.

The term "quaternary amine" as used hereinbefore defines the quaternary ammonium salts which the compounds according to formula (I) are able to form by reaction between a basic nitrogen of a compound according to formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds according to formula (I) wherein one or several tertiary nitrogen atoms are oxidized to the so-called N-oxide.

Some of the compounds according to formula (I) may also exist in their tautomeric form. Such forms although not explicitly indicated in the above formula are intended to be included within the scope of the present invention.

Preparation of the Compounds

A compound according to the invention can generally be prepared by a succession of steps, each of which is known to the skilled person. In particular, the compounds in this patent application can be prepared according to one or more of the following preparation methods. In the following schemes, and unless otherwise indicated, all variables are used as defined in Formula (I).

Scheme 0

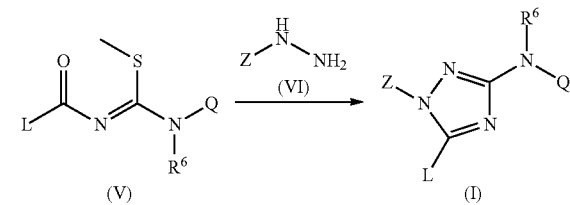

The compounds of this invention can be prepared by any of several standard synthetic processes commonly used by those skilled in the art of organic chemistry and are generally prepared according to Scheme 0 by transforming an N-acyl carbomimidothioic acid, methyl ester derivative of general formula (V) into the 1,2,4-triazoles of formula (I) using an appropriate hydrazine (VI) under art known conditions. This transformation is typically performed in a protic solvent, such as methanol or a higher alcohol and requires a temperature between room temperature and 150° C. In a particular embodiment the higher alcohol is tertiary butyl alcohol and the reaction temperature is between 70° and 120° C., most preferably 100° C. For those reactions wherein the hydrazine (VI) is used as an HCl salt, the addition of a stoichiometric amount of a base is preferred. Said base can be an inorganic base, such as potassium acetate or potassium carbonate, more preferably however, said base is a tertiary amine, such as diisopropyl ethyl amine or the like (scheme 0).

The common intermediate (V) in the synthesis of the trisubstituted triazoles of the present invention is typically prepared by a protocol that consists of 3 synthetic transformations (Scheme 1), starting from an acyl chloride of the general formula (II). The acid chloride (II) can be obtained by treatment of the carboxylic acid (VII) with an excess of oxalyl chloride, optionally in the presence of DMF as a catalyst, at elevated temperature, in particular at reflux temperature. Said transformation may also be effected in the presence of an organic solvent, such as dichloromethane or the like.

In a first step the acylating agent, such as an acyl chloride (II), a mixed or symmetric anhydride, an acyl fluoride and the like; is reacted with a monovalent cation thiocyanate (MNCS in scheme 1), such as for example potassium thiocyanate or ammonium thiocyanate to yield the corresponding acyl isothiocyanate. This reaction is usually performed using acetone as a solvent and at a temperature between 0° C. and 70° C., preferably at room temperature.

The intermediate acyl isothiocyanate is not isolated but treated in the same reaction medium with an appropriate amine (III) to yield the N-acyl thiourea of the general formula (IV). This transformation reaction is usually performed at a temperature between 0° C. and 70° C., preferably at room temperature.

In a final step, S-methylation of the N-acyl thiourea provides the N-acyl carbomimidothioic acid, methyl ester derivative of general formula (V). This final transformation requires the presence of a strong base, preferably a strong inorganic base, such as NaH and is to be performed in an aprotic solvent such as for example DMF, THF and the like, at a temperature ranging from −70° C. to room temperature, preferably 0° C.

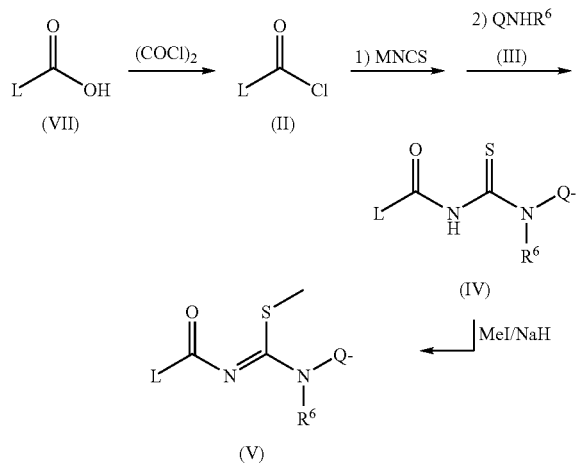

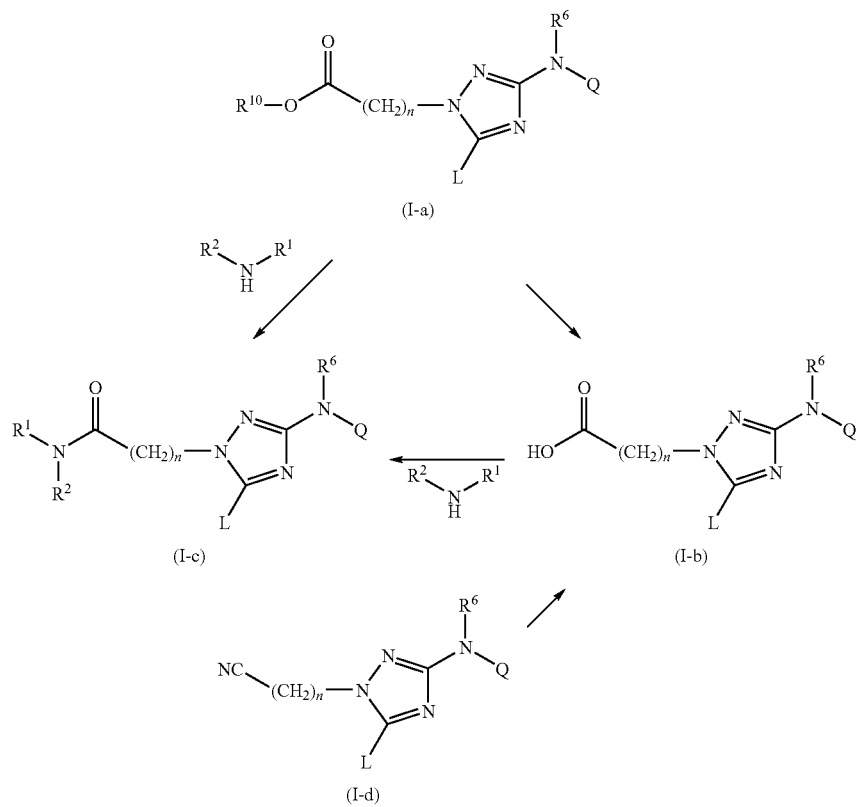

n = 1-6

The compound of general formula (I-a) can be hydrolyzed to a carboxylic acid with the general formula (I-b). This transformation can be affected by using an aqueous solution of strong acid, such as aqueous HCl, in the presence of a water miscible organic co-solvent, such as THF, methanol, or, most preferably 1,4-dioxane. A typical reaction temperature is between room temperature and 100° C., preferably 50° C. Alternatively, said hydrolysis can be effected through saponification, typically in the presence of a hydroxide base, such as LiOH or NaOH or the like, in a solvent mixture of water and a water miscible organic co-solvent, such as THF, methanol, 1,4-dioxane or mixtures thereof. Further conversion of the carboxylic acid into the amides of formula (I-c) is done using art known procedures, such as for example the treatment with a primary or secondary amine as defined hereinbefore in the presence of HBTU (O-benzotriazoleN,N,N',N'-tetramethyl uronium hexafluorophosphate) or EDCI. in an aprotic solvent like $CH_2Cl_2$, or more preferably in a polar aprotic solvent like DMF in the presence of an amine base additive, such as diisopropyl ethyl amine. Under certain circumstances the use of HOBt as an additive might be an advantage. In a particular embodiment of the present invention, when n=1 in a compound of the general formula I-a, the formation of an amide I-c can be achieved directly from I-a by reacting with an amine $R^1$—NH—$R^2$ in a protic solvent, such as ethanol or the like. The reaction can performed between 20° C. and 160° C., depending on the nature of the amine. A commonly used temperature is 80° C. (Scheme 2).

(VIII), such as for example a 3-isoxazolecarbonyl chloride, or an anhydride in the presence of an amine base, such as triethyl amine in a suitable solvent, such as for instance THF or $CH_2Cl_2$, provides the acylamines of formula (I-e) (Scheme 3).

Scheme 4

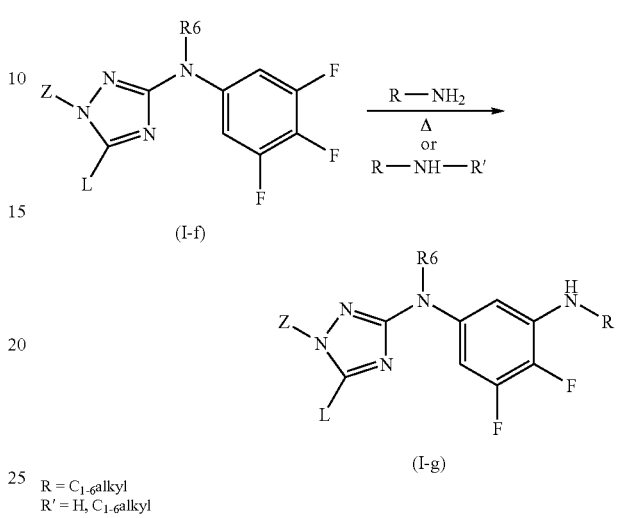

Scheme 3

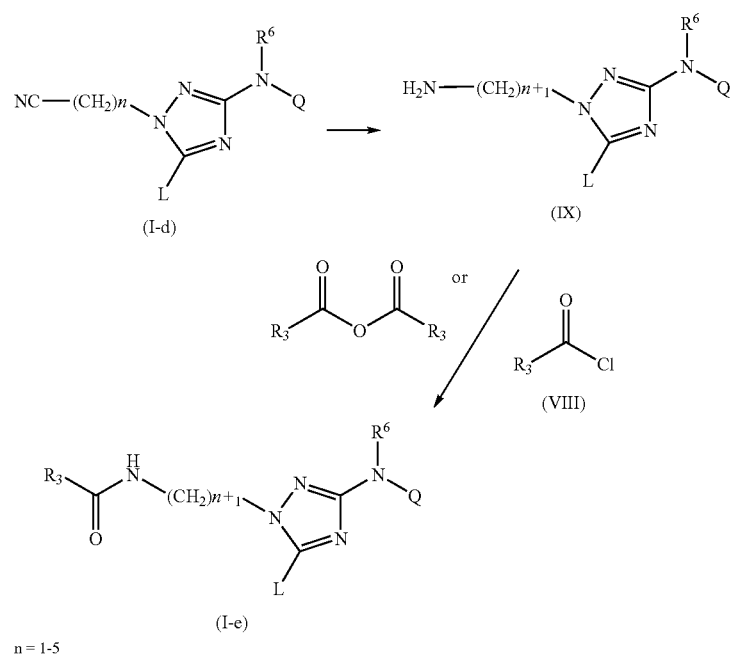

n = 1-5

Alternatively, when Z contains a cyano functionality, a nitrile of the general formula (I-d) can be reduced to a primary amine of the general formula (IX) using art known conditions, such as for example hydrogen gas in the presence of a suitable heterogenous catalyst, such as Raney nickel in a solvent system like methanol-ammonia and THF. Acylation of the amine of general formula (IX) with an acylating agent A nucleophilic aromatic displacement of a fluorine atom at the 3-position of the trifluorinated anilino triazole of the general formula (I-f) can be effected by dissolving (I-f) in an alcoholic solvent, such as ethanol or the like, in the presence of a primary or secondary alkyl amine R—$NH_2$ or R—NH—R' and heating at high temperatures, such as 160° C. in a microwave oven, yielding a final compound (I-g) (Scheme 4).

Scheme 5

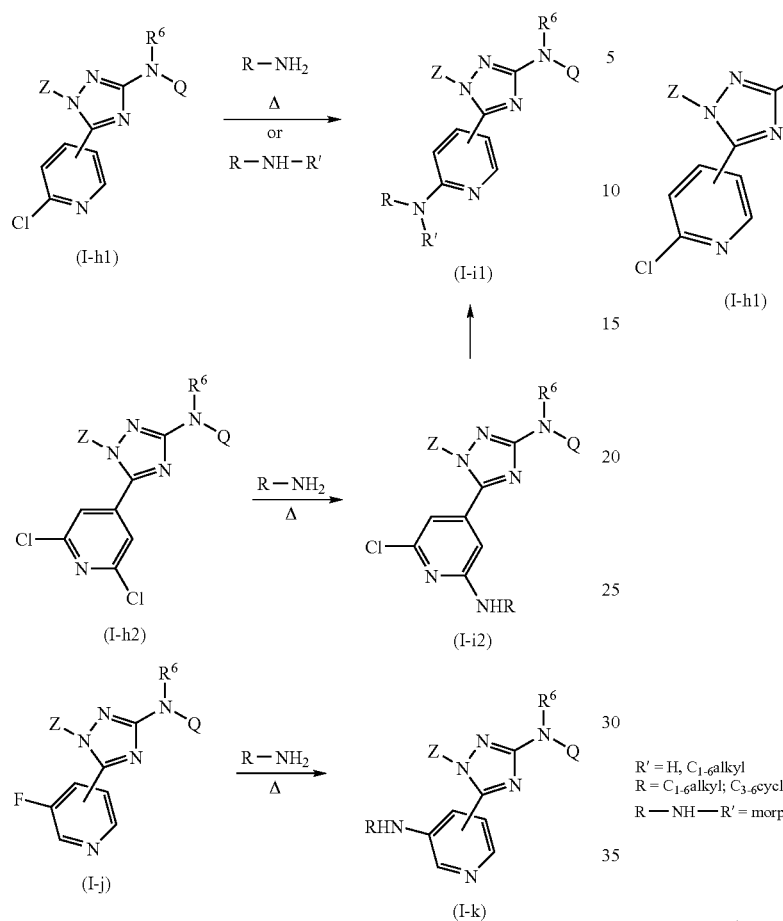

R' = H, C$_{1-6}$alkyl
R = C$_{1-6}$alkyl; C$_{3-6}$cycloalkyl
R—NH—R' = morpholino Scheme 5a

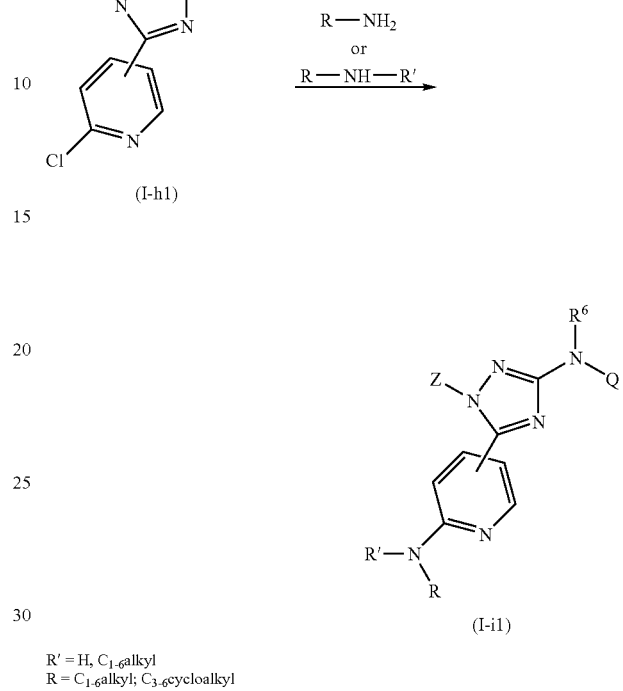

R' = H, C$_{1-6}$alkyl
R = C$_{1-6}$alkyl; C$_{3-6}$cycloalkyl
R—NH—R' = morpholino The synthesis of (cyclo)alkyl amino pyridines of the general formula (I-i1) or (I-i2) can be effected by treatment of the corresponding chloro pyridinyl precursor (I-h1) or (I-h2) with a primary (cyclo)alkyl amine R—NH$_2$ in an alcoholic solvent, such as ethanol or 1-butanol or the like, optionally in the presence of a co-solvent such as THF or the like, and heating at high temperatures, preferably in a range between 140° C. and 160° C. in a microwave oven, or at 160° C.-180° C. in an autoclave. Said transformation can be effected under milder conditions (lower temperature) by starting from the dichloro pyridinyl compound (I-h2), and is especially advantageous when the nucleophilicity of the alkyl amine is poor, such as in the case of cyclopropyl amine. The remaining chlorine atom can be removed catalytically, under a hydrogen atmosphere and using Pd/C as the catalyst, in the presence of an inorganic base, such as potassium acetate, or an amine base, such as triethyl amine, or the like (scheme 5). When the target compound is a 3-alkylamino pyridine of the general formula (I-k), the corresponding 3-fluoro pyridine of the general formula (I-j) can be advantageously chosen as the starting material. Said transformation requires the heating of (I-j) in the presence of an excess amount of alkyl amine R—NH$_2$ in an alcoholic solvent, such as ethanol at a temperature between 150° C. and 200° C., such as 180° C. (Scheme 5).

In an alternative embodiment of the present invention, (cyclo)alkyl amino pyridines of the general formula (I-i1) can be prepared from the corresponding chloro pyridinyl precursor (I-h1) and the appropriate primary or secondary alkyl amine R—NH$_2$ or R—NH—R' using transition metal catalysis. In particular, Buchwald-Hartwig conditions, using Pd$_2$(dba)$_3$ and a bidentate phosphine ligand, such as BINAP or the like, in the presence of a strong inorganic base, such as potassium or sodium tert butoxide, in THF as the solvent, can yield compounds of the general formula (I-i1). A typical reaction temperature is in the range between 100° C. and 130° C., which may be obtained by heating the reaction mixture in a microwave oven (Scheme 5a).

Scheme 6

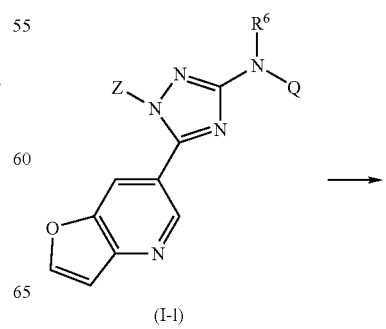

(I-l)

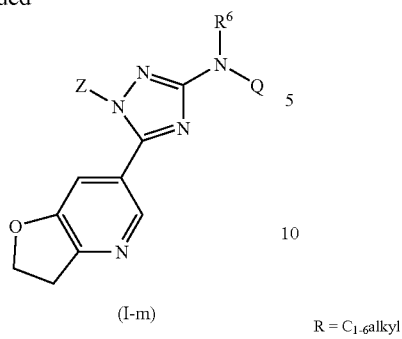

(I-m)

The pyrido dihydrofuran (I-m) can be obtained by catalytic hydrogenation of the pyrido furan precursor (I-l), using Pd/C as the catalyst in acetone as a solvent, or the like (Scheme 6).

Scheme 7

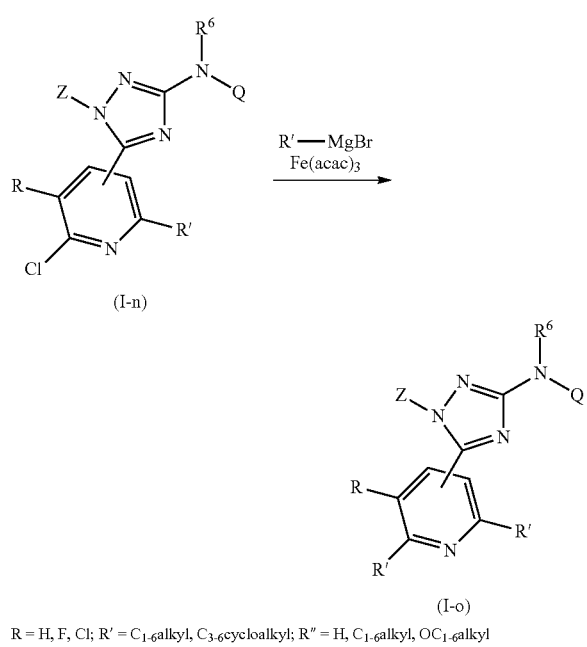

(I-o)

R = H, F, Cl; R' = $C_{1-6}$alkyl, $C_{3-6}$cycloalkyl; R'' = H, $C_{1-6}$alkyl, $OC_{1-6}$alkyl Alkyl or cycloalkyl substituted pyridines of the general formula (I-o), can optionally be prepared by treatment of the 2-chloro pyridinyl precursor (I-n) with an excess (3-15 equiv.) Grignard reagent R'—MgBr in the presence of a catalytic amount of $Fe(acac)_3$ in a solvent system consisting of 85% THF and 15% NMP. Said transformation can be performed in a temperature range 0° C. and 50° C., most preferably between 0° C. and 25° C. (Scheme 7).

Scheme 8

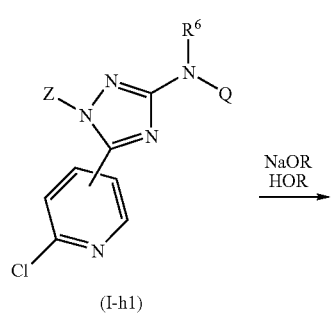

(I-h1)

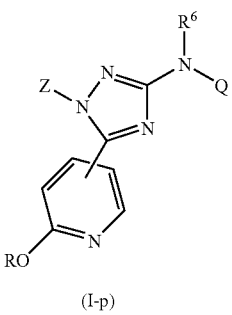

(I-p)

R = $C_{1-6}$alkyl

The synthesis of a 2-alkoxy derivatized pyridine (I-p) can be effected by treatment of the corresponding chloro pyridinyl precursor (I-h1) with a sodium alkoxide NaOR in an alcoholic solvent HOR, for example ethanol when R=Et, and heating at high temperatures, preferably at 100-130° C. in a pressure tube or microwave oven (Scheme 8). Alternatively, potassium tert butoxide can be advantageously used as a base.

Scheme 9

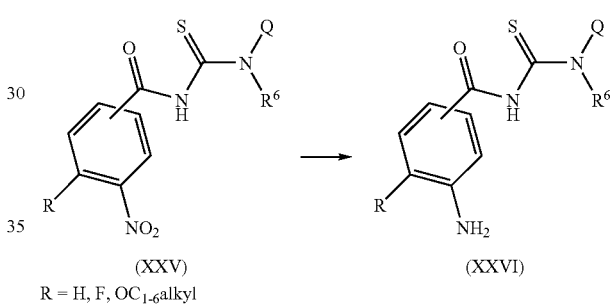

(XXV)　　(XXVI)

R = H, F, $OC_{1-6}$alkyl

The anilino acyl thiourea of the general formula (XXV) can be obtained by catalytic hydrogenation of the nitro phenyl precursor (XXVI), using Pd/C as the catalyst in the presence of thiophene and vanadium oxide in THF as the solvent, or the like (Scheme Scheme 10

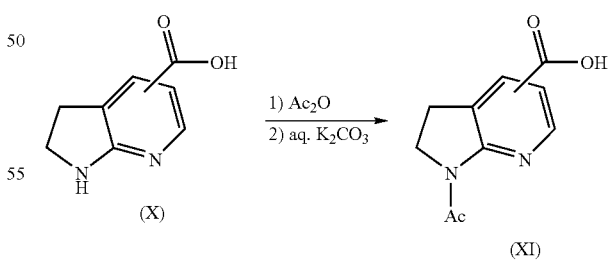

(X)　　(XI)

The acetyl protected aza indoline of the general formula (XI) can be prepared by heating the precursor of the general formula (X) in acetic anhydride, followed by a treatment with an inorganic base, such as potassium carbonate or the like, in an aqueous environment, preferably in the presence of an organic co-solvent, such as THF or the like, at a temperature between 25° C. and 80° C., preferably 50° C. (Scheme 10).

Scheme 11

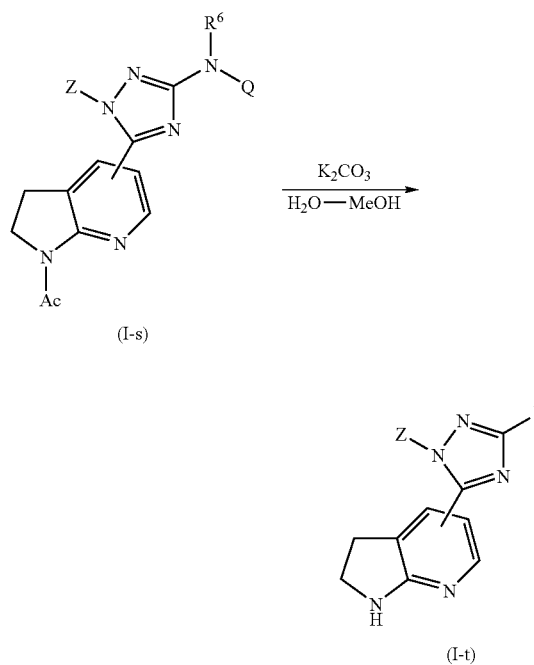

The aza indoline of the general formula (I-t) can be prepared by treating the acetyl protected precursor of the general formula (I-s) with an inorganic base, such as potassium carbonate or the like, in an aqueous environment, preferably in the presence of an organic co-solvent, such as methanol or the like, at a temperature between 25° C. and 80° C., preferably 70° C. (Scheme 11).

Scheme 12

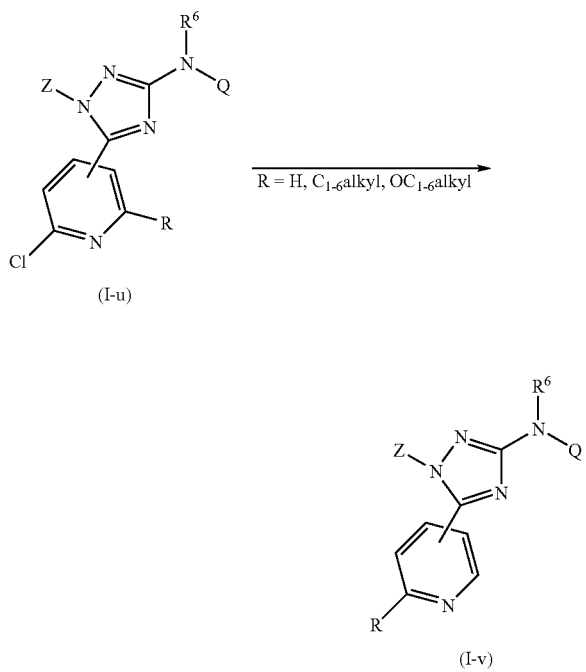

Scheme 12a

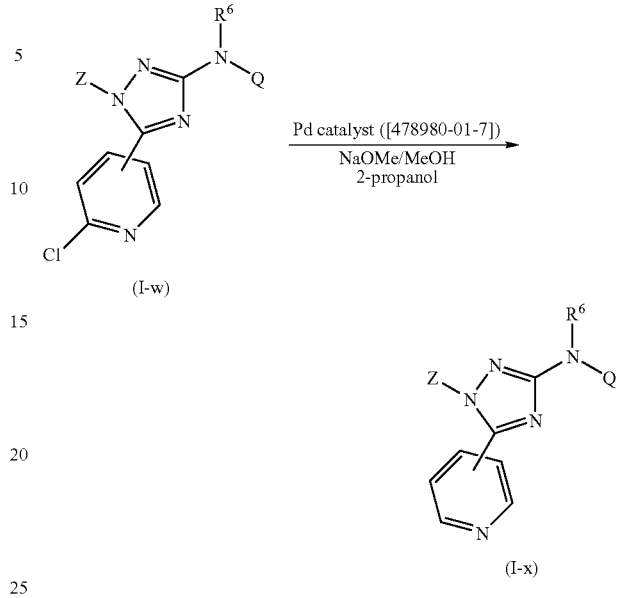

The pyrido triazole of the general formula (I-v) can be obtained by catalytic hydrogenation of the chloro pyridinyl precursor (I-u), using Pd/C as the catalyst in the presence of thiophene and an inorganic base, such as potassium acetate or the like, or an amine base, such as triethyl amine or the like, in a solvent like methanol or THF, or the like (Scheme 12). Alternatively, when either of the substituents Z and Q contain functionalities that are not compatible with catalytic hydrogenation conditions, the pyridine of the general formula (I-x) can be obtained from the chloro pyridine of the general formula (I-w), by treatment with a carbenoid catalysts, such as the Pd catalyst [1,3-bis[2,6-bis(I-methylethyl)phenyl]-2-imidazolidinylidene]chloro(η3-2-propenyl)-palladium ([478980-01-7]), in the presence of a strong base, such as sodium methoxide in a mixture of protic solvents, such as methanol and 2-propanol, or the like. Said reaction can be carried out at elevated temperature, such as 120° C. in a microwave oven (Scheme 12a).

Scheme 13

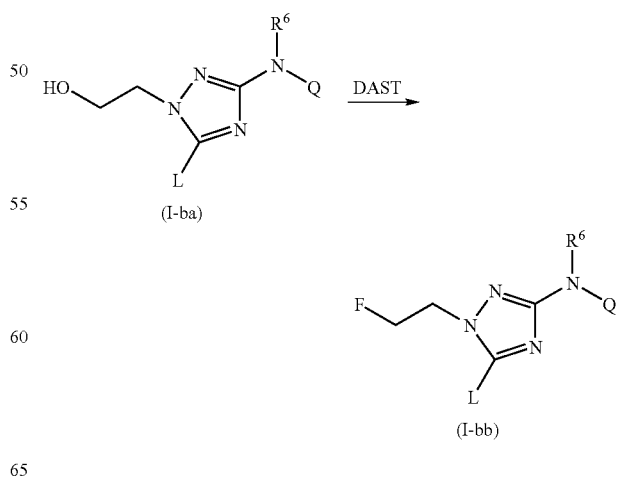

The fluoro alkyl compound of the general formula (I-bb) can be obtained from the corresponding hydroxyl compound (I-ba) by treatment with a fluorinating agent, such as DAST ((N-ethylethanaminato)trifluorosulfur), in a halogenated solvent, such as dichloromethane or the like, at a temperature between 0° C. and 25° C. (Scheme 13).

Scheme 14

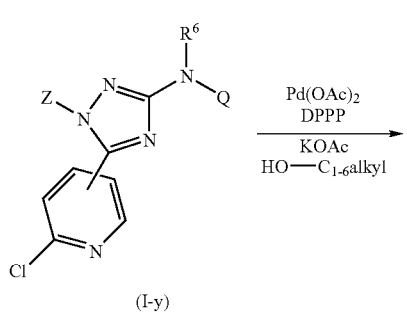

(I-y)

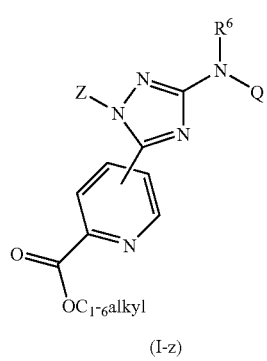

(I-z)

The alkyl carboxylate of the general formula (I-z) can be obtained from the chloro pyridinyl of the general formula (I-y) through a CO insertion reaction. Suitable conditions are the use of palladium acetate in the presence of a ligand, such as 1,3-bis(diphenylphosphino)propane (DPPP), under a CO atmosphere at a pressure of 50 atm., and an inorganic base such as potassium acetate or the like. The reaction further requires a polar solvent, such as THF and the like, and the corresponding alcoholic co-solvent. When $C_{1-6}$alkyl is methyl, the co-solvent should be methanol. The reaction is best performed at high temperature, such as 150° C. (Scheme 14).

Scheme 15

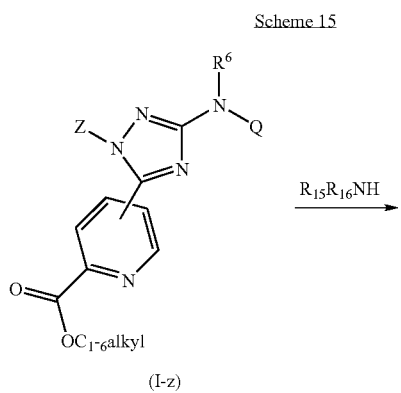

(I-z)

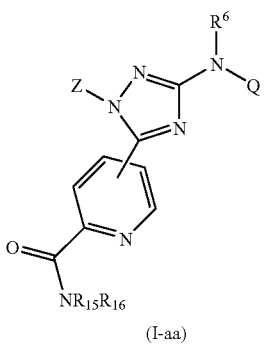

(I-aa)

The synthesis of the alkylamino carbonyl pyridines of the general formula (I-aa) can be effected by treatment of the corresponding alkoxy carbonyl pyridine precursor (I-z) with a (cyclo)alkyl amine $R_{15}R_{16}NH$ in a polar aprotic solvent, such as THF or the like, and heating at high temperatures, preferably in a range between 80° C. and 120° C. in a microwave oven (Scheme 15).

Scheme 16

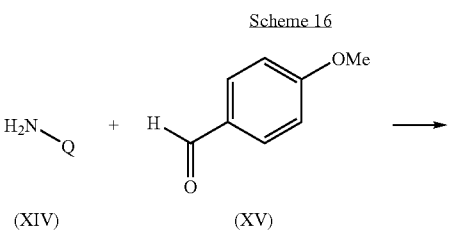

(XIV)   (XV)

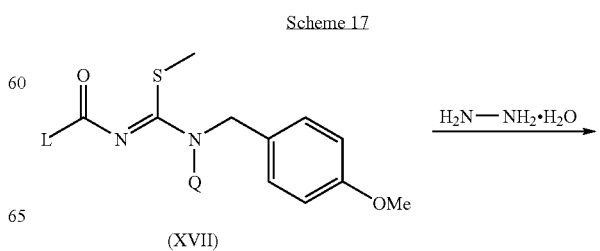

(XVI)

The para methoxybenzyl (PMB) protected secondary amine of the general formula (XVI) can be prepared by reductive amination using the aniline of the general formula (XIV) and para methoxybenzaldehyde (XV), in an hydrogen atmosphere and in the presence of a suitable catalyst, such as palladium on carbon. The reaction is most advantageously carried out in the presence of a thiophene solution and in a protic solvent, such as methanol or the like (Scheme 16).

Scheme 17

(XVII)

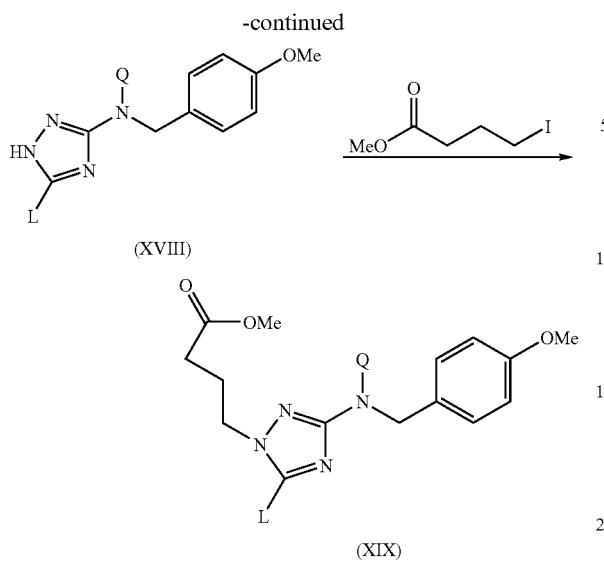

(XVIII)

(XIX)

The triazole of the general formula (XVIII) can be prepared by treating the precursor of the general formula (XVII) with hydrazine hydrate in a protic solvent, such as tert butanol, at a temperature between 70° C. and 100° C. The disubstituted triazole of the general formula (XVIII) can be alkylated by using a strong base, such as sodium hydride, in a polar aprotic solvent, such as THF or the like, and a suitable alkylating agent. For the preparation of the triazole with the general formula (XIX) the alkylating agent should be methyl 4-iodo butyrate, and the reaction temperature is 20° C. (Scheme 17). The precursor of the general formula (XVII) was prepared according to scheme 1 by using the secondary amine of the general formula (XVI).

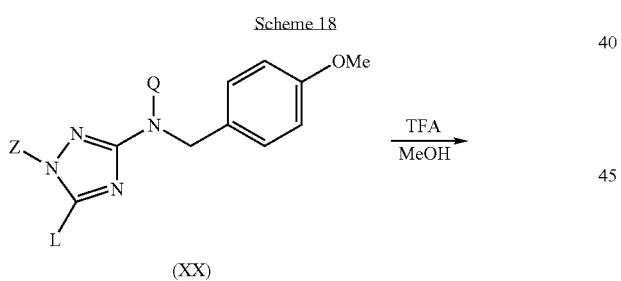

The triazole of the general formula (I-ab) can be prepared by acid catalyzed removal of the para methoxybenzyl (PMB) protecting group in the triazole of the general formula (XX). Said deprotection is best performed using TFA and a protic co-solvent such as methanol or the like (Scheme 18).

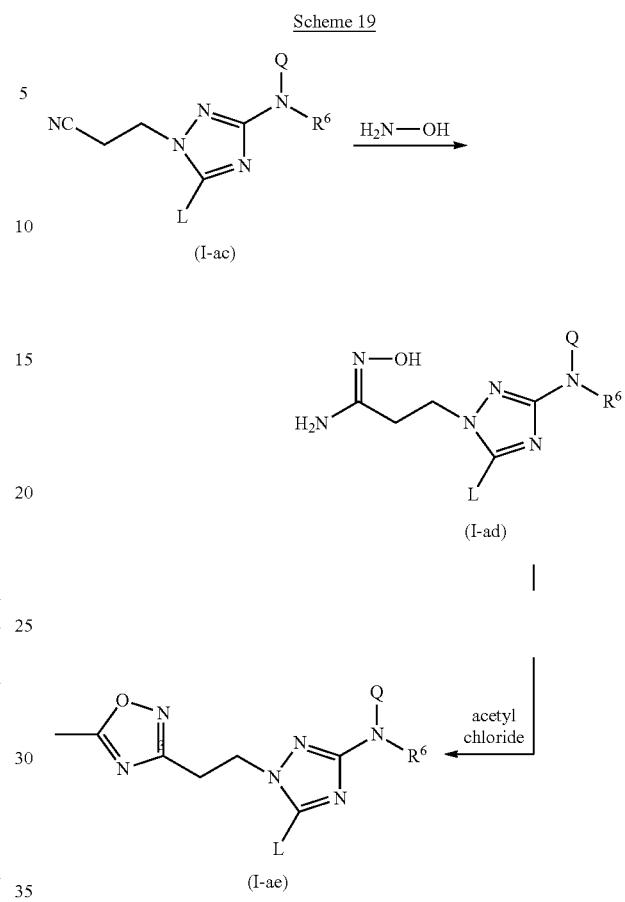

The 1,2,4-oxadiazole of the general formula (I-ae), linked through the 3-position to the triazole core, can be prepared in 2 steps from the corresponding nitrile of the general formula (I-ac). The first step involves the formation of the amino oxime of the general formula (I-ad). This can be achieved by treating the nitrile (I-ac) with hydroxyl amine HCl in the presence of an inorganic base, such as sodium hydroxide or the like, in aqueous environment, preferentially in the presence of a water miscible organic co-solvent, such as ethanol, or the like. The second step involves cyclization to afford the oxadiazole of the general formula (I-ae), using a suitable electrophile, such as acetic anhydride, or, more preferentially acetyl chloride, in a polar protic solvent, such as THF or the like, in the presence of an amine base, such as diisopropyl ethyl amine. Said transformation is best carried out by using microwave heating, at a temperature range between 120° C. and 170° C., preferably at 150° C. (Scheme 19).

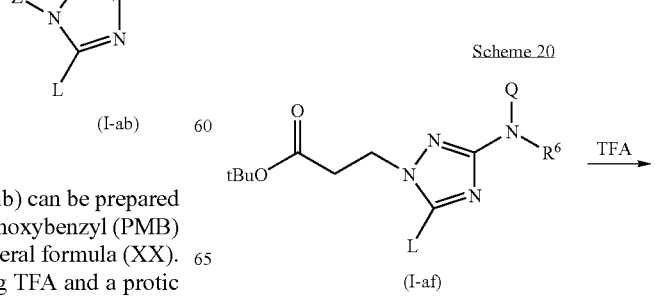

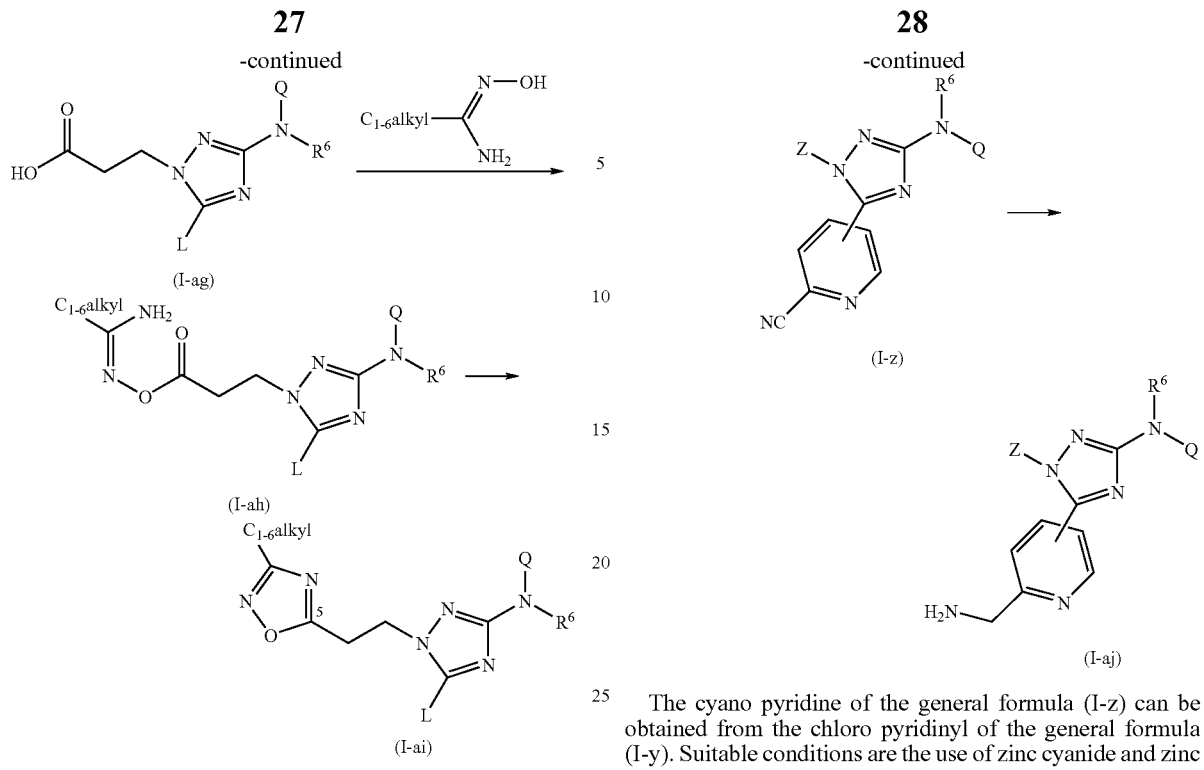

The 1,2,4-oxadiazole of the general formula (I-ai), linked through the 5-position to the triazole core, can be prepared in 3 steps from the corresponding tert butyl carboxylate of the general formula (I-af). The first step involves the deprotection of the tert butyl ester moiety in (I-af) to afford the carboxylic acid of the general formula (I-ag). This can be done by treating (I-af) in trifluoro acetic acid as the solvent at room temperature. The second step involves condensation with an amide oxime to give the intermediate of the general formula (I-ah). This can be done using a condensation reagent, such as diisopropyl carbodiimide (DIC) or the like, in the presence of an acylation catalyst, such as hydroxybenzotriazole (HOBt) or the like. Suitable solvents are dichloromethane and DMF, or mixtures thereof. This transformation can be performed between temperatures of −10° C. and 25° C. The third step involves cyclization to afford the oxadiazole of the general formula (I-ai). A suitable method is the use of a dehydrating agent, such as DIC or the like, in a polar aprotic solvent, such as acetonitrile or the like. Said transformation is best carried out by using microwave heating, at a temperature range between 120° C. and 170° C., preferably at 150° C. (Scheme 20).

The cyano pyridine of the general formula (I-z) can be obtained from the chloro pyridinyl of the general formula (I-y). Suitable conditions are the use of zinc cyanide and zinc dust, catalyzed by Pd$_2$(dba)$_3$ in the presence of a ligand, such as dppf (1,1'-bis(diphenylphosphino)-ferrocene). The reaction further requires a polar solvent, such as DMA or the like, and is best performed at elevated temperature, such as 100° C. in a microwave oven. The nitrile of the general formula (I-z) can be transformed into the amine of the general formula (I-aj) applying an hydrogen atmosphere. A suitable catalyst is Raney Nickel and the reaction is best performed in a solvent mixture containing methanol and ammonia (Scheme 21).

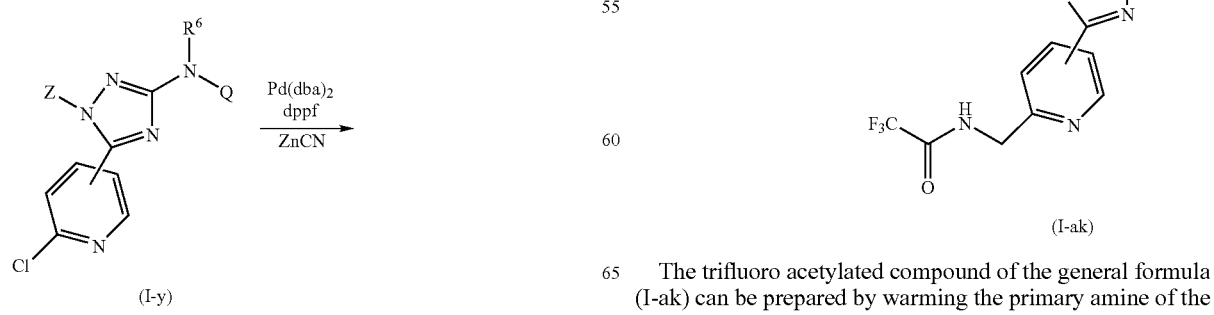

The trifluoro acetylated compound of the general formula (I-ak) can be prepared by warming the primary amine of the general formula (I-aj) in trifluoro acetic acid (Scheme 22).

Scheme 23

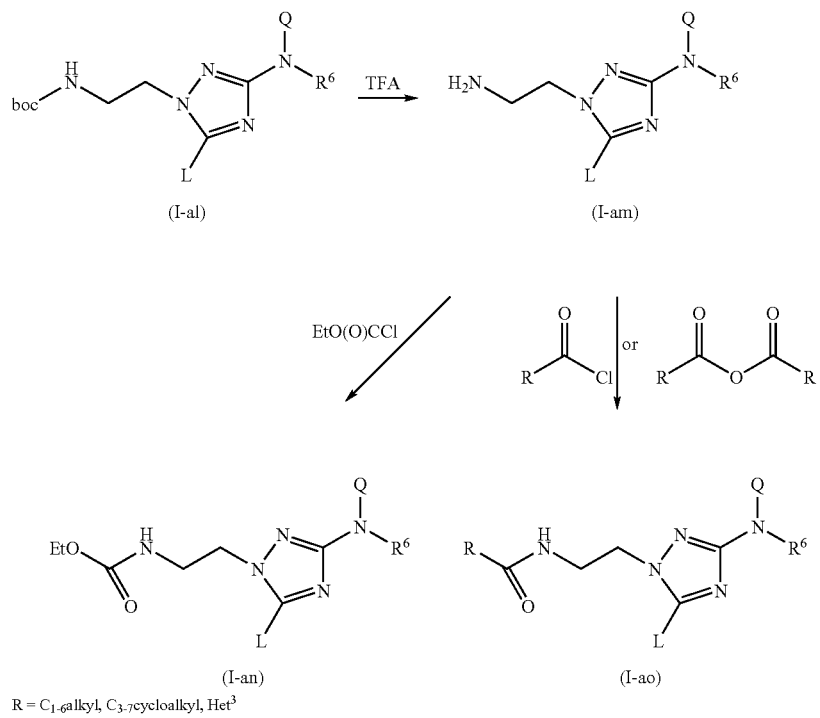

R = $C_{1-6}$alkyl, $C_{3-7}$cycloalkyl, Het³

The ethyl carbamate of the general formula (I-an) can be prepared in 2 steps from the protected amine of the general formula (I-al). In the first step the Boc(tert-butoxycarbonyl) protecting group is removed by treatment of (I-al) with excess trifluoro acetic acid and a suitable organic co-solvent, such as dichloromethane or the like. In the second step the amine of the general formula (I-am) is reacted with ethyl chloro formate, in the presence of an amine base, such as triethyl amine or the like, in a solvent such as dichloromethane, or the like. Said reaction is best carried out between a temperature of 0° C. and 25° C. The amide of the general formula (I-ao) can also be prepared through the intermediacy of the amine of the general formula (I-am). This transformation involves the treatment of the amine (I-am) with an acylating agent, such as acetic anhydride when R=methyl or an acid chloride, in the presence of an amine base, such as triethyl amine or the like, in a halogenated solvent, such as dichloromethane. Optionally, an acylation catalyst is used, such as dimethylamino pyridine (DMAP) or the like (Scheme 23).

Scheme 24

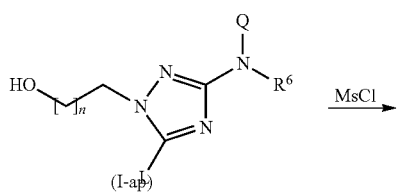

-continued

[structure (I-aq) with MsO group]

[structure (I-ar) with MeO group, MeOH arrow]

n = 1-5

Methoxy alkyl triazoles of the general formula (I-ar) can be prepared in 2 steps from the corresponding hydroxyl alkyl triazoles of the general formula (I-ap). In the first step, the hydroxyl function is transformed into a suitable leaving group, such as the mesylate of the general formula (I-aq). More specifically, the alcohol (I-ap) is treated with mesyl chloride in the presence of an amine base, such as triethyl amine or the like, in a halogenated solvent, such as dichloromethane or the like, at room temperature. In the second step, the mesylate (I-aq) is treated in methanol in the presence of a catalytic amount of a carboxylic acid, such as acetic acid or the like, and heated at elevated temperatures in a microwave oven. An optimal reaction temperature is in the range 140-180° C., preferably 160° C. (Scheme 24).

Scheme 25

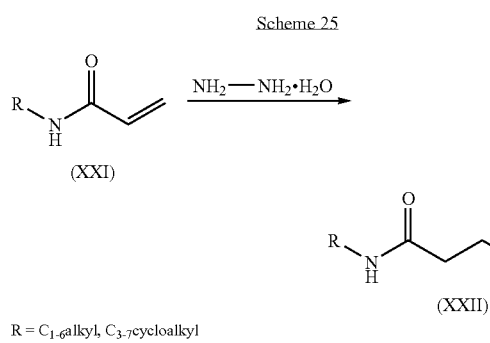

R = C$_{1-6}$alkyl, C$_{3-7}$cycloalkyl

The hydrazine of the general formula (XXII) can be obtained from the acrylamide of the general formula (XXI) by treatment with an equimolar or excess amount of hydrazine hydrate in a suitable protic solvent, such as methanol or the like (Scheme 25).

Scheme 26

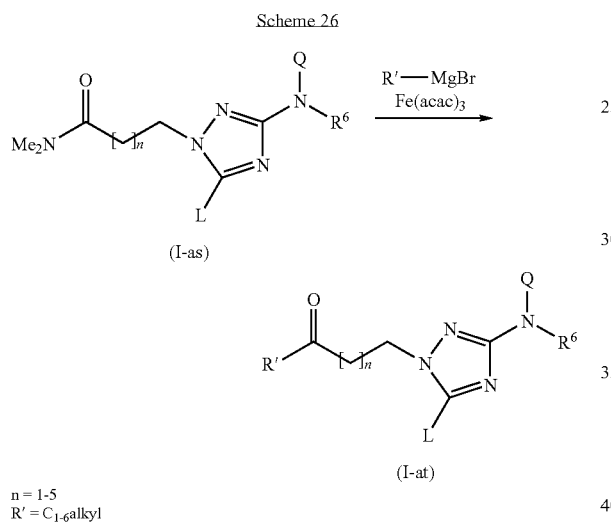

n = 1-5
R' = C$_{1-6}$alkyl

Dialkyl ketones of the general formula (I-at) can be prepared by treatment of the dimethyl amide precursor of the general formula (I-as) with an excess (15 equiv.) Grignard reagent R'—MgBr in the presence of a catalytic amount of Fe(acac)$_3$ in a solvent system consisting of 85% THF and 15% NMP. Said transformation can be performed in a temperature range 0° C. and 50° C., most preferably between 0° C. and 25° C. (Scheme 26).

Scheme 27

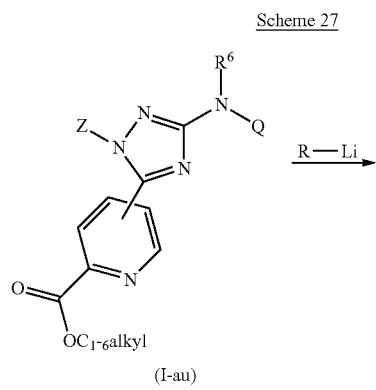

R = C$_{1-6}$alkyl

-continued

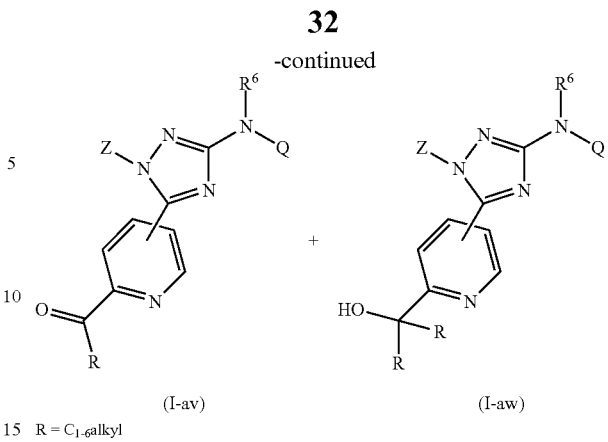

A mixture of the ketone of the general formula (I-av) and the carbinol of the general formula (I-aw) can be prepared from the ester of the general formula (I-au). The transformation involves treating (I-au) with an excess of an alkyl lithium reagent in an aprotic solvent such as THF or the like, at low temperature, preferably −78° C. (Scheme 27).

Scheme 28

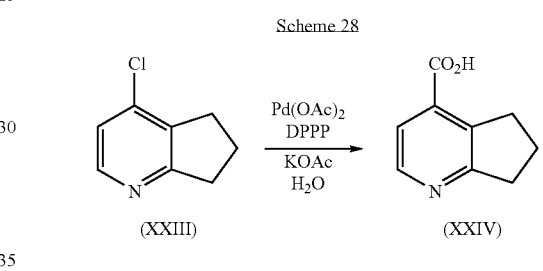

The carboxylic acid (XXIV) can be obtained from the chloro pyridinyl (XXIII) through a CO insertion reaction. Suitable conditions are the use of palladium acetate in the presence of a ligand, such as 1,3-bis(diphenylphosphino)propane (DPPP), under a CO atmosphere at a pressure of 50 atm, and an inorganic base such as potassium acetate or the like. The reaction further requires water and a polar organic co-solvent, such as THF and the like. The reaction is best performed at high temperature, such as 150° C. (Scheme 28).

Pharmacology

The compounds of the present invention were found to be positive allosteric modulators of the α7 nicotinic receptor. The α7 nicotinic receptor (α7 nAChR) belongs to the super-family of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans.

Genetic evidence for its association with schizophrenia is seen in the form of strong linkage between a schizophrenia marker (sensory gating deficit) and the α7 locus on 15q13-14 and polymorphisms in core promoter region of the α7 gene. Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitization.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatable and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein the PAM-induced increase in α7 nicotinergic transmission can be beneficial. As a PAM relies on the presence of the natural transmitter the potential for over-stimulation is limited by the breakdown/clearance mechanisms for the natural transmitter.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include 1,4-Diazabicyclo[3.2.2]nonane-4-carboxylic acid, 4-bromophenyl ester, monohydrochloride (SSR180711A);

(−)-spiro[1-azabicyclo[2.2.2.]octane-3,5'-oxazolidine]-2'-one;

3-[(2,4-Dimethoxy)Benzylidene]-Anabaseine Dihydrochloride (GTS-21);

[N-[(3R)-1-Azabicyclo[2.2.2]oct-3-yl]-4-chlorobenzamide Hydrochloride]PNU-282987).

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

In view of the above described pharmacological properties, the compounds according to formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the α7 nicotinic receptor is beneficial.

In view of the utility of the compounds according to formula (I), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, an N-oxide form, a pharmaceutically acceptable addition salt, a solvate, or a quaternary amine thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 μM, and more usually 5 nM to 50 μM. To obtain these treatment concentrations, a patient in need of treatment likely will be administered between 0.01 mg/kg to 2.50 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional α7 nicotinic receptor agonists, such as for example 1,4-Diazabicyclo[3.2.2]nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy)Benzylidene]-Anabaseine Dihydrochloride (GTS-21); or [N-[(3R)-1-Azabicyclo[2.2.2]oct-3-yl]-4-chlorobenzamide Hydrochloride]PNU-282987). Thus, the present invention also relates to the combination of a compound according to formula (I) and a α7 nicotinic receptor agonist. Said combination may be used as a medicine. The present invention also relates to a product comprising (a) a compound according to formula (I), and (b) a α7 nicotinic receptor agonist, as a combined preparation for simultaneous, separate or sequential use in the treatment of diseases wherein modulation of the α7 nicotinic receptor is beneficial. The different drugs may be combined in a single preparation together with pharmaceutically acceptable carriers.

EXPERIMENTAL PART

Hereinafter, the term 'THF' means tetrahydrofuran, 'EtOAc' means ethyl acetate, 'DIPE' means diisopropyl ether, 'CH$_2$Cl$_2$' means dichloromethane, 'HOAc' means acetic acid, 'KOAc' means potassium acetate, 'HBTU' means 1-[bis(dimethylamino)methylene]-1H-benzotriazolium-hexafluorophosphate(1-)-3-oxide, 'DMF' means N,N-dimethylformamide, 'DIPEA' means N-ethyl-N-(I-methylethyl)-2-propanamine, 'CH$_3$CN' means acetonitrile, 'CH$_3$OH' means methanol, 'Na$_2$CO$_3$' means carbonic acid disodium salt, 'NaH' means sodium hydride, 'NH$_4$HCO$_3$' means carbonic acid monoammonium salt, 'NH$_4$OAc' means acetic acid ammonium salt, 'CH$_3$NH$_2$' means methanamine, 'NH$_4$Cl' means ammonium chloride, 'NaHCO$_3$' means carbonic acid monosodium salt, 't-BuOH' means 2-butyl-2-propanol, 'HOBt' means 1-hydroxy-1H-benzotriazole, 'EDCI' means N'-(ethylcarbonimidoyl)-N,N-dimethyl-1,3-propanediamine monohydrochloride, 'TFA' means trifluoroacetic acid, 'Pd(OAc)$_2$' means palladium acetate, 'Et$_3$N' means triethylamine, 'Pd$_2$(dba)$_3$' means tris[μ-[(1,2-η:4,5-η)(1E,4E)-1,5-diphenyl-1,4-pentadien-3-one]]dipalladium, 'CH$_3$MgBr' means bromomethylmagnesium, 'Et$_2$O' means diethyl ether.

A number of compounds were purified by reversed phase high-performance liquid chromatography using one of the methods below (indicated in the compound procedure with method A and method B).

HPLC Method A

The product was purified by high-performance liquid chromatography (Shandon Hyperprep® C18 BDS (Base Deactivated Silica) 8 μm, 250 g, I.D. 5 cm). Three mobile phases were used (phase A: a 0.25% NH$_4$HCO$_3$ solution in water; phase B: CH$_3$OH; phase C: CH$_3$CN). First, 75% A and 25% B with a flow rate of 40 ml/min was hold for 0.5 minutes. Subsequently, a gradient was applied to 50% B and 50% C in 41 minutes with a flow rate of 80 ml/min. Subsequently, a gradient was applied to 100% C in 20 minutes with a flow rate of 80 ml/min and hold for 4 minutes.

HPLC Method B

The product was purified by high-performance liquid chromatography (Shandon Hyperprep® C18 BDS (Base Deactivated Silica) 8 m, 250 g, I.D. 5 cm). Three mobile phases were used (phase A: 90% of a 0.5% NH$_4$OAc solution in water+10% CH$_3$CN; phase B: CH$_3$OH; phase C: CH$_3$CN). First, 75% A and 25% B with a flow rate of 40 ml/min was hold for 0.5 minutes. Subsequently, a gradient was applied to 50% B and 50% C in 41 minutes with a flow rate of 80 ml/min. Subsequently, a gradient was applied to 100% C in 20 minutes with a flow rate of 80 ml/min and hold for 4 minutes.

A. Preparation of the Intermediates

Example A1 a) Preparation of Intermediate 1

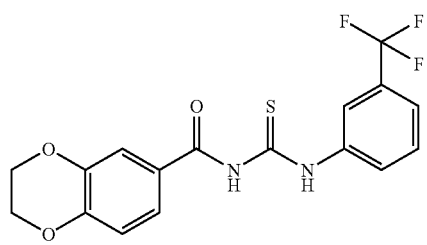

A mixture of thiocyanic acid ammonium salt (0.0164 mol) in 2-propanone (50 ml) was stirred at room temperature. Subsequently, 2,3-dihydro-1,4-benzodioxin-6-carbonyl chloride (0.015 mol) was added portionwise. The reaction mixture was refluxed for 15 minutes. Subsequently, 3-(trifluoromethyl)benzenamine (0.0125 mol) in 2-propanone (q.s.) was added dropwise to the reaction mixture at reflux. The reaction mixture was stirred at reflux for 30 minutes. Subsequently, the reaction mixture was poured onto a mixture of ice and Na$_2$CO$_3$ (q.s.). The precipitate was filtered off and dried, yielding 4.90 g (100%) of intermediate 1.

b) Preparation of Intermediate 2

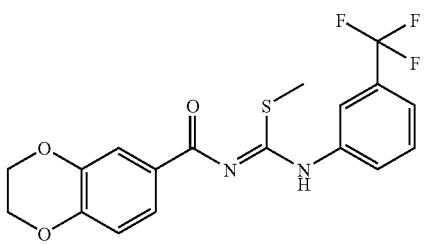

Reaction under N$_2$ flow. A 60% NaH solution (0.014 mol) in THF (150 ml) was stirred on an ice bath. Subsequently, intermediate 1 (0.0125 mol) was added portionwise. The reaction mixture was stirred for another 30 minutes at 0° C. Subsequently, iodomethane (0.014 mol) in THF (q.s.) was added dropwise to the reaction mixture. The reaction mixture was allowed to warm up to room temperature. The reaction mixture was decomposed with H$_2$O and the organic solvent was evaporated. The aqueous concentrate was extracted with CH$_2$Cl$_2$. The separated organic layer was dried, filtered and the solvent was evaporated. The residue was purified by column chromatography over silica gel (eluent: CH$_2$Cl$_2$/CH$_3$OH 99/1 and 98/2). The product fractions were collected and the solvent was evaporated, yielding 4.95 g (100%) of intermediate 2.

Example A2

Preparation of Intermediate 3

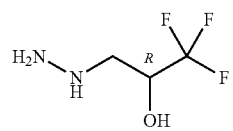

Hydrazine (.x H$_2$O) (25 g) was stirred in a sealed tube at 70° C. (2R)-2-(trifluoromethyl)-oxirane (2.0 g, 0.018 mol) was added slowly (syringe) in the hydrazine at 60° C. The reaction mixture was stirred for 4 hours at 60° C. The solvent was evaporated (reduced pressure; 9 mm Hg/50° C.). A white solid was formed. Toluene was added and evaporated again (at 50° C.), yielding 2.6 g of intermediate 3 (crude, used as such in the next reaction step).

Example A3 a) Preparation of Intermediate 4

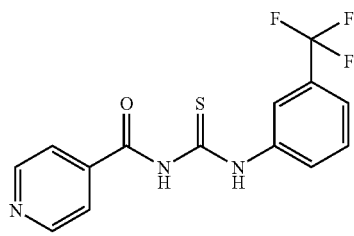

A mixture of thiocyanic acid ammonium salt (0.081 mol) in 2-propanone (120 ml) was stirred for 1 hour. Subsequently, 4-pyridinecarbonyl chloride hydrochloride (0.074 mol) was added. The reaction mixture was stirred for 15 minutes at reflux. Subsequently, 3-(trifluoromethyl)benzenamine (0.062 mol) in 2-propanone (q.s.) was added dropwise at reflux and the reaction mixture was refluxed for another 30 minutes. The reaction mixture was poured onto a mixture of ice and $Na_2CO_3$. The precipitate was filtered off and subsequently, dried, yielding 9.28 g (46%) of impure intermediate 4 which was used as it is in subsequent reactions.

b) Preparation of Intermediate 5

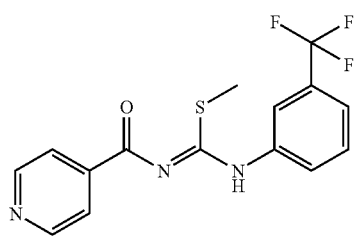

Reaction under $N_2$ flow. A mixture of a 60% NaH solution (0.03 mol) in THF (300 ml) was stirred on an ice bath. Subsequently, intermediate 4 (0.027 mol) was added portionwise. The reaction mixture was stirred for 30 minutes at 0° C. Subsequently, iodomethane (0.03 mol) in THF (q.s.) was added dropwise to the reaction mixture. The reaction mixture was allowed to warm to room temperature. Subsequently, the reaction mixture was poured into $H_2O$ and THF was evaporated. The concentrate was extracted with $CH_2Cl_2$. The separated organic layer was dried, filtered and the solvent was evaporated. The residue was purified by column chromatography over silica gel (eluent: $CH_2Cl_2/CH_3OH$ 99/1 and 98/2). The product fractions were collected and the solvent was evaporated, yielding 4 g (44%) of impure intermediate 5 which was used as it is in subsequent reactions.

Example A5 a) Preparation of Intermediate 10

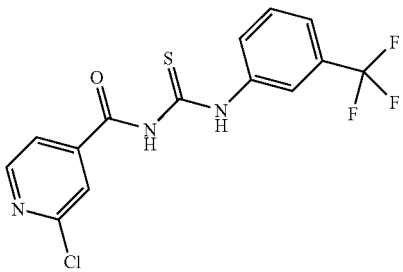

Thiocyanic acid ammonium salt (0.0873 mol) was stirred in 2-propanone (150 ml) at room temperature. 2-Chloro-4-pyridinecarbonyl chloride (0.080 mol) was added portionwise and the mixture was stirred for 30 minutes. A solution of 3-(trifluoromethyl)benzenamine (0.0727 mol) in a small amount of 2-propanone was added dropwise and the reaction mixture was stirred for 4 hours. The solvent was evaporated. The residue was purified by column chromatography over silica gel (eluent: Hexane/EtOAc 90/10 to 50/50). The product fractions were collected and the solvent was evaporated until precipitation resulted. The precipitate was filtered off and dried, yielding 12.630 g (48.3%) of intermediate 10.

b) Preparation of Intermediate 11

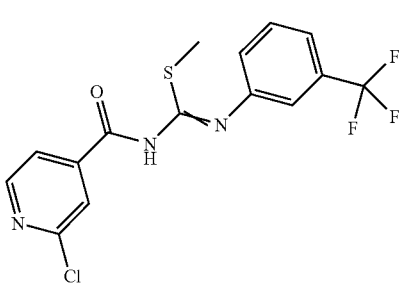

Reaction under $N_2$ atmosphere. A 60% NaH solution (0.0410 mol) was stirred in THF (q.s.) for 30 minutes while cooling on an ice-bath. A solution of intermediate 10 (0.0342 mol) in THF (q.s.) was added dropwise. The resultant reaction mixture was stirred for 30 minutes at 0° C. Iodomethane (0.0342 mol) in THF (q.s.) was added dropwise. The reaction mixture was stirred for 3 hours at room temperature. The reaction was quenched by adding water. The organic solvent was evaporated. The aqueous concentrate was extracted with EtOAc. The extract's solvent was evaporated. The residue was stirred in DIPE, filtered off and dried, yielding 10.977 g (85.9%) of intermediate 11.

Example A6

Preparation of Intermediate 12

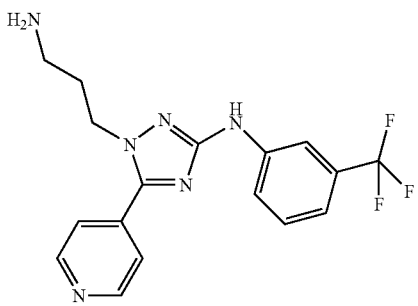

A mixture of compound 64 (0.0006 mol) in CH$_3$OH/NH$_3$ (40 ml) was hydrogenated at 14° C. with Raney Nickel (catalytic quantities) as a catalyst. After uptake of H$_2$ (2 equiv.), the catalyst was filtered off and the filtrate's solvent was evaporated, yielding 0.2 g (100%) of intermediate 12 which was used as such in next reaction step without further purification.

Example A7 a) Preparation of Intermediate 13

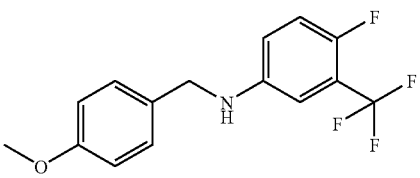

A mixture of 4-fluoro-3-(trifluoromethyl)-benzenamine (0.055 mol) and 4-methoxybenzaldehyde (7.5 g) in CH$_3$OH (200 ml) was reacted with 10% Pd/C (1 g) as a catalyst in the presence of a thiophene solution (1 ml; 4% in DIPE). After uptake of H$_2$ (1 equiv.), the catalyst was filtered off and the filtrate was evaporated, yielding 16.45 g (100%) of intermediate 13.

b) Preparation of Intermediate 14

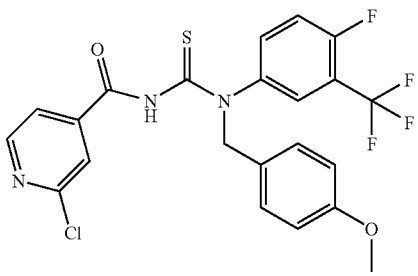

A mixture of thiocyanic acid ammonium salt 0.07 mol) in 2-propanone (100 ml) was stirred at room temperature. 2-Chloro-4-pyridinecarbonyl chloride (0.063 mol) was added and the mixture was stirred for 2 hours at room temperature. Intermediate 13 (0.06 mol) was added and the mixture was stirred for 1 hour at room temperature. The mixture was poured on ice and was then extracted with CH$_2$Cl$_2$. The separated organic layer was dried (MgSO$_4$), filtered and the solvent was evaporated. Toluene was added to the residue and the solvent was evaporated, yielding 29.8 g (100%) of intermediate 14.

c) Preparation of Intermediate 15

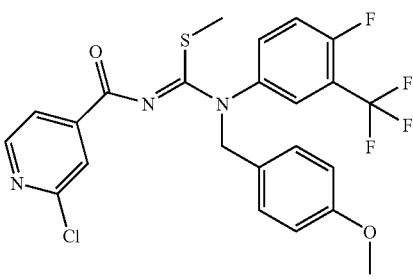

A mixture of 60% NaH (0.07 mol) in THF (200 ml) was stirred under N$_2$-atmosphere on an ice-bath. Intermediate 14 (0.06 mol) was added and the mixture was stirred for 1 hour at 0° C. Then iodomethane (10 g, 0.07 mol) was added and the ice-bath was removed. H$_2$O was added and the reaction mixture was evaporated. H$_2$O was added to the residue and this mixture was extracted with CH$_2$Cl$_2$. The separated organic layer was dried (MgSO$_4$), filtered and the solvent was evaporated, yielding 30.7 g (100%) of intermediate 15.

d) Preparation of Intermediate 16

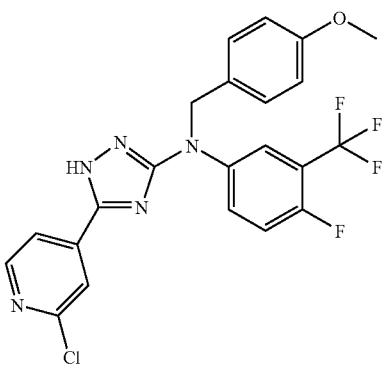

A mixture of intermediate 15 (0.06 mol) and hydrazine monohydrate (0.12 mol) in t-BuOH (200 ml) was stirred and refluxed for 1 hour. The solvent was evaporated and the residue was taken up in H$_2$O. The mixture was extracted with CH$_2$Cl$_2$. The separated organic layer was dried (MgSO$_4$), filtered and the solvent was evaporated. The residue was purified by column chromatography over silica gel (eluent: first 1% CH$_3$OH in CH$_2$Cl$_2$, then 2% CH$_3$OH in CH$_2$Cl$_2$).

The pure fractions were collected and the solvent was evaporated, yielding 15 g (52%) of intermediate 16.

e) Preparation of Intermediate 17

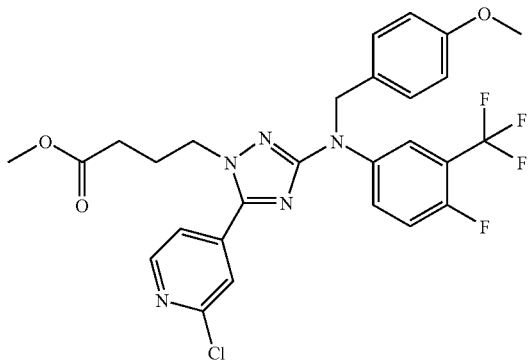

Reaction under N₂ atmosphere. 60% NaH (0.0057 mol) was suspended in THF (40 ml) at room temperature. Intermediate 16 (0.0041 mol) was added in portions. After 20 minutes, 4-iodo-butanoic acid methyl ester (0.0136 mol) was added slowly and the solution was stirred at room temperature for 1 week. Then the mixture was quenched with a saturated NH₄Cl solution and this mixture was extracted with EtOAc (2×). The separated organic layer was washed with brine, dried (Na₂SO₄), filtered and the solvent was evaporated. The residue was purified by Biotage 40M SiO₂ column, eluting from 20% EtOAc/heptane to 30% EtOAc/heptane, finally 50% EtOAc/heptane (most product elutes between 25% and 35%). Two fractions were collected (pure TLC, 30% EtOAc/Heptane.). The solvents of both fractions were evaporated, yielding 1.54 g of the undesired regioisomer and 0.638 g of intermediate 17.

f) Preparation of Intermediate 18

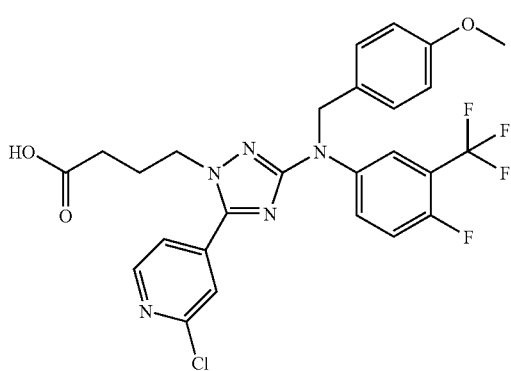

A solution of intermediate 17 (0.0013 mol) and lithium hydroxide monohydrate (0.0062 mol) in THF (20 ml), CH₃OH (5 ml) and H₂O (5 ml) was stirred at room temperature for 6 hours. The mixture was quenched with 1N HCl and the precipitate was collected by filtration, washed with water and CH₃CN and was then dried, yielding 0.7 g of intermediate 18 as a pale solid.

g) Preparation of Intermediate 19

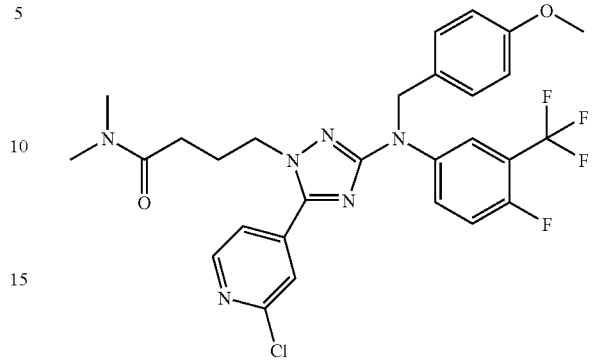

To a solution of intermediate 18 (0.00125 mol) in DMF (10 ml) were added N-methylmethanamine hydrochloride (0.00250 mol), HOBt (0.00375 mol), EDCI (0.00375 mol) and DIPEA (0.00500 mol). The resulting reaction solution was stirred at room temperature for 3 hours. The reaction was quenched with 1N HCl and extracted with EtOAc. The organic phase was separated, washed with a saturated aqueous Na—HCO₃ solution (2×) and dried (Na₂SO₄), filtered and the filtrate's solvent was evaporated, yielding 0.550 g of intermediate 19 as a pale oil.

Example A8

Preparation of Intermediate 21

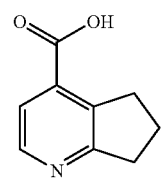

A mixture of 4-chloro-6,7-dihydro-5H-cyclopenta[b]pyridine (0.0520 mol), Pd(OAc)₂ (0.1 g), 1,3-bis(diph-phosphino)propane (0.4 g) and KOAc (10 g) in THF (100 ml) and H₂O (20 ml) was stirred under 50 atm. of CO for 16 hours at 150° C. The mixture was evaporated and water was added. The precipitate was filtered off and dried, yielding 9.20 g (100%) of intermediate 21.

Example A9

Preparation of Intermediate 22

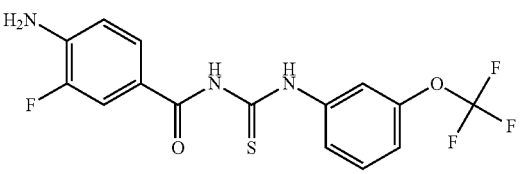

A mixture of

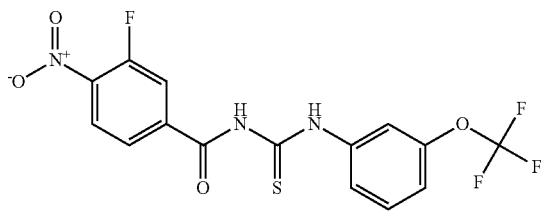

(0.036 mol) in THF (300 ml) was hydrogenated at room temperature with 5% Pd/C and 0.5% $V_2O_5$ (4 g) as a catalyst in the presence of a thiophene solution (1 ml; 4% in DIPE). After uptake of $H_2$ (3 equiv.), the catalyst was filtered off and the filtrate was evaporated, yielding an oily residue. This oil was crystallized from 2-propanol. The precipitate was filtered off and dried, yielding 8.0 g (60%) of intermediate 22.

Example A10

Preparation of Intermediate 23

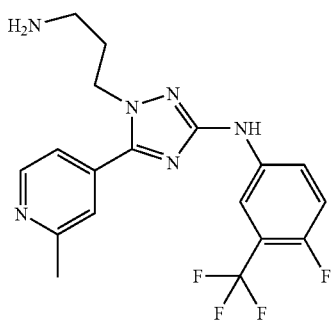

A solution of compound 25 (0.0054 mol) in $CH_3OH/NH_3$ (50 ml) was hydrogenated at 14° C. with Raney Nickel (¼ spoon) as a catalyst. After uptake of $H_2$ (2 eq), the catalyst was filtered off and the filtrate was evaporated. Then $H_2O$ was added. The mixture was extracted with EtOAc. The separated organic layer was dried ($MgSO_4$), filtered and the solvent was evaporated, yielding 0.87 g of intermediate 23.

Example A11 a) Preparation of Intermediate 24

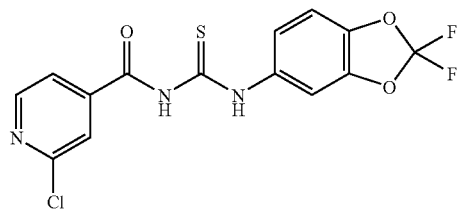

2-Chloro-4-pyridinecarbonyl chloride (0.16 mol) was added dropwise to a stirring mixture of thiocyanic acid ammonium salt (0.175 mol) in 2-propanone (250 ml) at room temperature and the resulting mixture was stirred for 2 hours. 2,2-Difluoro-1,3-benzodioxol-5-amine (25 g, 0.145 mol) was added and the reaction mixture was stirred overnight at room temperature. Then the mixture was poured out on ice. The precipitate was filtered off and dried, yielding intermediate 24 which was used as such in the next reaction step.

b) Preparation of Intermediate 25

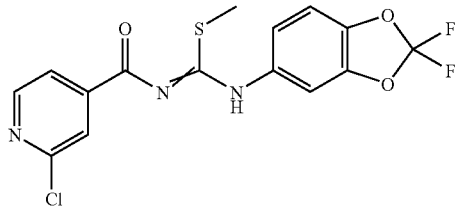

Reaction under $N_2$ flow. 60% NaH (0.16 mol) was stirred in THF (500 ml) on an ice-bath. Intermediate 24 (0.145 mol) was added and the mixture was stirred for 2 hours at 0° C. Iodomethane (0.16 mol) was added and the reaction mixture was allowed to reach room temperature. The reaction mixture was decomposed in $H_2O$. The solvent was evaporated. $H_2O$ was added to the mixture. This mixture was extracted with $CH_2Cl_2$. The separated organic layer was dried ($MgSO_4$), filtered and the solvent was evaporated. The residue was stirred in DIPE. The precipitate was filtered off and dried, yielding 30.4 g (54%) of intermediate 25.

c) Preparation of Intermediate 26

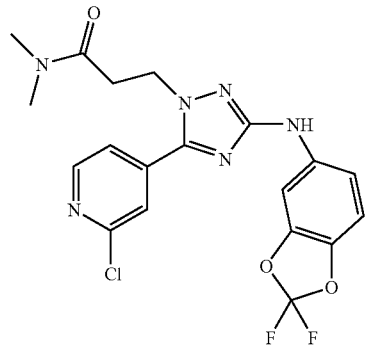

Intermediate 25 (0.0036 mol) was dissolved in 2-methyl-2-propanol (60 ml) and 3-hydrazino-N,N-dimethylpropanamide (0.0072 mol) was added to the solution. The reaction mixture was stirred and refluxed for 5 hours. The solvent was evaporated. The residue was first purified by flash column chromatography over silica gel (Biotage flash purification system; gradient $CH_2Cl_2/CH_3OH$ from 100/0 to 90/10). The desired fractions were collected and the solvent was evaporated. The residue was crystallized from $CH_2Cl_2/DIPE$, yielding 0.69 g of intermediate 26.

Example A12 a) Preparation of Intermediate 27

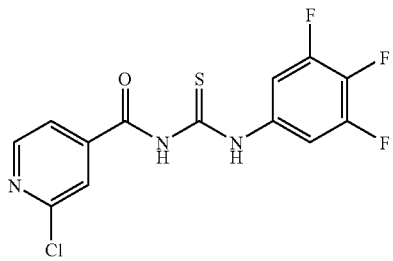

Thiocyanic acid ammonium salt (0.14 mol) was stirred in AcOH (180 ml) at room temperature. 2-chloro-4-pyridinecarbonyl chloride (0.11 mol) was added and the mixture was stirred for 2 hours. 3,4,5-Trifluorobenzenamine (0.1 mol) was added and the reaction mixture was stirred for 1 hour at room temperature. Then the mixture was poured in ice. The precipitate was filtered off and dried, yielding 24.32 g (70%) of intermediate 27.

b) Preparation of Intermediate 28

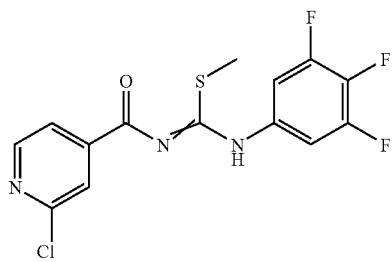

60% NaH (0.075 mol) was stirred in THF (500 ml) on an ice-bath under $N_2$ atmosphere. Intermediate 27 (0.07 mol) was added and then the mixture was stirred for 2 hours at 0° C. Iodomethane (0.075 mol) was added and the ice-bath was removed. $H_2O$ was added and the mixture was evaporated. $H_2O$ was added to the residue and this mixture was extracted with $CH_2Cl_2$. The separated organic layer was dried ($MgSO_4$), filtered and the solvent was evaporated. The residue was stirred in $Et_2O$. The precipitate was filtered off and dried, yielding 17.51 g (70%) of intermediate 28.

c) Preparation of Intermediate 29

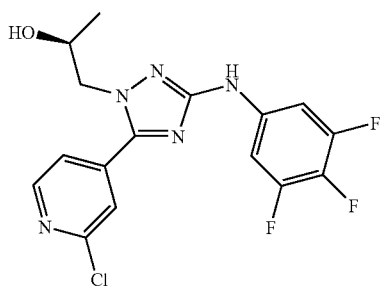

A mixture of intermediate 28 (0.0083 mol), (2S)-1-hydrazino-2-propanol (0.0167 mol) and 2-methyl-2-propanol (50 ml) was stirred and refluxed for 2 hours. Then the solvent was evaporated and $H_2O$ was added to the residue. The mixture was extracted with $CH_2Cl_2$. The separated organic layer was dried ($MgSO_4$), filtered and the solvent was evaporated. The residue was crystallized from $CH_2Cl_2$. The precipitate were filtered off and dried, yielding 2.06 g (65%) of intermediate 29.

Example A 13 a) Preparation of Intermediate 30

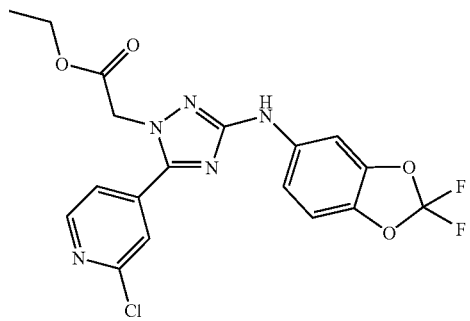

A mixture of intermediate 25 (0.0182 mol), 2-hydrazinylacetic acid, ethyl ester, hydrochloride (1:1) (0.0364 mol) and 2-methyl-2-propanol (75 ml) in DIPEA (0.0364 mol) was stirred and refluxed for 3 hours. The reaction mixture was cooled, the precipitate was filtered off and dried, yielding 2.98 g (37%) of intermediate 30.

b) Preparation of Intermediate 31

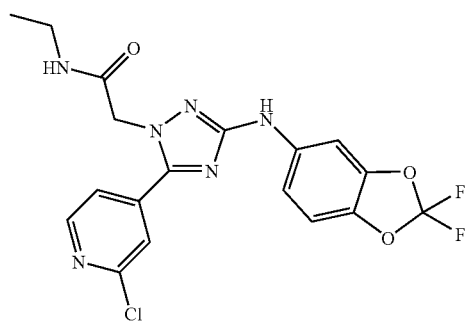

A suspension of intermediate 30 (0.0159 mol) in ethanamine (2M in $CH_3OH$) (80 ml) was heated at 70° C. for 3 hours. The mixture became first homogeneous, and then a precipitate was formed. The precipitate was collected by filtration, washed with ethanol and then DIPE, and was then dried, yielding 4.94 g of intermediate 31

Example A 14 a) Preparation of Intermediate 32

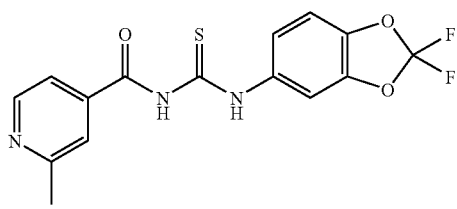

Dissolved 2-methyl-4-pyridinecarbonyl chloride (0.1160 mol) in 2-propanone (400 ml) at room temperature, thiocyanic acid ammonium salt (0.1300 mol) was added. The reaction mixture was stirred for 30 minutes, then 2,2-difluoro-1,3-benzodioxol-5-amine (0.1160 mol) was added slowly by an additional funnel. The reaction mixture was stirred at room temperature for 2 hours, then quenched by $H_2O$ (100 ml), extracted by $CH_2Cl_2$ (3×100 ml), the combined organic phase was dried ($MgSO_4$), filtered, and the solvent was evaporated. The residue was purified by flash column chromatography over silica gel (gradient heptane/EtOAc from 70/30 to 50/50). The product fractions were collected and the solvent was evaporated, yielding 6.5 g of intermediate 32.

b) Preparation of Intermediate 33

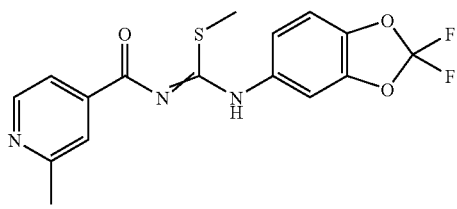

A 60% NaH solution in paraffin (0.018 mol) was stirred in THF (100 ml) on an ice-bath under $N_2$ atmosphere. Intermediate 32 (0.0171 mol) was added and the mixture was stirred for 1 hour at 0° C. Iodomethane (0.018 mol) was added and the ice-bath was removed. Then the solvent was evaporated and water was added to the residue. This mixture was extracted with $CH_2Cl_2$. The separated organic layer was dried ($MgSO_4$), filtered and the solvent was evaporated, yielding 4.5 g of intermediate 33 which was used as such in the next reaction.

c) Preparation of Intermediate 34

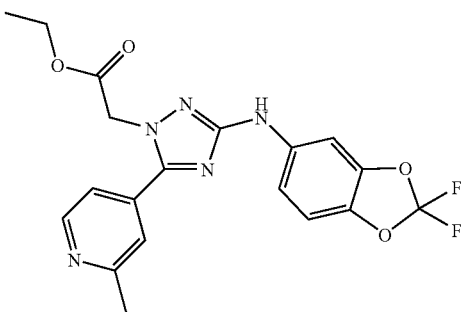

Intermediate 33 (0.0167 mol) was dissolved in 2-methyl-2-propanol (150 ml). Then 2-hydrazinyl-acetic acid, ethyl ester, hydrochloride (1:1) (0.0334 mol) and DIPEA (0.0334 mol) were added. The reaction mixture was stirred and refluxed for 4 hours. The solvent was evaporated. The residue was used without further purification, yielding intermediate 34.

d) Preparation of Intermediate 35

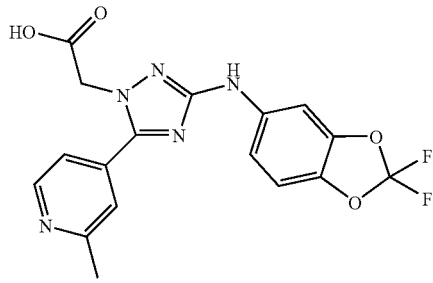

A mixture of intermediate 34 (0.0123 mol) and LiOH (0.0132 mol) in THF (16 ml), $CH_3OH$ (5 ml) and $H_2O$ (5 ml) was stirred at room temperature for 1 hour. Then the solvents were evaporated and the residue was taken up in 20 ml HCl (1 N). The precipitate was filtered off and dried, yielding 0.940 g (100%) of intermediate 35.

Example A15

Preparation of Intermediate 36

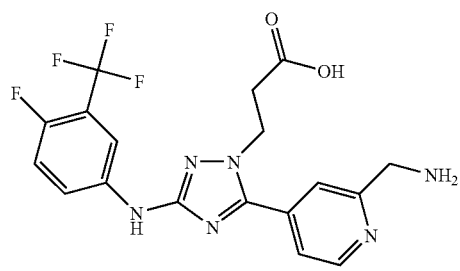

A solution of compound 30 (0.0001 mol) in TFA (5 ml) was shaken overnight at 40° C. Then the solvent was evaporated, yielding intermediate 36 as a TFA-salt.

B. Preparation of the Compounds

Example B1

Preparation of Compound 1

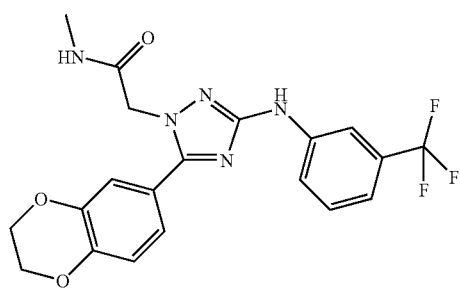

A pressure vessel was charged with a mixture of compound 63 (0.000446 mol) in CH₃NH₂/CH₃OH (20 mol) and the mixture was stirred for 16 hours at 180° C. The solvent was evaporated. The residue was purified by HPLC method B. The desired product fractions were collected and the solvent was evaporated. An aqueous Na₂CO₃ solution (1.5 ml) and CH₂Cl₂ were added to the residue. The mixture was filtered through an Extrelute filter. The filtrate's solvent was evaporated. The residue was dried, yielding 0.096 g (50%) of compound 1.

Example B2

Preparation of Compound 2

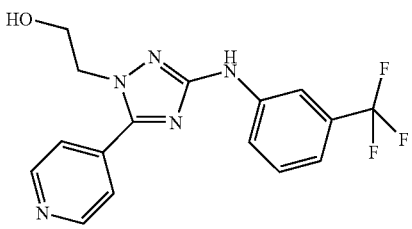

A mixture of intermediate 5 (0.012 mol) and 2-hydrazino-ethanol monohydrochloride (0.012 mol) in ethanol (100 ml) was stirred at reflux for 2 hours. Then the solvent was evaporated and the obtained residue was purified by HPLC method A. The product fractions were collected and the solvent was evaporated. The residue was dried, yielding 0.076 g of compound 2.

Example B3

Preparation of Compound 3

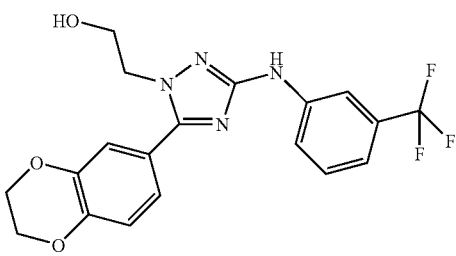

A mixture of intermediate 2 (0.0075 mol) and 2-hydrazino-ethanol monohydrochloride (0.0075 mol) in ethanol (100 ml) was stirred at reflux for 2 hours. The solvent was evaporated. The reaction mixture was crystallized from CH₃CN. The precipitate was filtered off and dried, yielding 1.249 g (41%) of compound 3.

Example B4

Preparation of Compound 4

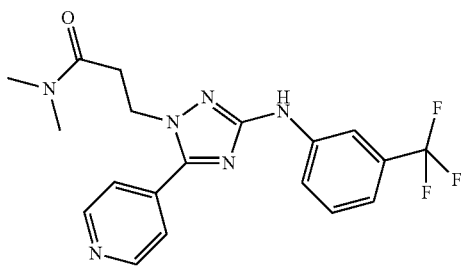

A mixture of compound 65 (0.000242 mol), N-methyl-methanamine hydrochloride (0.000242 mol) and HBTU (0.000363 mol) in DIPEA (0.0009687 mol) and CH₂Cl₂ (10 ml) was stirred overnight at room temperature. The solvent was evaporated. The residue was purified by HPLC method A. The product fractions were collected and the solvent was evaporated. The residue was dried, yielding 0.003 g (3%) of compound 4.

Example B5

Preparation of Compound 5

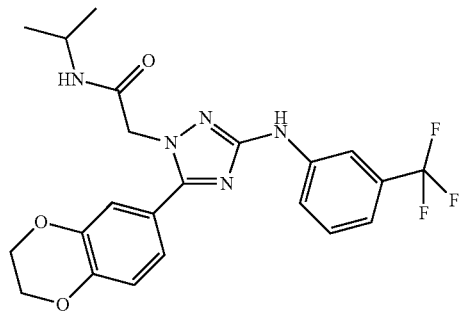

A pressure vessel was charged with a mixture of compound 63 (0.00089 mol) and 2-propanamine (1 g) in THF (20 ml) and the mixture was heated for 16 hours at 175° C. The solvent was evaporated. The residue was purified by HPLC method A. The product fractions were collected and the solvent was evaporated, yielding 0.084 g (20%) of compound 5.

Example B6

Preparation of Compound 6

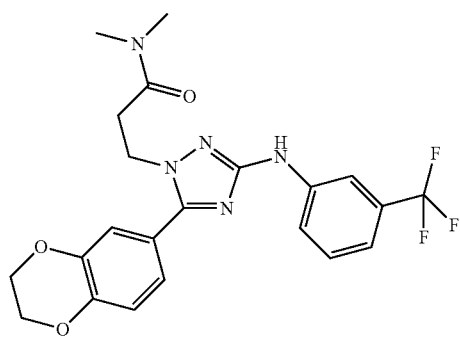

A mixture of compound 67 (0.00023 mol), N-methyl-methanamine hydrochloride (0.00046 mol) and DIPEA (0.00092 mol) in DMF (5 ml) was stirred for 30 minutes at room temperature. HBTU (0.00035 mol) was added and the reaction mixture was stirred overnight at 80° C. The solvent was evaporated. The residue was partitioned between an aqueous $Na_2CO_3$ solution (1 ml) and $CH_2Cl_2$. The mixture was dried over Extrelute. The filtrate's solvent was evaporated. The residue was purified by HPLC method A. The product fractions were collected and the solvent was evaporated, yielding 0.062 g (58%) of compound 6.

Example B7

Preparation of Compound 7

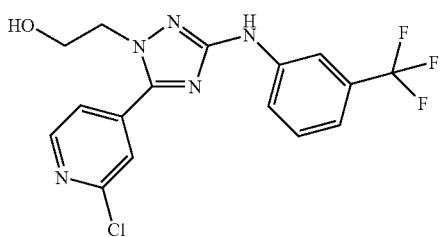

A mixture of intermediate 11 (0.0094 mol) and 2-hydrazino-ethanol monohydrochloride (0.0112 mol) in 2-methyl-2-propanol (60 ml) was stirred and refluxed for 2 hours, then stood overnight at room temperature and the resulting precipitate was filtered off, rinsed with DIPE, then dried, yielding 2.31 g (64%) of compound 7.

Example B8

Preparation of Compound 8

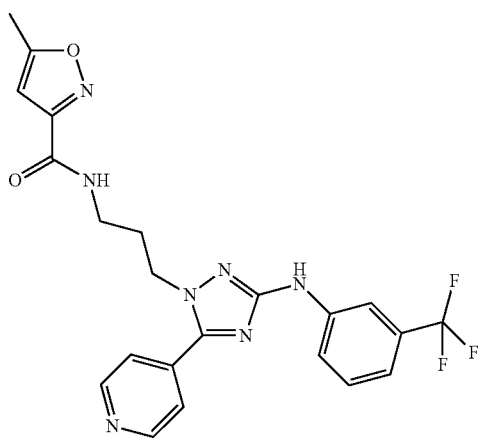

A mixture of intermediate 12 (0.000552 mol), 5-methyl-3-isoxazolecarbonyl chloride (0.000552 mol) and $Et_3N$ (0.001104 mol) in $CH_2Cl_2$ (5 ml) was stirred for 1 hour at room temperature. The solvent was evaporated. Then $Na_2CO_3$ aqueous solution (1 ml) and $CH_2Cl_2$ were added to the residue. The mixture was filtered through an Extrelute filter and the filtrate's solvent was evaporated. The residue was purified by HPLC method A. The product fractions were collected and the solvent was evaporated. The residue was dried, yielding 0.097 g (37%) of compound 8.

Below, compounds are listed that were prepared according to one of the above Examples.

Compound 9

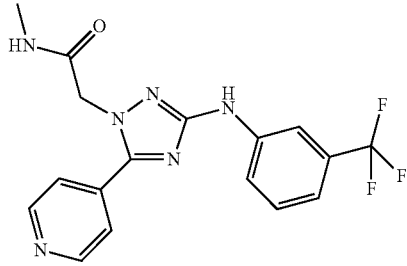

procedure according to the general protocol described for Example B4 using $CH_3NH_2$/THF (2M) and CH2Cl2 as the solvent Compound 10

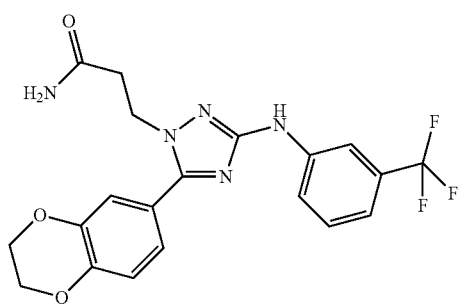

procedure according to the general protocol described for Example B4 using $NH_4Cl$ and DMF as the solvent Compound 11

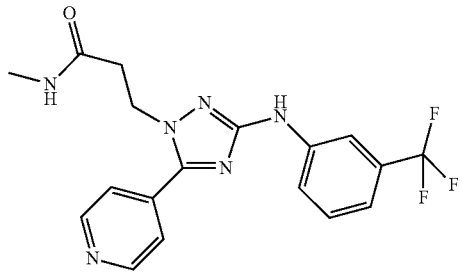

procedure according to the general protocol described for Example B4 using $CH_3NH_2$/THF and $CH_2Cl_2$ as the solvent Compound 12

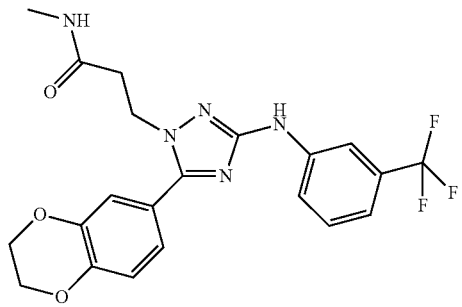

procedure according to the general protocol described for Example B4 using CH$_3$NH$_2$/THF (2M) and DMF as the solvent Compound 13
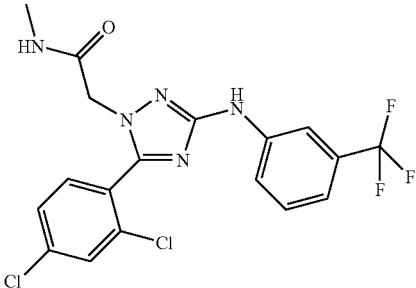

procedure according to the general protocol described for Example B4 using CH$_3$NH$_2$/THF (2M) and CH$_2$Cl$_2$ as the solvent Compound 14
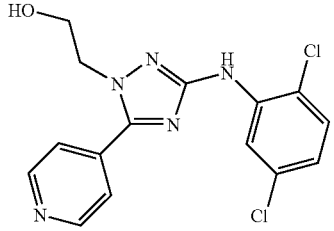

procedure according to the general protocol described for Example B3

Compound 15
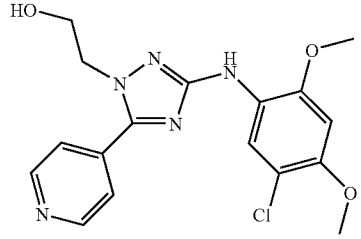

procedure according to the general protocol described for Example B7 using ethanol as the solvent. Pure product was obtained by chromatography over silica gel (eluent: CH$_2$Cl$_2$/CH$_3$OH 99/1 and 90/10)

Compound 16
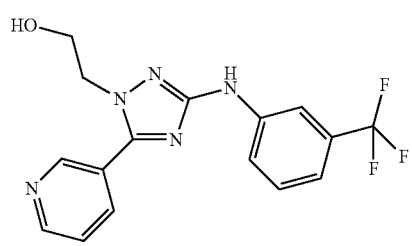

procedure according to the general protocol described for Example B2

Compound 17
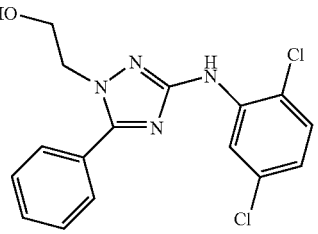

procedure according to the general protocol described for Example B3

Compound 18
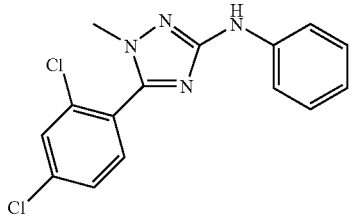

procedure according to the general protocol described for Example B2 using methyl-hydrazine. Pure product was obtained by recrystallisation from 2-propanol Compound 19
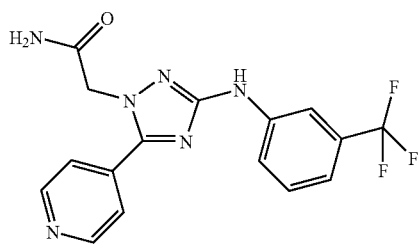

procedure according to the general protocol described for Example B5 at a temperature of 180° C.

Compound 20
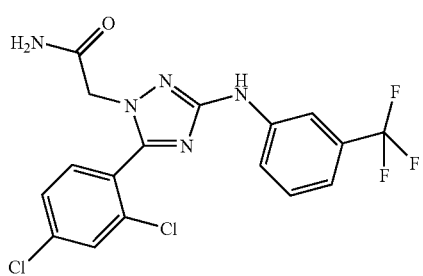

procedure according to the general protocol described for Example B5 using THF/NH$_4$OH/CH$_3$OH as the solvent at a temperature of 150° C.

Compound 21

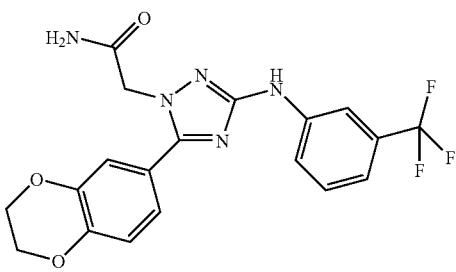

procedure according to the general protocol described for Example B1 using CH$_3$OH/NH$_3$ as the solvent Compound 22

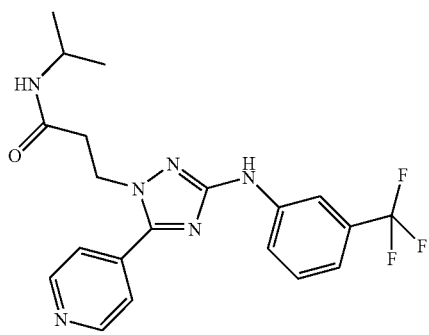

procedure according to the general protocol described for Example B6 with an excess of propanamine Compound 23

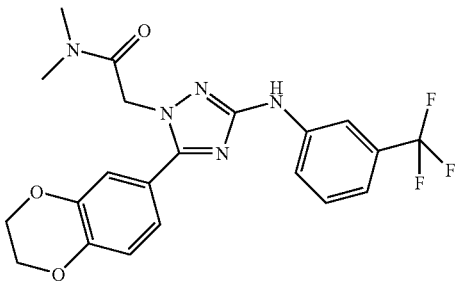

procedure according to the general protocol described for Example B5 using N-methylmethanamine hydrochloride at a temperature of 200° C.

Compound 24

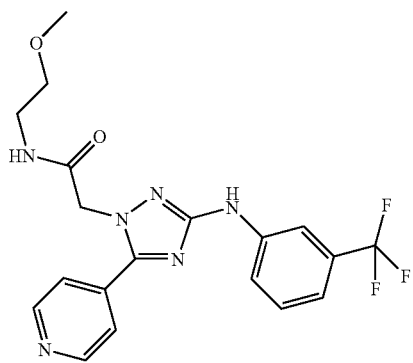

procedure according to the general protocol described for Example B5 using 2-methoxyethanamine Example B9 a) Preparation of Compound 25

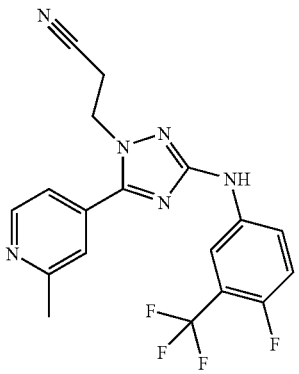

CH$_3$MgBr (0.015 mol) was added slowly to a mixture of

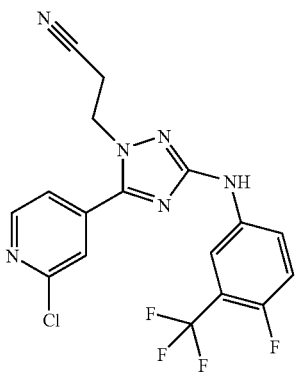

(0.00575 mol), iron (III) acetylacetonate (0.00575 mol) and 1-methyl-2-pyrrolidinone (5 ml) in THF (30 ml) at 0° C. under N$_2$-atmosphere. After the addition, the reaction mixture was warmed up to room temperature and the mixture was stirred for 1 hour. Then the mixture was quenched with H$_2$O. The mixture was extracted with CH$_2$Cl$_2$. The separated organic layer was dried (MgSO$_4$), filtered and the solvent was evaporated. The residue was purified by flash column chromatography (flash master; eluent: CH$_2$Cl$_2$/(10% CH$_3$OH/CH$_2$Cl$_2$) first 100/0, then 50/50, then 0/100). The desired fractions were collected and the solvent was evaporated. The product was precipitated by addition of isopropyl-ether. The precipitate was filtered off and dried, yielding 2.80 g of compound 25.

b) Preparation of Compound 27

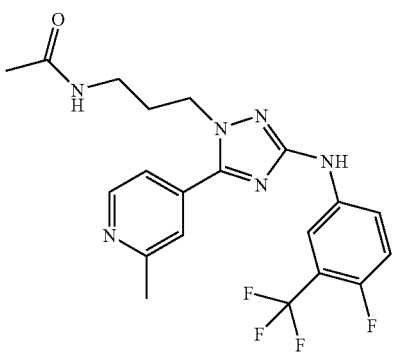

A solution of intermediate 23 (0.0008 mol) in CH$_2$Cl$_2$ (20 ml) was cooled to 0° C. Acetic acid anhydride (0.0009 mol), Et$_3$N (0.077 g, 0.0008 mol) and N,N-dimethyl-4-pyridinamine (0.002 g) were added to the solution. The reaction mixture was warmed up to room temperature and was stirred for 1 hour. Then, the mixture was quenched by H$_2$O and the aqueous mixture was extracted with EtOAc (3×30 ml), dried (MgSO$_4$), filtered and the solvent was evaporated. The residue was crystallized from DIPE. The crystals were filtered off, yielding 0.0401 g of compound 27.

Example B10

Preparation of Compound 28

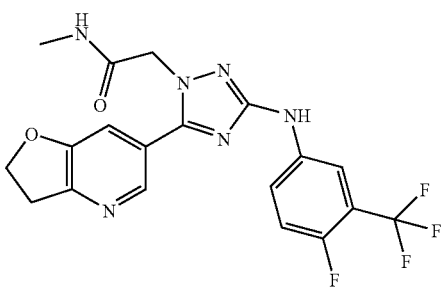

A solution of

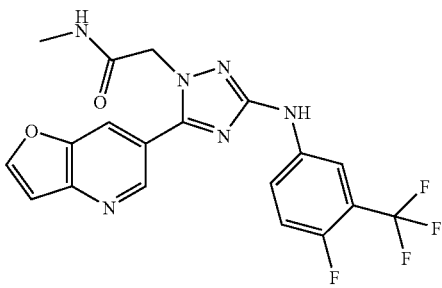

(0.00043 mol) in CH$_3$OH (40 ml) was hydrogenated with 10% Pd/C (0.1 g) as a catalyst. After uptake of H$_2$ (1 equiv.), the catalyst was filtered off and the filtrate was evaporated. The residue was purified by HPLC method A. The product fractions were collected and the solvent was evaporated, yielding 0.087 g of compound 28.

Example B11 a) Preparation of Compound 29

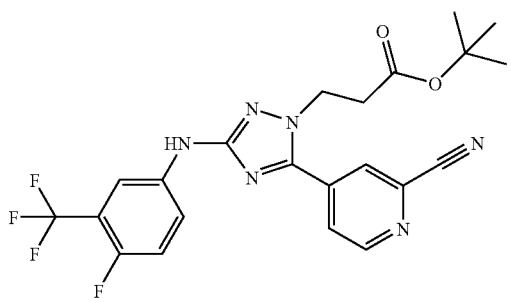

A mixture of

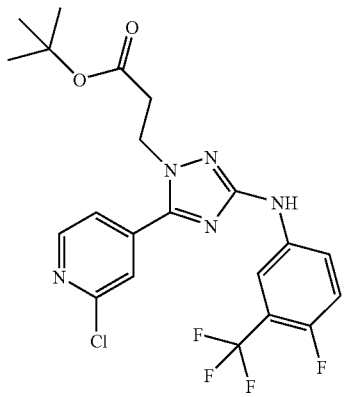

(0.001 mol), Pd$_2$(dba)$_3$ (0.025 g), DPPF (0.0001 mol), Hg.Zn (0.0002 mol) and Zinc cyanide (0.0009 mol) in dimethylacetamide, (5 ml) was heated for 60 minutes at 100° C. using microwave power. The mixture was evaporated to dryness and the residue was purified by flash column chromatography using CH$_2$Cl$_2$ to 10% CH$_3$OH in CH$_2$Cl$_2$ as eluent. The product fractions were evaporated and triturated with DIPE/Hexane. Filtration and drying provided an off-white powder, yielding 0.3594 g (75%) of compound 29.

b) Preparation of Compound 30

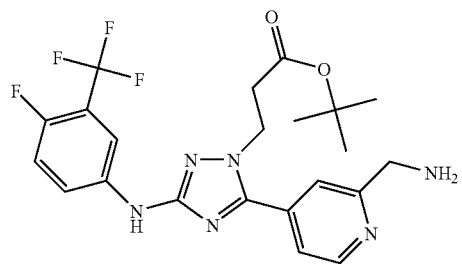

A mixture of compound 29 (0.0007 mol) and Raney Nickel (catalyst) in 7N NH$_3$/CH$_3$OH (40 ml) was hydrogenated with H$_2$ (31 ml) for 1 day at 14° C. The catalyst was filtered off, the solvent was evaporated and the residue was purified by flash column chromatography over silica gel using a gradient of CH$_2$Cl$_2$ to 10% NH$_3$/CH$_3$OH (7 N) in CH$_2$Cl$_2$ as eluent. The product fractions were evaporated, yielding 0.1567 g (48%; white crystals) of compound 30.

Example B12 a) Preparation of Compound 31

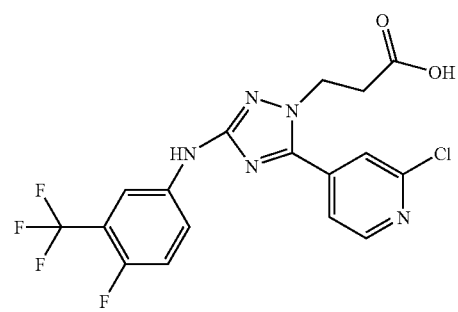

A solution of

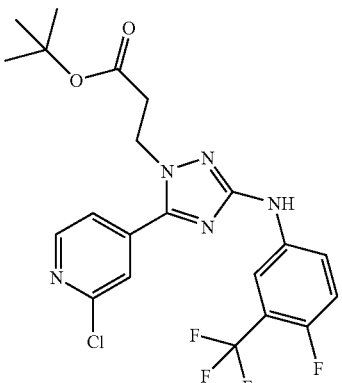

in TFA was shaken for 45 minutes at 40° C., after which the solvent was evaporated, yielding compound 31.

b) Preparation of Compound 32

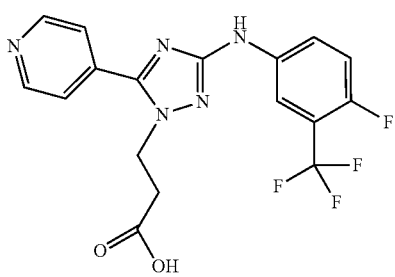

A mixture of compound 31 (0.0023 mol) in THF (50 ml) was hydrogenated with 10% Pd/C (0.3 g) as a catalyst in the presence of a thiophene solution (0.1 ml; 4% in DIPE) and Et$_3$N (1 ml). After uptake of H$_2$ (1 equiv.), the catalyst was filtered off and the filtrate was evaporated, yielding 0.76 g of compound 32.

Example B13

Preparation of Compound 34

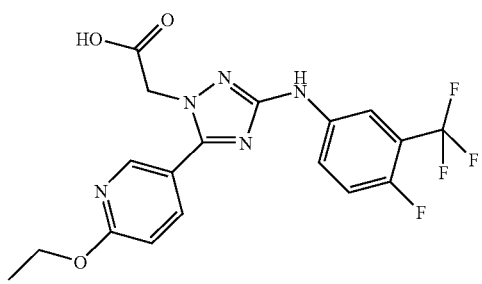

Reaction in microwave oven. A mixture of

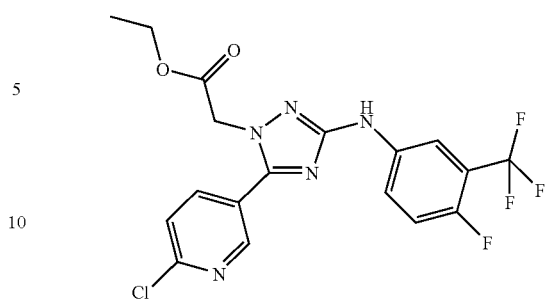

(0.00068 mol) in 21% NaOEt in ethanol (2 ml) and ethanol (3 ml) was heated for 30 minutes at 100° C. The solvent was evaporated. The residue was taken up into water, then acidified with concentrated HCl, and the resulting precipitate was filtered off, washed with water and dried, yielding 0.25 g (80%) of compound 34 as a hydrochloric acid salt (.HCl).

Example B14

Preparation of Compounds 35 and 36

Compound 35

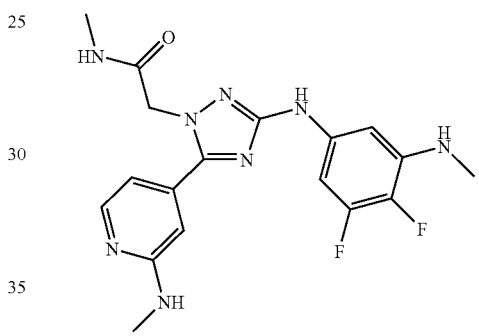

Compound 36

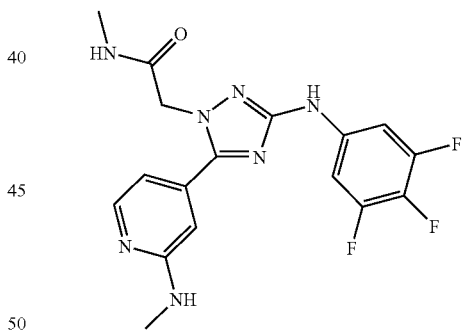

A solution of

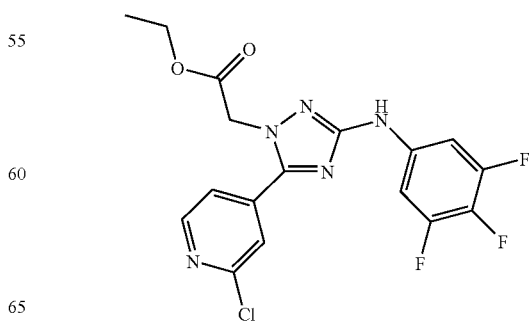

(0.00122 mol) and methanamine (2 g) in ethanol (20 ml) was heated for 24 hours at 160° C. in a microwave oven. The solvent was evaporated and the residue was purified by HPLC method B. Two product fraction groups were collected and their solvent was evaporated. The residue from the first fraction group was dried, yielding 0.018 g (4%) of compound 35. The residue from the second fraction group was treated with an aqueous $Na_2CO_3$ solution. $CH_2Cl_2$ was added. The resulting precipitate was filtered off and dried, yielding 0.151 g (32%) of compound 36.

Compound 37 was prepared in a similar manner as described in Example B14

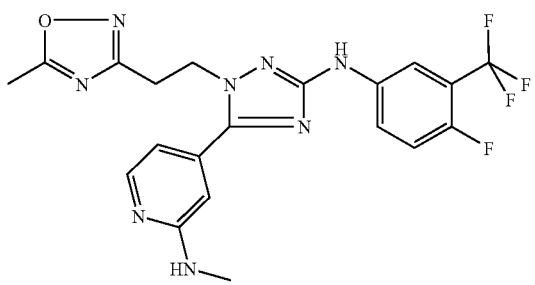

Compound 38 was prepared in a similar manner as described in Example B14

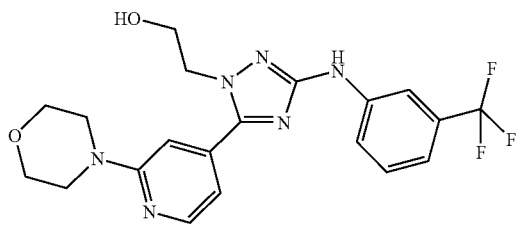

Example B15 a) Preparation of Compound 40

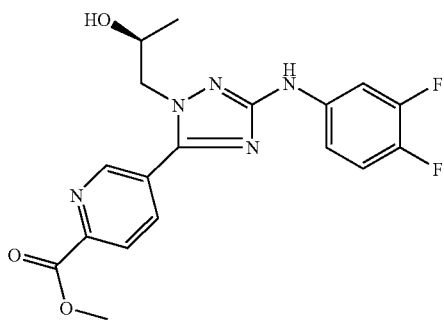

A solution of

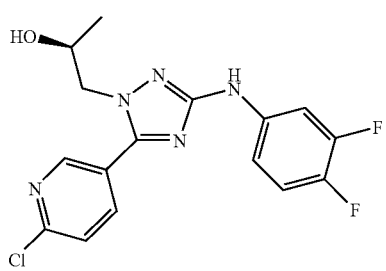

(0.00082 mol), $Pd(OAc)_2$ (0.011 g), 1,3-propanediylbis[diphenylphosphine] (0.041 g) and $CH_3COOK$ (0.5 g) in THF (30 ml) and $CH_3OH$ (10 ml) was reacted for 16 hours under CO atmosphere (50 atm) at 100° C. The reaction mixture was evaporated and the residue was dissolved in $CH_2Cl_2$. This solution was washed with $H_2O$. The organic layer was dried ($MgSO_4$), filtered and the solvent was evaporated. The residue was purified by column chromatography over silica gel (eluent: $CH_2Cl_2$+5% $CH_3OH$). The product fractions were collected and the solvent was evaporated, yielding 0.3 g (94%) of compound 40 (S-enantiomer).

b) Preparation of Compound 41

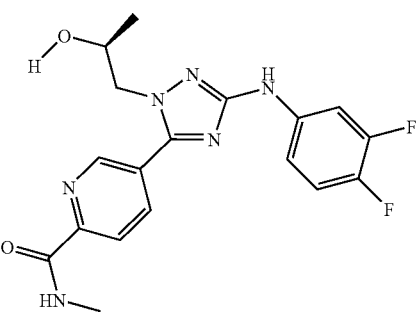

Compound 40 (0.0005 mol) was dissolved in 2M $CH_3NH_2$ in THF (8 ml) and the solution was divided over 2 microwave tubes. The reaction mixture was stirred in a microwave for 2 hours at 100° C. The reaction mixture was concentrated by evaporation. The residue was purified by column chromatography over silica gel (eluent: $CH_2Cl_2$/$CH_3OH$ 95/5). The product fraction was concentrated by evaporation, yielding: 0.158 g (80%) of compound 41.

Example B16

Preparation of Compounds 42 and 43

Compound 42

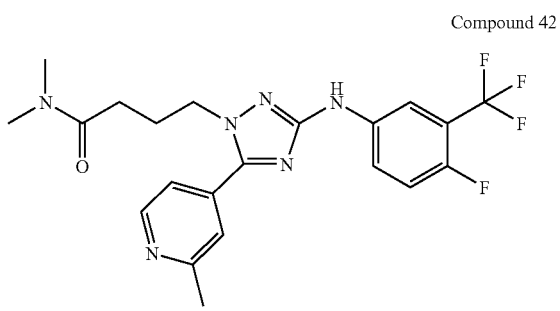

Compound 43

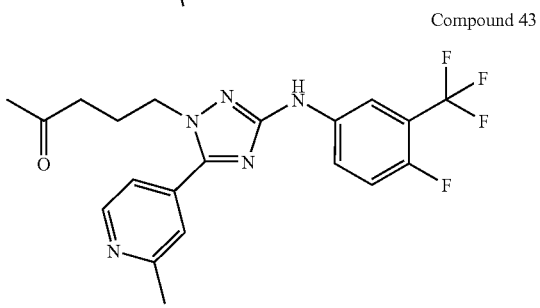

Iron(III) acetylacetonate (0.0001 mol) and 1-methyl-2-pyrrolidinone (0.5 ml) were added to a solution of compound 68 (0.0008 mol) in THF (8 ml). The mixture was cooled to 0° C. under N₂ atmosphere. Then 3M CH₃MgBr in Et₂O (0.0049 mol) was added slowly. After 10 minutes, the mixture was quenched with CH₃OH (1 ml) and saturated NH₄Cl. Then, the mixture was extracted with EtOAc (2×) and the combined organic layers were washed with H₂O, dried (Na₂SO₄), filtered and the solvent was evaporated. The residue was purified by HPLC method A. 2 Different fractions were collected and the solvent was evaporated, yielding 0.143 g (white solid) of compound 42 and 0.105 g (white solid) of compound 43.

Example B17

Preparation of Compound 47

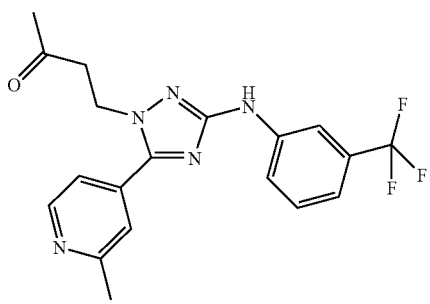

Reaction under N₂ flow. A mixture of

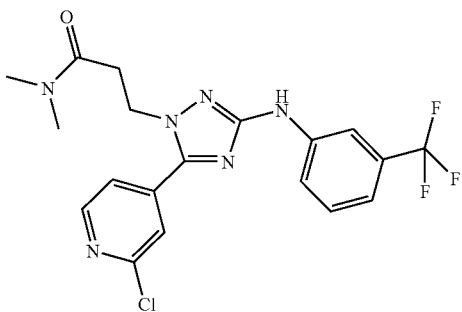

(0.0023 mol) and iron(III) acetylacetonate (0.0002 mol) in THF (12 ml) and 1-methyl-2-pyrrolidinone (3 ml) was stirred on an ice-bath. 3M CH₃MgBr in Et₂O (10 ml) was added and the reaction mixture was stirred for 10 minutes at 0° C. CH₃OH (5 ml) was added and then the solvent was evaporated. The residue was taken up in H₂O and CH₂Cl₂. This mixture was filtered over dicalite. The filtrate was separated. The separated organic layer was dried (MgSO₄), filtered and the solvent was evaporated. The residue was purified by column chromatography over silica gel (eluent: CH₃OH/CH₂Cl₂ from 0/100 to 90/10). The product fractions were collected and the solvent was evaporated, yielding 0.156 g of compound 47.

Example B18

Preparation of Compound 48

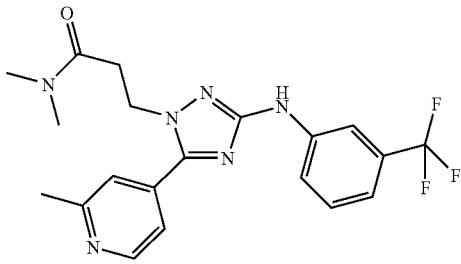

Reaction under N₂ flow. A mixture of

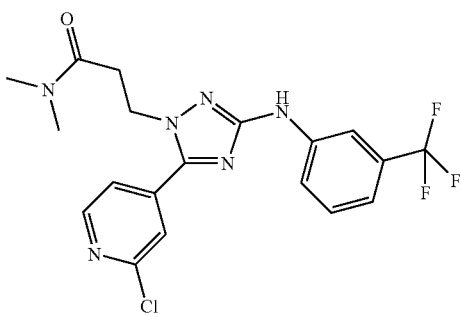

(0.0023 mol) and iron(III) acetylacetonate (0.0002 mol) in THF (12 ml) and 1-methyl-2-pyrrolidinone (3 ml) was stirred on an ice-bath. 3M CH₃MgBr in Et₂O (only 5 ml) was added dropwise (slow) and then CH₃OH (5 ml) was added immediately to the reaction mixture. The solvent was evaporated. The residue was taken up in H₂O (3 ml) and CH₂Cl₂. This mixture was filtered over dicalite. The filtrate's solvent was evaporated. The residue was taken up in DIPE. The mixture was washed 2 times with H₂O. The separated organic layer was dried (MgSO₄), filtered and the solvent was evaporated. The residue was re-crystallized from DIPE, the precipitate was filtered off and dried, yielding 0.608 g (63%) of compound 48.

Example B19

Preparation of Compounds 49 and 50

Compound 49

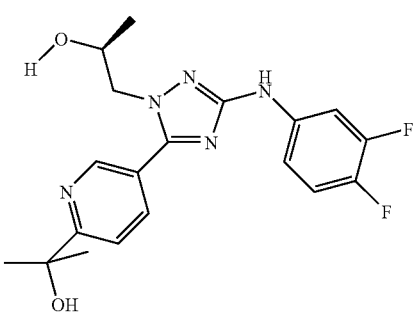

-continued

Compound 50

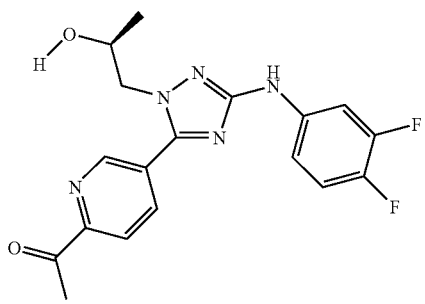

Compound 40 (0.001 mol) was stirred in THF (20 ml) under N₂ atmosphere and the mixture was cooled to −78° C. 1.6M Methyllithium in Et₂O (3.2 ml) was added dropwise at −78° C., and the reaction mixture was stirred for 1 hour at −78° C. Then the cooling bath was removed and the reaction mixture was stirred for 1 hour at room temperature. Then the mixture was poured into a saturated NH₄Cl solution and the resulting mixture was stirred for 15 minutes. The layers were separated. The organic layer was dried (MgSO₄), filtered, and the solvent was evaporated. The residue was purified by silica column chromatography (eluent: CH₂Cl₂/CH₃OH 95/5). The desired fractions were collected and the solvent was evaporated, yielding 0.112 g of compound 49 and 0.165 g of compound 50.

Example B20 a) Preparation of Compound 51

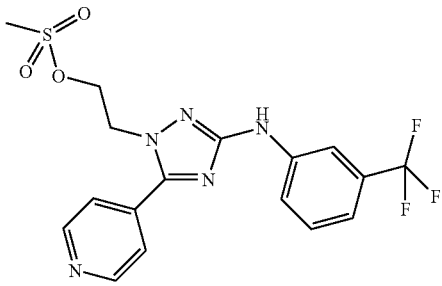

Compound 2 (0.0115 mol) in Et₃N (0.023 mol) and CH₂Cl₂ (200 ml) was stirred at room temperature. Then methanesulfonyl chloride (0.0117 mol) in CH₂Cl₂ (q.s.) was added drop wise. The reaction mixture was stirred for 30 minutes at room temperature and then washed with H₂O. The separated organic layer was dried, filtered and the solvent was evaporated. The residue was purified over silica gel by glass filter (eluent: CH₂Cl₂/(CH₃OH/NH₃) 99/1, 98/2, 97/3 and 96/4). The product fractions were collected and the solvent was evaporated, yielding 2.93 g (60%) of compound 51.

b) Preparation of Compound 52

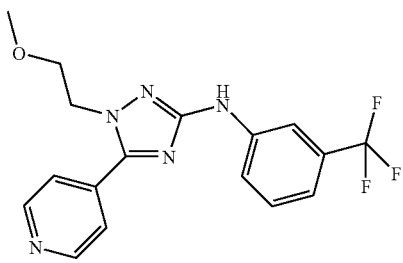

A mixture of compound 51 (0.00234 mol) in CH₃OH (5 ml), H₂O (1 ml) and HOAc (1 drop) was stirred for 45 minutes at 160° C. in a microwave. The solvent was evaporated. The residue was purified by HPLC method A. The product fractions were collected and the solvent was evaporated. The residue was dried, yielding 0.107 g (13%) of compound 52.

Example B21 a) Preparation of Compound 53

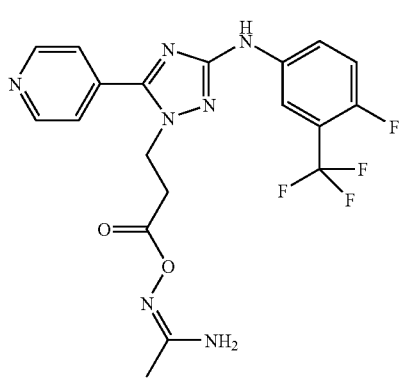

A mixture of compound 32 (0.0019 mol) and (1Z)—N'-hydroxy-ethanimidamide (0.0023 mol) in CH₂Cl₂ (14.3 ml; p.a.) and DMF (1.6 ml; p.a.) was stirred at −10° C. Then HOBt (0.31 g, 0.0023 mol) and N,N'-methanetetraylbis-2-propanamine (0.29 g, 0.0023 mol) were added and the suspension was stirred for 15 minutes at −10° C. Then the reaction mixture was stirred for 2 hours at room temperature (solution after 30 minutes and then precipitate was formed). The precipitate was filtered off and was washed with CH₂Cl₂ and DIPE, yielding 0.385 g of compound 53.

b) Preparation of Compound 69

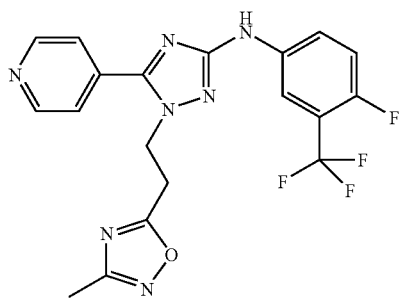

A mixture of compound 53 (0.0006 mol), N,N'-methanetetraylbis-2-propanamine 0.0013 mol) and CH₃CN (10 ml) was stirred in the microwave oven at 150° C. for 40 minutes. After evaporation of the reaction mixture, the residue was purified on silicagel column (eluent: CH₂Cl₂ with 5% CH₃OH). The pure fractions were collected and the solvent was evaporated. The solid residue was dried (vacuum, 70° C.), yielding 0.144 g of compound 69.

Example B22

Preparation of Compound 54

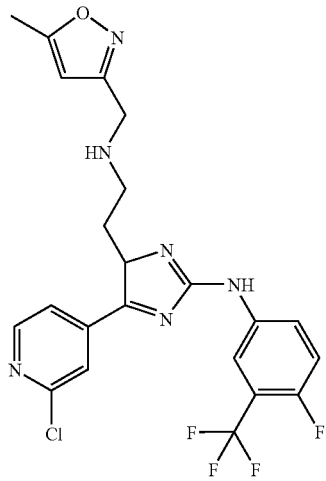

A mixture of

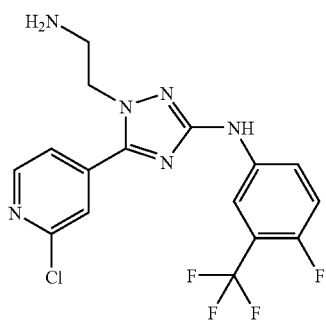

(0.00250 mol), 5-methyl-3-isoxazolecarbonyl chloride (0.00250 mol) and Et₃N (0.00225 mol) in CH$_2$Cl$_2$ (50 ml) was stirred for 1 hour at room temperature. The reaction was quenched with an aqueous Na$_2$CO$_3$ solution. The mixture was extracted with CH$_2$Cl$_2$. The separated organic layer was dried (MgSO$_4$), filtered and the solvent was evaporated. DIPE was added to precipitate some product. The precipitate was filtered off and dried, yielding 0.30 g of compound 54.

Example B23 a) Preparation of Compound 55

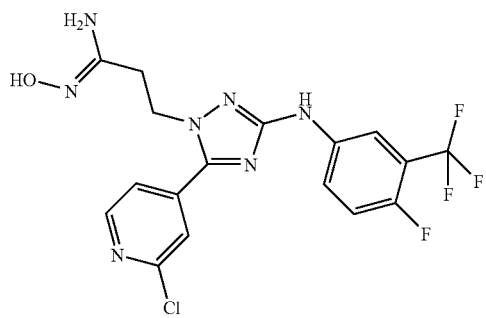

Hydroxylamine hydrochloride (0.011 mol) was stirred in ethanol (20 ml) and then NaOH (0.011 mol) in H$_2$O (10 ml) was added dropwise.

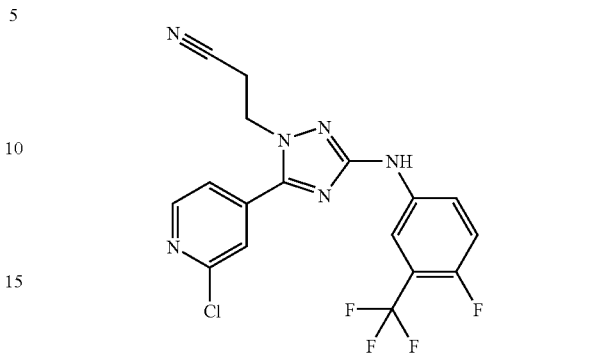

(0.0056 mol) was added portionwise to the mixture, then ethanol (20 ml) was added. The reaction mixture was stirred and refluxed for 4 hours, then cooled to room temperature and the resulting precipitate was filtered off, washed with water/ethanol 1/1, and dried (vacuum, 70° C.), yielding 2 g (80%) of compound 55.

b) Preparation of Compound 56

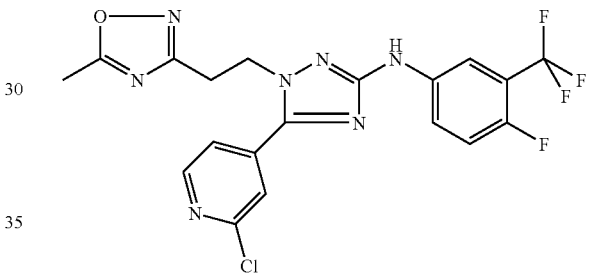

A mixture of compound 55 (0.00338 mol), acetylchloride (0.00338 mol) and DIPEA (0.0068 mol) in THF (40 ml) was stirred, then divided over 8 tubes. The reaction mixture was heated for 30 minutes at 150° C. in the microwave oven. The reaction mixture (8 tubes) were recombined. The solvent was evaporated. The residue was dissolved in CH$_2$Cl$_2$, washed with a 10% aqueous Na$_2$CO$_3$ solution, then dried (MgSO$_4$), filtered and the solvent was evaporated. The residue was purified over silica gel on a glass filter (eluent: CH$_2$Cl$_2$/CH$_3$OH 95/5). The product fractions were collected and the solvent was evaporated, yielding 1.2 g (75%) of compound 56.

Example B24 a) Preparation of Compound 57

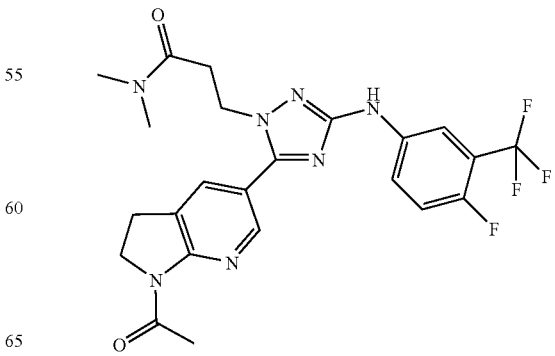

A mixture of

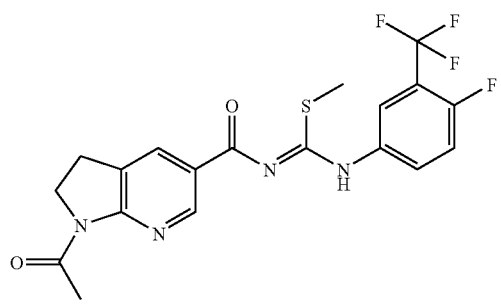

(0.00068 mol) and 3-hydrazino-N,N-dimethylpropanamide (0.00136 mol) in t-BuOH (50 ml) was stirred and refluxed for 2 hours. The solvent was evaporated and the residue was taken up in H$_2$O. This mixture was extracted with CH$_2$Cl$_2$. The separated organic layer was dried (MgSO$_4$), filtered and the solvent was evaporated. The residue was purified over silica gel on a glass filter (eluent: 1% CH$_3$OH in CH$_2$Cl$_2$ and then 2% CH$_3$OH in CH$_2$Cl$_2$. The pure fractions were collected and the solvent was evaporated, yielding 0.065 g of compound 57.

b) Preparation of Compound 58

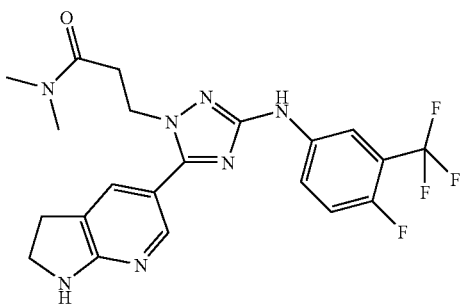

A mixture of compound 57 (0.0001 mol), K$_2$CO$_3$ (0.0007 mol), H$_2$O (1 ml) and CH$_3$OH (1 ml) was stirred at room temperature for 2 hours. The solvent was evaporated and CH$_3$OH (1 ml) was added and stirred for 2 hours at 70° C. The mixture was evaporated and 1 ml H$_2$O and CH$_2$Cl$_2$ were added. The mixture was filtered over an Extrelute filter and the filtrate was evaporated. The residue was purified by HPLC method A. The pure fractions were collected and the solvent was evaporated. The residue was dried, yielding 0.017 g (28%) of compound 58.

Example B25

Preparation of Compounds 59 and 60

Compound 59

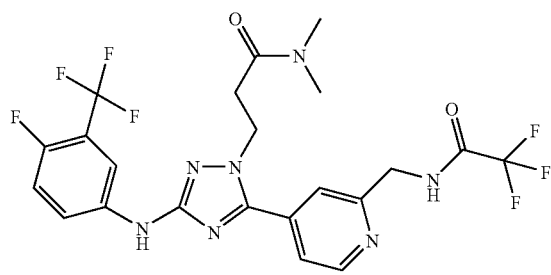

Compound 60

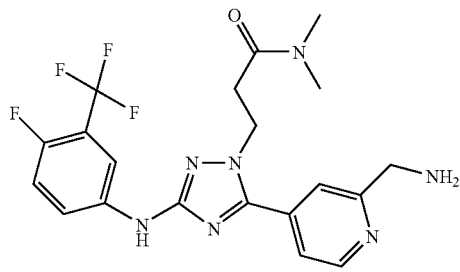

HBTU (0.00021 mol) was added to a solution of intermediate 36 (0.0001 mol) in N-methylmethanamine (5 ml; 5.6 M in ethanol). After 15 minutes, an extra amount of HBTU (0.00021 mol) was added. The mixture was evaporated to dryness and the residue was re-dissolved in a 10% Na$_2$CO$_3$ solution. This mixture was extracted with 3×50 ml CH$_2$Cl$_2$. The combined organic layers were dried (Na$_2$SO$_4$), filtered and evaporated to dryness. The residue was purified by HPLC method B, providing 2 fractions: Fraction 1 and Fraction 2. The solvent of Fraction 2 was evaporated yielding 0.0027 g (5%) of compound 59. Fraction 1 was recovered by an acid-base extraction with 1 N HCl, NaHCO$_3$ and CH$_2$Cl$_2$ as organic solvent. The re-extracted CH$_2$Cl$_2$ solution was dried (Na$_2$SO$_4$), filtered and the solvent was evaporated providing a white solid, yielding 0.0009 g (2%) of compound 60.

Example B26 a) Preparation of Compound 61

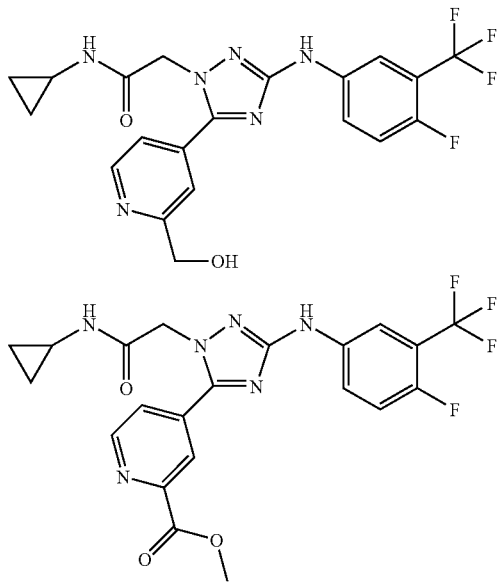

(0.0001 mol) was dissolved in CH$_3$OH/THF (1:1) (4 ml) and cooled to 0° C. CaCl$_2$.H$_2$O (0.0005 mol) was added, followed by NaBH$_4$ (0.0004 mol). The mixture was allowed to warm to room temperature. After 2 hours, a saturated NH$_4$Cl solution was added and the product was extracted into EtOAc (2×) and washed with brine, dried Na$_2$SO$_4$, filtered and the filtrate was evaporated. The residue was purified by Biotage 25M (eluent: CH$_2$Cl$_2$—10% CH$_3$OH/CH$_2$Cl$_2$). The product fractions were collected and the solvent was evaporated, yielding 0.012 g of compound 61.

b) Preparation of Compound 62

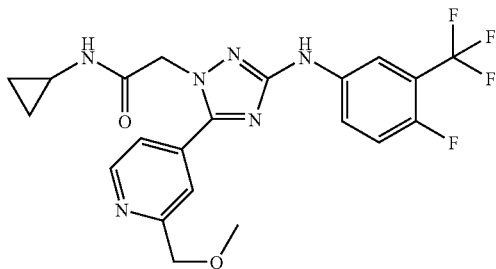

To a suspension of compound 61 (0.0004 mol) and Et₃N (0.0014 mol) in THF (4 ml) at room temperature was added methanesulfonyl chloride (0.0007 mol). The suspension dissolved and after 15 minutes 30% NaOCH₃ in CH₃OH (0.5 ml) was added dropwise, the color turned orange. The mixture was quenched with water and extracted with EtOAc (2×), the combined organic layers were washed with brine and dried (Na₂SO₄), filtered and the filtrate was evaporated. The residue was purified by HPLC method A. The product fractions were collected and the solvent was evaporated, yielding 90 mg of compound 62.

Example B27

Preparation of Compound 63

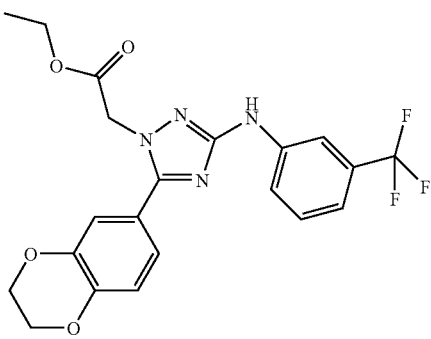

A mixture of intermediate 2 (0.0071 mol) and hydrazinoacetic acid ethyl ester monohydrochloride (0.0071 mol) in 2-methyl-2-propanol (100 ml) was stirred for 2 hours at reflux. The solvent was evaporated. The residue was purified by HPLC method A. The product fractions were collected and the solvent was evaporated, yielding 0.400 g of compound 63.

Example B28 a) Preparation of Compound 64

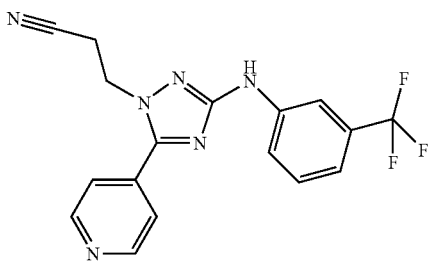

A mixture of intermediate 5 (0.03 mol) and 3-hydrazinopropanenitrile (0.03 mol) in ethanol (200 ml) was stirred at reflux for 2 hours. The solvent was evaporated. The residue was purified over silica gel by glass filter (eluent: CH₂Cl₂/CH₃OH 98/2, 97/3 and 96/4). The product fractions were collected and the solvent was evaporated. The residue was crystallized from CH₃CN. The precipitate was filtered off and dried, yielding 1.10 g (10%) of compound 64.

b) Preparation of Compound 65

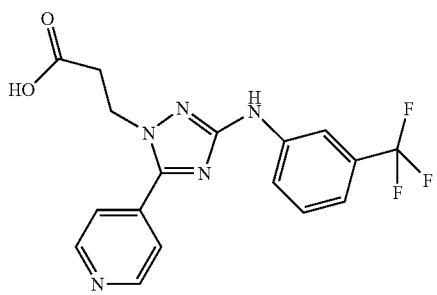

A mixture of compound 64 (0.0031 mol) in 6N HCl/2-propanol (25 ml) and HOAc (25 ml) was stirred at reflux for 4 hours. The solvent was evaporated. The residue was stirred in 2-propanol. The precipitate was filtered off and dried, yielding 1.09 g (85%) of compound 65 as a hydrochloric acid salt (.HCl).

Example B29 a) Preparation of Compound 66

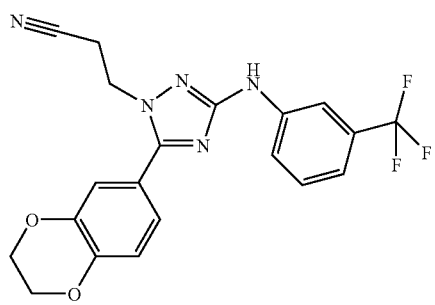

A mixture of intermediate 2 (0.00835 mol) and 3-hydrazinopropanenitrile (0.00835 mol) in ethanol (100 ml) was stirred and refluxed for 2 hours. The solvent was evaporated. The residue was purified by column chromatography over silica gel (eluent: CH₂Cl₂/CH₃OH 99/1 and 98/2). The product fractions were collected and the solvent was evaporated, yielding 3.44 g (99%) of compound 66.

b) Preparation of Compound 67

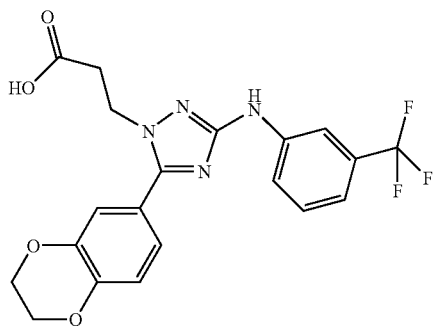

A mixture of compound 66 (0.0041 mol) in a 6N aqueous HCl solution (25 ml) and HOAc (25 ml) was stirred and refluxed for 4 hours. The solvent was evaporated. The residue was stirred in 2-propanone. The precipitate was filtered off and dried (product contains 2 mol NH₄Cl). The residue was taken up in H₂O and then neutralized with an aqueous NaHCO₃ solution to a pH of 7. The precipitate was filtered off and dried, yielding 0.435 g of compound 67.

Example B30

Preparation of Compound 68

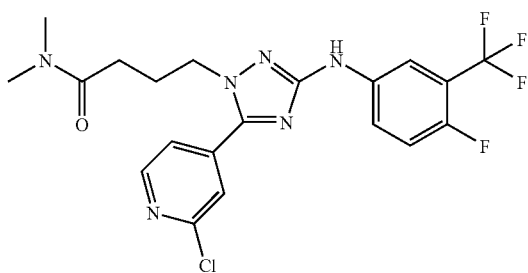

A mixture of intermediate 19 (0.0009 mol) in TFA (10 ml) and CH₃OH (0.5 ml) was stirred for 4 hours. Then the reaction mixture was poured out into a saturated NaHCO₃/ice solution with solid NaHCO₃. This mixture was extracted with EtOAc (2×). The separated organic layer was washed with a saturated NaHCO₃ solution and brine, dried (Na₂SO₄), filtered and the solvent was evaporated. The residue was purified over a Biotage 25 M column (eluent: CH₂Cl₂–5% CH₃OH/CH₂Cl₂). The product fractions were collected and the solvent was evaporated, yielding 0.4 g of compound 68.

Example B31

Preparation of Compound 33

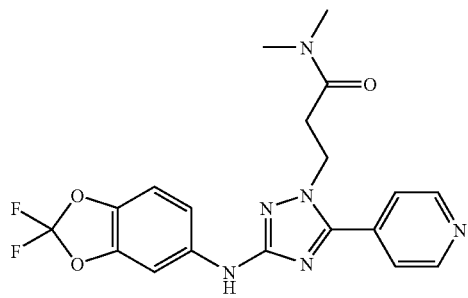

A mixture of intermediate 26 (0.0110 mol) and Et₃N in THF was hydrogenated with 10% Pd/C as a catalyst in the presence of a thiophene solution (1 ml; 4% in DIPE). After uptake of H₂ (1 equiv.), the catalyst was filtered off and the filtrate was concentrated by evaporation. The residue was dissolved in CH₂Cl₂, washed with water. The organic layer was separated, dried over MgSO₄, filtered, and the filtrate was concentrated by evaporation. The residue was crystallised from CH₃OH, filtered off and dried, yielding 3.13 g (68%) compound 33.

Example B32

Preparation of Compound 39

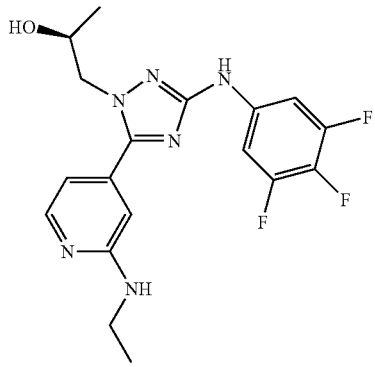

Reaction at 140° C. over 32 hours. A mixture of intermediate 29 (0.0123 mol) and ethanamine (10 g) in ethanol (50 ml) was concentrated by evaporation. The residue was purified by silica column chromatography (eluent: CH₂Cl₂+5% CH₃OH). The product fraction was collected and concentrated by evaporation. The residue was crystallised from CH₃CN, filtered off and dried, yielding 2.971 g (60%) of compound 39.

Example B33

Preparation of Compound 45

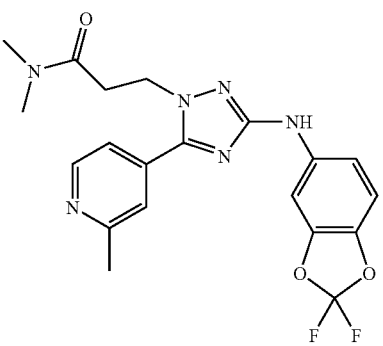

Intermediate 26 (0.0130 mol) was dissolved in THF (75 ml), 1-methyl-2-pyrrolidinone (15 ml) was added, iron(III) acetylacetonate (0.0013 mol) was added under N₂ and the resulting mixture was cooled on a ice bath. CH₃MgBr (0.0520 mol, 3M in Et₂O) was slowly added. After 10 minutes, CH₃OH (30 ml) was added dropwise. The reaction mixture was stirred for 15 minutes, then concentrated by evaporation. The residue was dissolved in CH₂Cl₂, washed with water, filtered over decalite. The organic layer was dried (MgSO₄), filtered, then concentrated by evaporation. The residue was purified by silica column chromatography (eluent: from CH₂Cl₂ to CH₂Cl₂+5% CH₃OH). The product fraction was concentrated by evaporation. The residue was crystallised from CH₃OH, filtered off and dried, yielding 0.843 g of compound 45.

Compound 44 was prepared in a similar manner as described in Example B33 starting from an intermediate prepared according to Scheme 13.

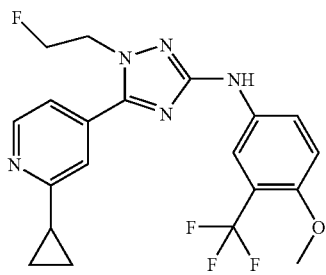

Example B34

Preparation of Compound 46

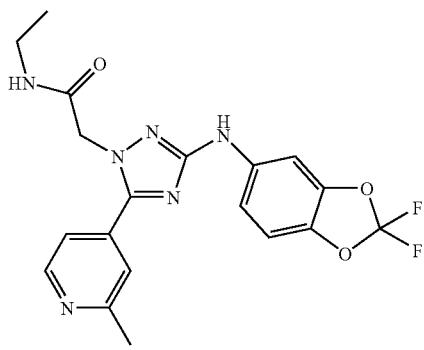

A solution of intermediate 31 (0.0113 mol) and iron (III) acetylacetonate (0.0011 mol) in 1-methyl-2-pyrrolidinone (8 ml) and THF (120 ml) was cooled in an ice-bath under a nitrogen atmosphere. $CH_3MgBr$ (22 ml) was added very slowly (exothermic reaction), such that the internal temperature did not exceed 8° C. The brown mixture was quenched with ca. 6 ml $CH_3OH$ while cooling on an ice bath. Then a saturated $NH_4Cl$ solution was added and the mixture was extracted with EtOH (3×). The aqueous phase was made alkaline with 1 N NaOH (pH approx 10) and extracted with EtOAc (2×). The combined EtOAc fractions were washed with diluted 1 N NaOH (pH approx 10) and brine. After evaporation of the organic solvent, the residue was crystallized from EtOH and a small amount of THF. The precipitate was filtered off and dried (0.916 g). The residue was purified by HPLC method B. During evaporation of the solvent, the material crystallized. The product was filtered off, washed with EtOH and DIPE, yielding compound 46 as a white solid.

Example B35

Preparation of Compound 26

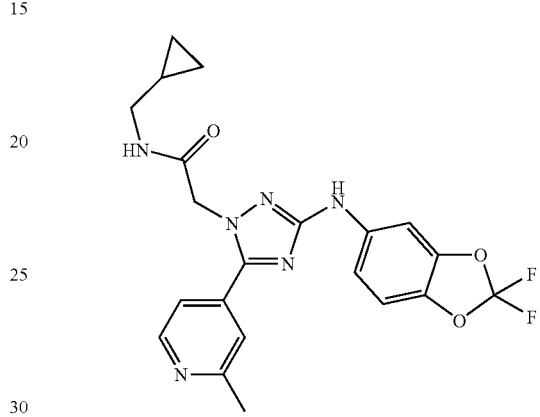

A mixture of intermediate 35 (0.0004 mol), cyclopropanemethanamine, hydrochloride (1:1) (0.0008 mol), HOBt (0.0012 mol), EDCI (0.0012 mol) and DIPEA (0.002 mol) in DMF (3 ml) was stirred overnight at room temperature. Then the reaction mixture was poured into $H_2O$ and the mixture was extracted with $CH_2Cl_2$. The separated organic layer was washed with 1N NaOH-solution, dried ($MgSO_4$), filtered and the solvent was evaporated. The residue was crystallized from $CH_2Cl_2$. The crystals were filtered off and dried, yielding 0.067 g (39%) of compound 26.

Tables 1 to 5 list all the compounds that were prepared according to the general schemes and the exemplified procedures above. The column 'Prep' indicates the general scheme numbers and certain compound numbers according to which the respective compound was prepared. Said column also indicates the salt form of the respective compound.

TABLE 1

Compounds prepared according to the Examples.

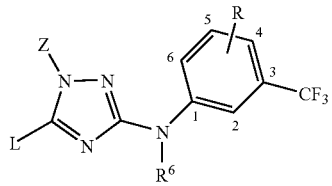

| Co. nr. | Prep. | L | Z | ----R | ----$R^6$ |
|---|---|---|---|---|---|
| 16 | 0, 1 | (3-pyridyl) | HO~~~ | — | ----H |

TABLE 1-continued

Compounds prepared according to the Examples.

| Co. nr. | Prep. | L | Z | ----R | ----R⁶ |
|---|---|---|---|---|---|
| 2 | 0, 1 | pyridin-4-yl | HO-CH₂CH₂- | — | ----H |
| 70 | 0, 1, 7 | 2-ethylpyridin-4-yl | HO-CH₂CH₂- | — | ----H |
| 71 | 0, 1, 7 | 6-isopropylpyridin-3-yl | HO-CH₂CH₂- | — | ----H |
| 7 | 0, 1 | 2-chloropyridin-4-yl | HO-CH₂CH₂- | — | ----H |
| 72 | 0, 1, 8 | 6-methoxypyridin-3-yl | HO-CH₂CH₂- | — | ----H |
| 73 | 0, 1, 8 | 2-methoxypyridin-4-yl | HO-CH₂CH₂- | — | ----H |
| 74 | 0, 1, 8 | 2-isopropoxypyridin-4-yl | HO-CH₂CH₂- | — | ----H |
| 75 | 0, 1, 5a | 2-(dimethylamino)pyridin-4-yl | HO-CH₂CH₂- | — | ----H |

TABLE 1-continued
Compounds prepared according to the Examples.
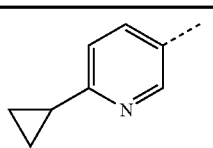
| Co. nr. | Prep. | L | Z | ----R | ----R$^6$ |
|---|---|---|---|---|---|
| 76 | 0, 1, 7 | 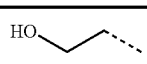 | 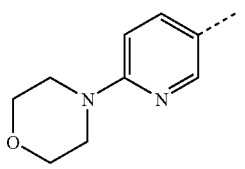 | — | ----H |
| 77 | 0, 1, 5a | 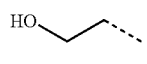 | 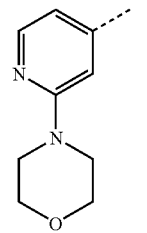 | — | ----H |
| 38 | 0, 1, 5a | 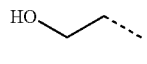 | 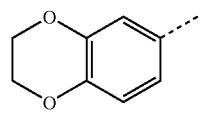 | — | ----H |
| 3 | 0, 1 | 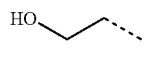 | 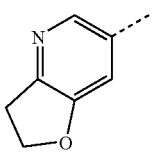 | — | ----H |
| 78 | 0, 1, 6 | 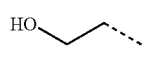 | 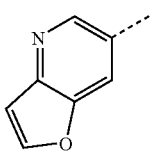 | — | ----H |
| 79 | 0, 1 | 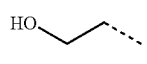 | 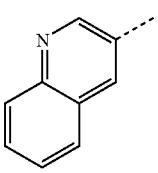 | — | ----H |
| 80 | 0, 1 | 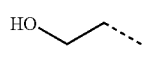 | 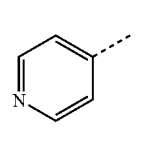 | — | ----H |
| 52 | 0, 1, 24 | 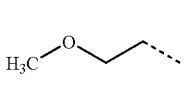 | H$_3$C$\diagup$O$\diagdown$ | — | ----H |

TABLE 1-continued
Compounds prepared according to the Examples.
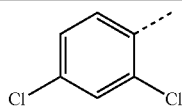
| Co. nr. | Prep. | L | Z | ----R | ----R⁶ |
|---|---|---|---|---|---|
| 20 | 0, 1, 2 | 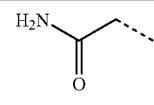 | 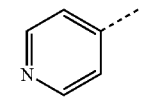 | — | ----H |
| 19 | 0, 1, 2 | 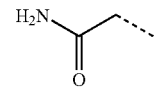 | 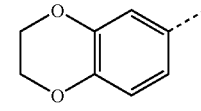 | — | ----H |
| 21 | 0, 1, 2 | 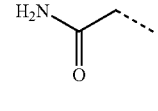 | 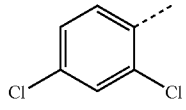 | — | ----H |
| 13 | 0, 1 | 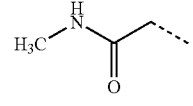 | 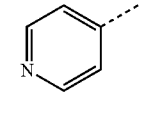 | — | ----H |
| 9 | 0, 1, 2 | 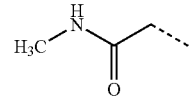 | 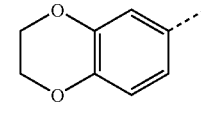 | — | ----H |
| 1 | 0, 1, 2 | 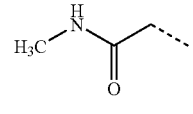 | 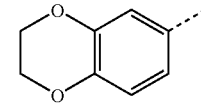 | — | ----H |
| 5 | 0, 1, 2 | 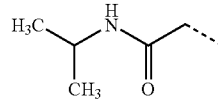 | 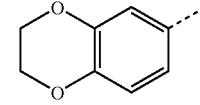 | — | ----H |
| 23 | 0, 1, 2 | 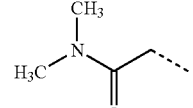 | 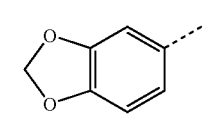 | — | ----H |
| 81 | 0, 1 | 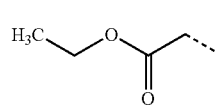 | 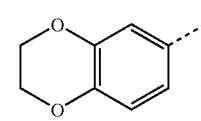 | — | ----H |
| 63 | 0, 1 | 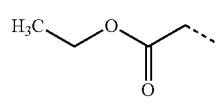 | 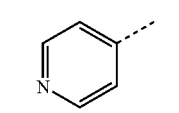 | — | ----H |
| 24 | 0, 1, 2 | 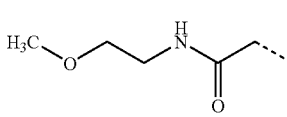 |  | — | ----H |

TABLE 1-continued
Compounds prepared according to the Examples.
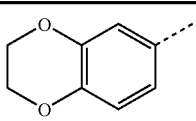
| Co. nr. | Prep. | L | Z | ----R | ----R$^6$ |
|---|---|---|---|---|---|
| 82 | 0, 1, 2 | 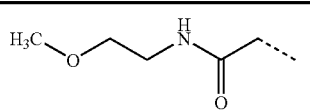 | 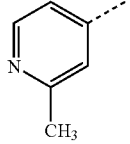 | — | ----H |
| 47 | 0, 1, 26 | 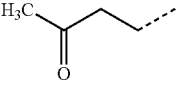 | 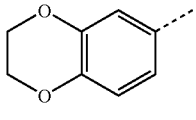 | — | ----H |
| 10 | 0, 1, 2 | 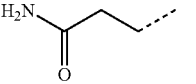 | 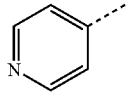 | — | ----H |
| 11 | 0, 1, 2 | 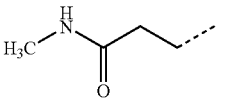 | 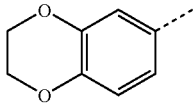 | — | ----H |
| 12 | 0, 1, 2 | 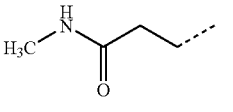 | 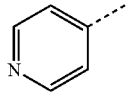 | — | ----H |
| 4 | 0, 1, 2 | 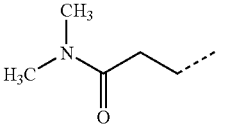 | 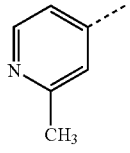 | — | ----H |
| 48 | 0, 1, 7 | 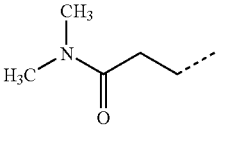 | 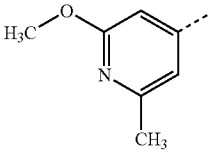 | — | ----H |
| 83 | 0, 1, 7 | 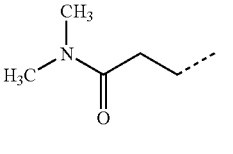 | 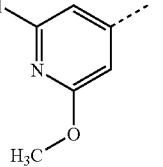 | — | ----H |
| 84 | 0, 1 | 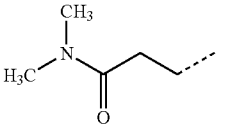 |  | — | ----H |

TABLE 1-continued
Compounds prepared according to the Examples.
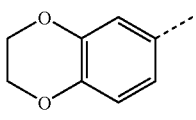
| Co. nr. | Prep. | L | Z | ----R | ----R⁶ |
|---|---|---|---|---|---|
| 6 | 0, 1, 2 | 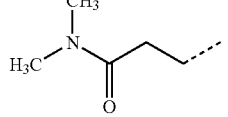 | 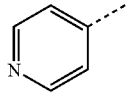 | — | ----H |
| 22 | 0, 1, 2 | 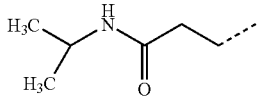 | 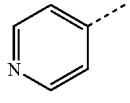 | — | ----H |
| 65 | 0, 1 •HCl | 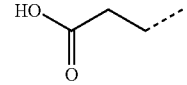 | 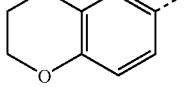 | — | ----H |
| 67 | 0, 1 | 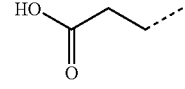 | 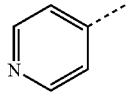 | — | ----H |
| 64 | 0, 1 | 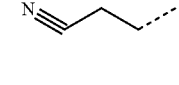 | 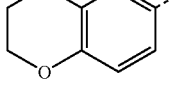 | — | ----H |
| 66 | 0, 1 |  | 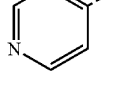 | — | ----H |
| 85 | 0, 1, 2 | 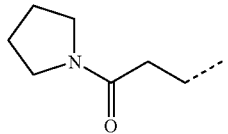 | 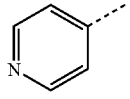 | — | ----H |
| 86 | 0, 1, 2 0.5 HCl | 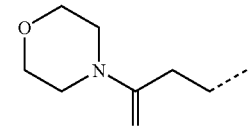 | 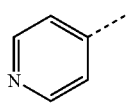 | — | ----H |
| 8 | 0, 1, 3 | 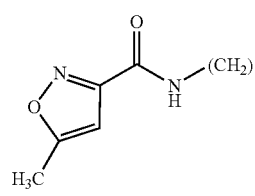 | 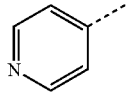 | — | ----H |
| 87 | 0, 1 |  | HO⁀⁀⁀ | 4-F | ----H |

TABLE 1-continued

Compounds prepared according to the Examples.

| Co. nr. | Prep. | L | Z | ----R | ----R⁶ |
|---|---|---|---|---|---|
| 88 | 0, 1, 7 | 2-ethyl-pyridin-4-yl | HO-CH₂CH₂- | 4-F | ----H |
| 89 | 0, 1 | 3-fluoro-pyridin-4-yl | HO-CH₂CH₂- | 4-F | ----H |
| 90 | 0, 1, 8 | 2-methoxy-pyridin-4-yl | HO-CH₂CH₂- | 4-F | ----H |
| 91 | 0, 1, 8 | 6-ethoxy-pyridin-3-yl | HO-CH₂CH₂- | 4-F | ----H |
| 92 | 0, 1, 5 | 6-(methylamino)-pyridin-3-yl | HO-CH₂CH₂- | 4-F | ----H |
| 93 | 0, 1, 5 | 6-(2-methoxyethylamino)-pyridin-3-yl | HO-CH₂CH₂- | 4-F | ----H |
| 94 | 0, 1, 7 | 6-cyclopropyl-pyridin-3-yl | HO-CH₂CH₂- | 4-F | ----H |
| 95 | 0, 1, 5 | 6-(cyclopropylamino)-pyridin-3-yl | HO-CH₂CH₂- | 4-F | ----H |

TABLE 1-continued
Compounds prepared according to the Examples.
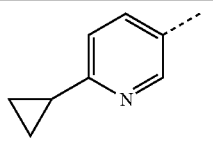
| Co. nr. | Prep. | L | Z | ----R | ----R⁶ |
|---|---|---|---|---|---|
| 96 | 0, 1, 7, 13 | 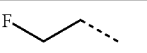 | 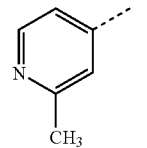 | 4-F | ----H |
| 25 | 0, 1, 7 | 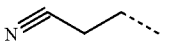 | 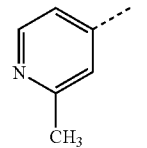 | 4-F | ----H |
| 97 | 0, 1, 7 | 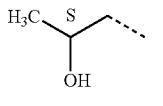 | 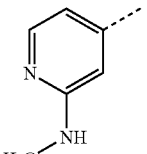 | 4-F | ----H |
| 98 | 0, 1, 5 | 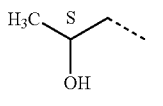 | 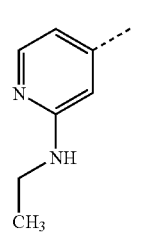 | 4-F | ----H |
| 99 | 0, 1, 5 | 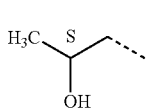 | 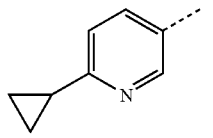 | 4-F | ----H |
| 100 | 0, 1, 7 •HCl•H₂O | 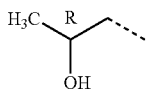 | 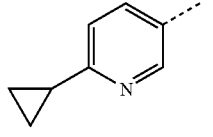 | 4-F | ----H |
| 101 | 0, 1, 7 | 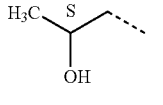 | 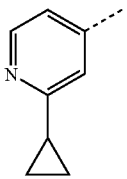 | 4-F | ----H |
| 102 | 0, 1, 7 | 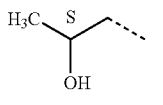 | | 4-F | ----H |

TABLE 1-continued

Compounds prepared according to the Examples.

| Co. nr. | Prep. | L | Z | ----R | ----R⁶ |
|---|---|---|---|---|---|
| 103 | 0, 1, 5a | pyridin-4-yl-2-NH-cyclopropyl | H₃C-CH(SH)-CH(OH)- *(2-methylthio-1-hydroxypropyl)* | 4-F | ----H |
| 104 | 0, 1, 5 | pyridin-4-yl-2-NH-CH₂-cyclopropyl | H₃C-CH(S)-CH(OH)- | 4-F | ----H |
| 105 | 0, 1, 6 | 2,3-dihydrofuro[3,2-b]pyridin-6-yl | H₃C-CH(S)-CH(OH)- | 4-F | ----H |
| 106 | 0, 1 | furo[3,2-b]pyridin-6-yl | H₃C-CH(S)-CH(OH)- | 4-F | ----H |
| 34 | 0, 1, 2, 8 •HCl | 6-ethoxypyridin-3-yl | HOOC-CH₂- | 4-F | ----H |
| 107 | 0, 1, 2, 7 | 2-methylpyridin-4-yl | H₃C-NH-C(O)-CH₂- | 4-F | ----H |
| 108 | 0, 1, 2, 7 | 6-methylpyridin-3-yl | H₃C-NH-C(O)-CH₂- | 4-F | ----H |
| 109 | 0, 1, 2, 8 | 3-methoxypyridin-4-yl | H₃C-NH-C(O)-CH₂- | 4-F | ----H |

TABLE 1-continued

Compounds prepared according to the Examples.

| Co. nr. | Prep. | L | Z | ----R | ----R⁶ |
|---|---|---|---|---|---|
| 110 | 0, 1, 2, 8 | 6-methoxypyridin-3-yl | N-methylacetamide | 4-F | ----H |
| 111 | 0, 1, 2, 8 | 6-ethoxypyridin-3-yl | N-methylacetamide | 4-F | ----H |
| 112 | 0, 1, 2, 5 | 2-(methylamino)pyridin-4-yl | N-methylacetamide | 4-F | ----H |
| 113 | 0, 1, 2, 5 | 6-(methylamino)pyridin-3-yl | N-methylacetamide | 4-F | ----H |
| 114 | 0, 1, 2, 5 | 3-(methylamino)pyridin-4-yl | N-methylacetamide | 4-F | ----H |
| 115 | 0, 1, 2 | 6-(2-methoxyethylamino)pyridin-3-yl | N-methylacetamide | 4-F | ----H |
| 116 | 0, 1, 2 | 3-fluoropyridin-4-yl | N-methylacetamide | 4-F | ----H |
| 117 | 0, 1, 2 | 3-chloropyridin-4-yl | N-methylacetamide | 4-F | ----H |

TABLE 1-continued
Compounds prepared according to the Examples.
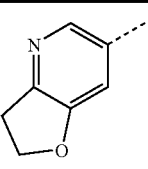
| Co. nr. | Prep. | L | Z | ----R | ----R⁶ |
|---|---|---|---|---|---|
| 28 | 0, 1, 2, 6 | 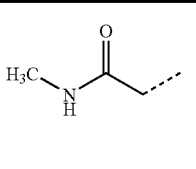 | 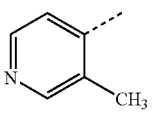 | 4-F | ----H |
| 118 | 0, 1, 2 | 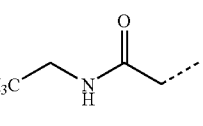 | 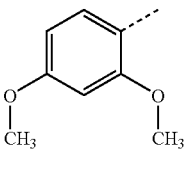 | 4-F | ----H |
| 119 | 0, 1, 2 | 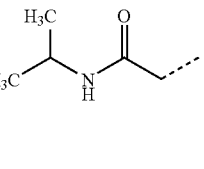 | 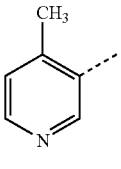 | 4-F | ----H |
| 120 | 0, 1, 2 | 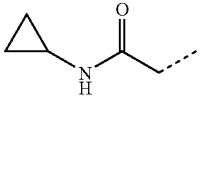 | 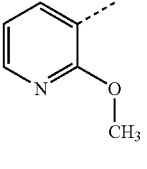 | 4-F | ----H |
| 121 | 0, 1, 2 | 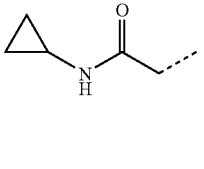 | 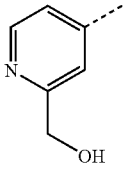 | 4-F | ----H |
| 61 | 0, 1, 2, 14, B26a | 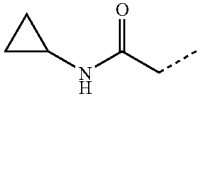 | 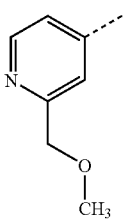 | 4-F | ----H |
| 62 | 0, 1, 2, 14, B26a, B26b | 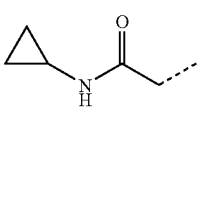 | | 4-F | ----H |

TABLE 1-continued

Compounds prepared according to the Examples.

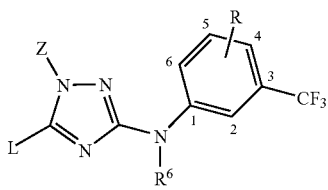

| Co. nr. | Prep. | L | Z | ----R | ----R⁶ |
|---|---|---|---|---|---|
| 122 | 0, 1, 14, 27 | 2-(2-hydroxypropan-2-yl)pyridin-4-yl | N-cyclopropylpropanamide | 4-F | ----H |
| 123 | 0, 1, 14, 27 | 2-acetylpyridin-4-yl | N-cyclopropylpropanamide | 4-F | ----H |
| 124 | 0, 1, 2, 7 | 2-methylpyridin-4-yl | 1-(pyrrolidin-1-yl)propan-1-one | 4-F | ----H |
| 32 | 0, 1, 12 | pyridin-4-yl | propanoic acid | 4-F | ----H |
| 31 | 0, 1 | 2-chloropyridin-4-yl | propanoic acid | 4-F | ----H |
| 30 | 0, 1, 2, 21 | 2-(aminomethyl)pyridin-4-yl | tert-butyl butanoate | 4-F | ----H |
| 29 | 0, 1, 2, 21 | 2-cyanopyridin-4-yl | tert-butyl butanoate | 4-F | ----H |
| 125 | 0, 1, 12 | pyridin-3-yl | N,N-dimethylpropanamide | 4-F | ----H |

TABLE 1-continued
Compounds prepared according to the Examples.
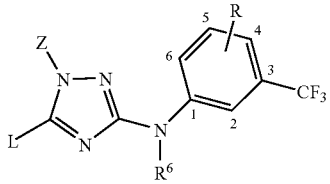
| Co. nr. | Prep. | L | Z | ----R | ----R$^6$ |
|---|---|---|---|---|---|
| 126 | 0, 1 | 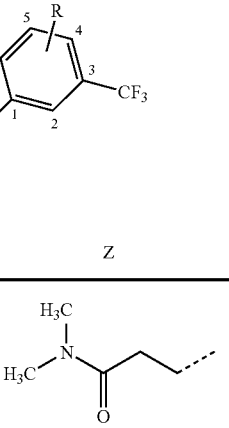 | 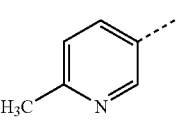 | 4-F | ----H |
| 127 | 0, 1, 7 | 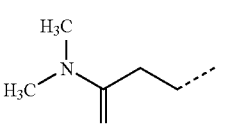 | 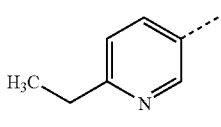 | 4-F | ----H |
| 128 | 0, 1, 7 | 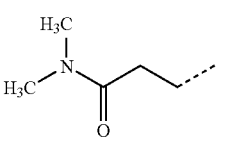 | 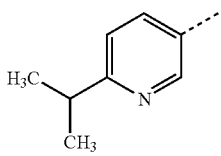 | 4-F | ----H |
| 129 | 0, 1, 7 | 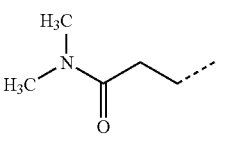 | 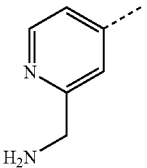 | 4-F | ----H |
| 600 | 0, 1, 2, 21 | 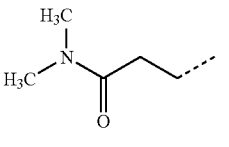 | 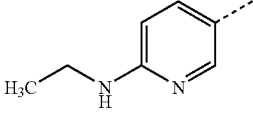 | 4-F | ----H |
| 130 | 0, 1, 5 | 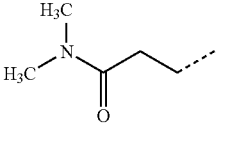 | 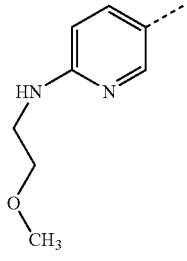 | 4-F | ----H |
| 131 | 0, 1, 5 | 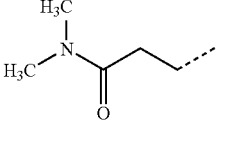 | | 4-F | ----H |

TABLE 1-continued
Compounds prepared according to the Examples.
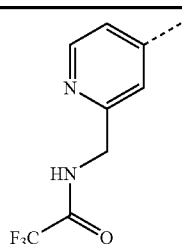
| Co. nr. | Prep. | L | Z | ----R | ----R⁶ |
|---|---|---|---|---|---|
| 59 | 0, 1, 2, 21, 22 | 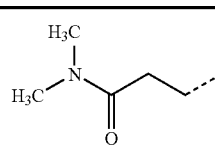 | 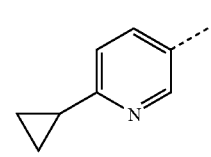 | 4-F | ----H |
| 132 | 0, 1, 7 | 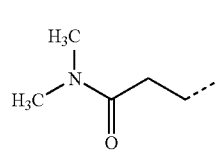 | 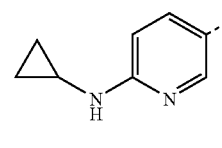 | 4-F | ----H |
| 133 | 0, 1, 5 | 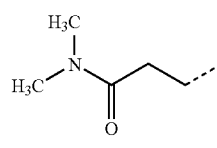 | 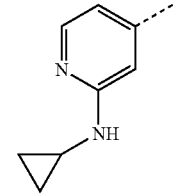 | 4-F | ----H |
| 134 | 0, 1, 5 | 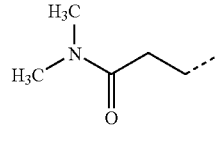 | 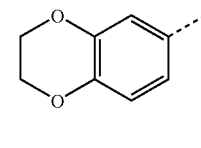 | 4-F | ----H |
| 135 | 0, 1 | 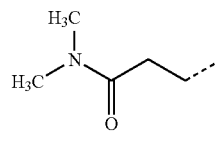 | 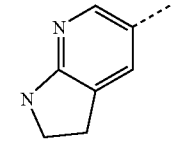 | 4-F | ----CH₃ |
| 58 | 0, 1, 10, 11 | 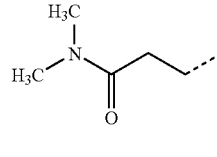 | 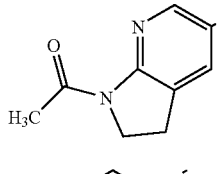 | 4-F | ----H |
| 57 | 0, 1, 10 | 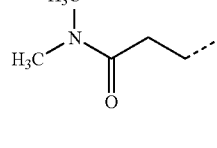 | 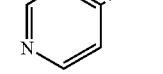 | 4-F | ----H |
| 136 | 25, 0, 1 | 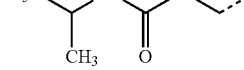 |  | 4-F | ----H |

TABLE 1-continued

Compounds prepared according to the Examples.

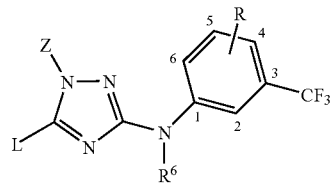

| Co. nr. | Prep. | L | Z | ----R | ----R⁶ |
|---|---|---|---|---|---|
| 137 | 0, 1 | 4-pyridyl | H₃C-C(CH₃)₂-NH-C(O)-CH₂- | 4-F | ----H |
| 53 | 0, 1, 12, 20 | 4-pyridyl | H₂N-C(CH₃)=N-O-C(O)-CH₂- | 4-F | ----H |
| 43 | 16, 17, 1, 2, 18, 7 | 2-methyl-4-pyridyl | H₃C-C(O)-(CH₂)₃- | 4-F | ----H |
| 42 | 16, 17, 1, 2, 18, 7 | 2-methyl-4-pyridyl | (CH₃)₂N-C(O)-(CH₂)₃- | 4-F | ----H |
| 68 | 16, 17, 1, 2, 18 | 2-chloro-4-pyridyl | (CH₃)₂N-C(O)-(CH₂)₃- | 4-F | ----H |
| 138 | 0, 1, 23, 12 | 4-pyridyl | H₃C-C(O)-NH-CH₂- | 4-F | ----H |
| 139 | 0, 1, 23, 7 | 2-methyl-4-pyridyl | H₃C-CH₂-O-C(O)-NH-CH₂- | 4-F | ----H |
| 140 | 0, 1, 23, 7 | 2-cyclopropyl-4-pyridyl | H₃C-CH₂-O-C(O)-NH-CH₂- | 4-F | ----H |
| 54 | 0, 1, 23 | 2-chloro-4-pyridyl | 5-methyl-isoxazol-3-yl-C(O)-NH-CH₂- | 4-F | ----H |

TABLE 1-continued

Compounds prepared according to the Examples.

| Co. nr. | Prep. | L | Z | ----R | ----R⁶ |
|---|---|---|---|---|---|
| 27 | 0, 1, 7, 3 | 2-methyl-pyridin-4-yl | H₃C-C(O)-NH-(CH₂)₃- | 4-F | ----H |
| 55 | 0, 1, 19 | 2-chloro-pyridin-4-yl | H₂N-C(=N-OH)-CH₂CH₂- (mixture of E/Z) | 4-F | ----H |
| 69 | 0, 1, 12, 20 | pyridin-4-yl | 3-methyl-1,2,4-oxadiazol-5-yl-CH₂CH₂- | 4-F | ----H |
| 141 | 0, 1, 19, 12a | pyridin-4-yl | 5-methyl-1,2,4-oxadiazol-3-yl-CH₂CH₂- | 4-F | ----H |
| 37 | 0, 1, 19, 5 | 2-(methylamino)-pyridin-4-yl | 5-methyl-1,2,4-oxadiazol-3-yl-CH₂CH₂- | 4-F | ----H |
| 56 | 0, 1, 19 | 2-chloro-pyridin-4-yl | 5-methyl-1,2,4-oxadiazol-3-yl-CH₂CH₂- | 4-F | ----H |
| 142 | 0, 1, 2 | 4-methoxy-3-benzyloxy-phenyl | H₃C-CH₂-NH-C(O)-CH₂- | 5-Br | ----H |

TABLE 1-continued

Compounds prepared according to the Examples.

| Co. nr. | Prep. | L | Z | ----R | ----R⁶ |
|---|---|---|---|---|---|
| 143 | 0, 1 | pyridin-4-yl | HO-CH₂CH₂CH₂- | 4-OCH₃ | ----H |
| 44 | 0, 1, 13, 7 | 2-cyclopropylpyridin-4-yl | F-CH₂CH₂CH₂- | 4-OCH₃ | ----H |
| 144 | 0, 1, 7 | 2-methylpyridin-4-yl | (CH₃)₂N-C(O)-CH₂CH₂- | 4-OCH₃ | ----H |
| 145 | 0, 1 | 3-chloropyridin-4-yl | (CH₃)₂N-C(O)-CH₂CH₂- | 4-OCH₃ | ----H |
| 146 | 0, 1, 2, 5 | 2-(methylamino)pyridin-4-yl | CH₃NH-C(O)-CH₂- | 5-OCH₃ | ----H |
| 147 | 0, 1, 2 | 2-(2-hydroxyethylamino)pyridin-4-yl | HO-CH₂CH₂-NH-C(O)-CH₂- | 5-OCH₃ | ----H |

TABLE 2

Compounds prepared according to the Examples.

| Co. nr. | Prep. | L | Z |
|---|---|---|---|
| 148 | 0, 1, 7 | 2-methyl-pyridin-4-yl | H3C-CH(OH)- (S) |
| 149 | 0, 1, 5 | 4-(ethylamino)pyridin-3-yl | H3C-CH(OH)- (S) |
| 150 | 0, 1, 7 | 6-cyclopropyl-pyridin-3-yl | H3C-CH(OH)- (S) |
| 151 | 0, 1, 7 ·HCl | 2-cyclopropyl-pyridin-4-yl | H3C-CH(OH)- (R) |
| 152 | 0, 1, 13, 7 | 2-cyclopropyl-pyridin-4-yl | F-CH2-CH2- |
| 153 | 0, 1, 2, 5 | 4-(methylamino)pyridin-3-yl | H3C-NH-C(O)-CH2- |
| 154 | 0, 1, 2 | 3-fluoropyridin-4-yl | H3C-NH-C(O)-CH2- |
| 155 | 0, 1, 2, 7 | 6-cyclopropyl-pyridin-3-yl | H3C-NH-C(O)-CH2- |
| 156 | 0, 1, 2 | 2,3-dihydro-1,4-benzodioxin-6-yl | H3C-NH-C(O)-CH2- |
| 157 | 0, 1, 2 | 4-methyl-3,4-dihydro-2H-1,4-benzoxazin-7-yl | H3C-NH-C(O)-CH2- |
| 158 | 0, 1, 2 | 2,3-dihydro-1,4-benzodioxin-6-yl | H3C-CH2-NH-C(O)-CH2- |
| 159 | 0, 1, 2 | 3,4-dimethoxyphenyl | (CH3)2CH-NH-C(O)-CH2- |
| 160 | 0, 1, 2 | 4-methyl-3,4-dihydro-2H-1,4-benzoxazin-7-yl | (CH3)2CH-NH-C(O)-CH2- |
| 161 | 0, 1, 2 | 2,3-dihydro-1,4-benzodioxin-6-yl | (CH3)2N-CH2-CH2-NH-C(O)-CH2- |
| 162 | 0, 1, 2 | 3-methoxyphenyl | cyclopropyl-NH-C(O)-CH2- |
| 163 | 0, 1, 2 | 3,4-dimethoxyphenyl | cyclopropyl-NH-C(O)-CH2- |

TABLE 2-continued
Compounds prepared according to the Examples.
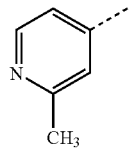
| Co. nr. | Prep. | L | Z |
|---|---|---|---|
| 164 | 0, 1, 2, 7 | 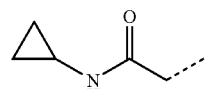 | 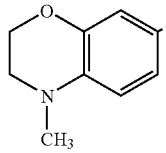 |
| 165 | 0, 1, 2 | 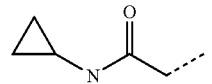 | 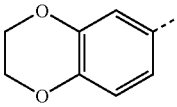 |
| 166 | 0, 1, 2 | 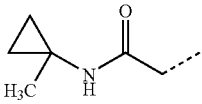 | 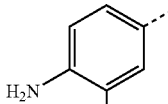 |
| 167 | 0, 1, 9 | 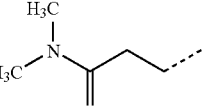 | 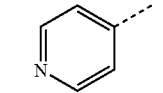 |
| 168 | 0, 1, 12 | 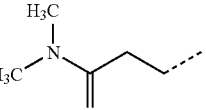 | 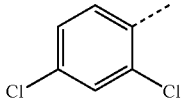 |
TABLE 3
Compounds prepared according to the Examples.
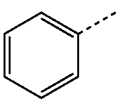
| Co. nr. | Prep. | L | Z | R |
|---|---|---|---|---|
| 18 | 0, 1 | 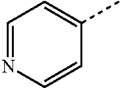 | —CH$_3$ | — |
| 17 | 0, 1 | 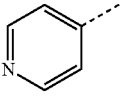 | HO\_\_\_ | 2-Cl, 5-Cl |
| 14 | 0, 1 | 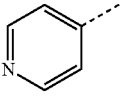 | HO\_\_\_ | 2-Cl, 5-Cl |
| 15 | 0, 1 | 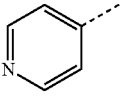 | HO\_\_\_ | 2-OCH$_3$, 4-OCH$_3$, 5-Cl |
| 169 | 0, 1, 7 | 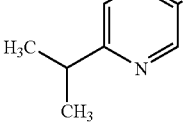 | HO\_\_\_ | 4-F |

TABLE 3-continued

Compounds prepared according to the Examples.

| Co. nr. | Prep. | L | Z | R |
|---|---|---|---|---|
| 170 | 0, 1, 8 | 6-ethoxypyridin-3-yl | 3-hydroxypropyl | 4-F |
| 171 | 0, 1, 7 | 6-cyclopropylpyridin-3-yl | 3-hydroxypropyl | 4-F |
| 49 | 0, 1, 14, 27 | 6-(2-hydroxypropan-2-yl)pyridin-3-yl | 1-(methylthio)propan-2-ol | 3-F, 4-F |
| 39 | 0, 1, 5 | 2-(ethylamino)pyridin-4-yl | 1-(methylthio)propan-2-ol | 3-F, 4-F, 5-F |
| 50 | 0, 1, 4, 27 | 6-acetylpyridin-3-yl | 1-(methylthio)propan-2-ol | 3-F, 4-F |
| 41 | 0, 1, 14, 15 | N-methylpyridazine-3-carboxamid-6-yl | 1-(methylthio)propan-2-ol | 3-F, 4-F |
| 40 | 0, 1, 14 | methyl pyridine-2-carboxylate-5-yl | 1-(methylthio)propan-2-ol | 3-F, 4-F |
| 172 | 0, 1 | 6-chloro-2-methylpyridin-4-yl | 1-(methylthio)propan-2-ol | 3-F, 4-F, 5-F |

TABLE 3-continued

Compounds prepared according to the Examples.

| Co. nr. | Prep. | L | Z | R |
|---|---|---|---|---|
| 173 | 0, 1, 5a | 4-(cyclopropylamino)pyridin-2-yl | H3C-S-CH(OH)- | 3-F, 4-F, 5-F |
| 174 | 0, 1, 14, 15 | 6-(pyrrolidin-1-ylcarbonyl)pyridin-3-yl | H3C-S-CH(OH)- | 3-F, 4-F |
| 175 | 0, 1, 7 | 2-cyclopropylpyridin-4-yl | H3C-S-CH(OH)- | 3-F, 4-F |
| 176 | A2, 0, 1, 5a | 2-(ethylamino)pyridin-4-yl | F3C-CH(OH)- (R) | 3-F, 4-F |
| 177 | 0, 1, 13, 7 | 2-cyclopropylpyridin-4-yl | F-CH2CH2- | 3-F, 5-F |
| 178 | 0, 1, 2, 5 | 2-(methylamino)pyridin-4-yl | H3C-NH-C(O)-CH2- | 3-F, 5-F |
| 36 | 0, 1, 2, 5, 4 | 2-(methylamino)pyridin-4-yl | H3C-NH-C(O)-CH2- | 3-F, 4-F, 5-F |

TABLE 3-continued

Compounds prepared according to the Examples.

| Co. nr. | Prep. | L | Z | R |
|---|---|---|---|---|
| 35 | 0, 1, 2, 5, 4 | 2-(N-methylamino)pyridin-4-yl | -CH2-C(=O)-NH-CH3 | 3-NHCH3, 4-F, 5-F |
| 179 | 0, 1, 7, 2 | 2-cyclopropylpyridin-4-yl | -CH2-C(=O)-NH-CH3 | 3-F, 5-F |
| 180 | 0, 1, 2, 5 | 2-(N-ethylamino)pyridin-4-yl | -CH2-C(=O)-NH-CH2CH3 | 3-F, 4-F, 5-F |
| 181 | 0, 1, 2, 5, 4 | 2-(N-ethylamino)pyridin-4-yl | -CH2-C(=O)-NH-CH2CH3 | 3-NH(CH2CH3), 4-F, 5-F |
| 182 | 0, 1 | pyridin-4-yl | -CH2CH2-C(=O)-N(CH3)2 | 4-OCH3 |
| 183 | 0, 1 | pyridin-4-yl | -CH2CH2-C(=O)-N(CH3)2 | 3-CN |
| 184 | 0, 1, 7 | 2-methylpyridin-4-yl | -CH2CH2-C(=O)-N(CH3)2 | 3-CH3, 4-F |

TABLE 3-continued

Compounds prepared according to the Examples.

| Co. nr. | Prep. | L | Z | R |
|---|---|---|---|---|
| 185 | 0, 1, 7 | 2-methyl-pyridin-4-yl | N,N-dimethylpropanamide | 3-F, 4-F |
| 186 | 0, 1, 7 | 2-methyl-pyridin-4-yl | N,N-dimethylpropanamide | 3-CN, 4-F |
| 187 | 0, 1, 7 | 2-methyl-pyridin-4-yl | N,N-dimethylpropanamide | 3-OCH$_3$, 4-F |
| 188 | 0, 1, 7 | 2-methyl-pyridin-4-yl | N,N-dimethylpropanamide | 3-OCH$_3$, 4-F, 5-F |
| 189 | 0, 1, 5 | 6-(methylamino)pyridin-3-yl | N,N-dimethylpropanamide | 2-F, 4-F, 5-F |
| 190 | 0, 1, 5 | 6-(ethylamino)pyridin-3-yl | N,N-dimethylpropanamide | 2-F, 4-F, 5-F |
| 191 | 0, 1 | 6-(trifluoromethyl)pyridin-3-yl | N,N-dimethylpropanamide | 3-F, 4-F |
| 192 | 0, 1 | 2-chloropyridin-4-yl | N,N-dimethylpropanamide | 3-CH$_3$, 4-F |
| 193 | 0, 1, 5 | 6-(cyclopropylamino)pyridin-3-yl | N,N-dimethylpropanamide | 2-F, 4-F, 5-F |

TABLE 3-continued

Compounds prepared according to the Examples.

| Co. nr. | Prep. | L | Z | R |
|---|---|---|---|---|
| 194 | 0, 1 | 2,3-dihydrobenzo[1,4]dioxin-6-yl | -CH2CH2-C(=O)-N(CH3)2 | 3-F |
| 195 | 0, 1 | 2,3-dihydrobenzo[1,4]dioxin-6-yl | -CH2CH2-C(=O)-N(CH3)2 | 3-Cl |
| 196 | 0, 1 | 2,3-dihydrobenzo[1,4]dioxin-6-yl | -CH2CH2-C(=O)-N(CH3)2 | 2-Cl, 5-OCH3 |
| 197 | 0, 1 | 2,3-dihydrobenzo[1,4]dioxin-6-yl | -CH2CH2-C(=O)-N(CH3)2 | 2-OCH3, 5-Cl |

TABLE 4

Compounds prepared according to the Examples.

| Co. nr. | Prep. | L | Z |
|---|---|---|---|
| 198 | 0, 1, 7 | 2-methylpyridin-4-yl | CH3-S-CH(OH)-CH2- |
| 199 | 0, 1, 5 | 2-(ethylamino)pyridin-4-yl | CH3-S-CH(OH)-CH2- |
| 200 | 0, 1, 2, 7 | 2-methylpyridin-4-yl | CH3-NH-C(=O)-CH2- |
| 201 | 0, 1, 2, 7 | 3-fluoro-2-methylpyridin-4-yl | CH3CH2-NH-C(=O)-CH2- |

TABLE 4-continued

Compounds prepared according to the Examples.

| Co. nr. | Prep. | L | Z |
|---|---|---|---|
| 202 | 0, 1, 2, 7 | 2-methyl-5-chloropyridin-4-yl | -CH2C(O)NHCH3 |
| 203 | 0, 1, 2 | 2,5-dichloropyridin-4-yl | -CH2C(O)NHCH3 |
| 46 | 0, 1, 2, 7 | 2-methylpyridin-4-yl | -CH2C(O)NHCH2CH3 |
| 204 | 28, 0, 1, 2 | 6,7-dihydro-5H-cyclopenta[b]pyridin-4-yl | -CH2C(O)NHCH2CH3 |
| 26 | 0, 1, 2 | 2-methylpyridin-4-yl | -CH2C(O)NHCH2-cyclopropyl |
| 205 | 0, 1, 2 | 2-methylpyridin-4-yl | -CH2C(O)NH-cyclobutyl |
| 206 | 0, 1, 2 | 2-methylpyridin-4-yl | -CH2C(O)NH-cyclopentyl |
| 207 | 0, 1, 2 | 2-methylpyridin-4-yl | -CH2C(O)NH-(2-hydroxycyclopentyl) (RS,RS) |
| 208 | 0, 1, 2 | 2-methylpyridin-4-yl | -CH2C(O)NH-(tetrahydrofuran-3-yl) |
| 33 | 0, 1 | pyridin-4-yl | -CH2CH2C(O)N(CH3)2 |
| 45 | 0, 1, 7 | 2-methylpyridin-4-yl | -CH2CH2C(O)N(CH3)2 |
| 209 | 0, 1, 7 | 2,6-dimethylpyridin-4-yl | -CH2CH2C(O)N(CH3)2 |
| 210 | 0, 1 | 3-fluoropyridin-4-yl | -CH2CH2C(O)N(CH3)2 |

TABLE 5

Compounds prepared according to the Examples.

| Comp. nr. | Prep. | Structure |
|---|---|---|
| 211 | 0, 1 | (structure) |
| 212 | 0, 1 | (structure) |

C. Compound Identification

For LCMS-characterization of the compounds of the present invention, the following methods were used.

General Procedure A

The HPLC gradient was supplied by an Alliance HT 2790 (Waters) system comprising a quaternary pump with degasser, an autosampler, a column oven (set at 40° C.), a diode-array detector (DAD) and a column as specified in the respective methods below. Flow from the column was split to a MS detector. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The HPLC gradient was supplied by a Waters 1512 pump with a Waters diode-array detector (DAD) with Gilson 215 autosampler and a column as specified in the respective methods below. Flow from the column was split to a MS detector. Ionisation was either electrospray or APCI depending on type of compound. Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 µA and a cone voltage of 25 V. The source temperature was maintained at 140-160° C. (the exact temperature was determined on a compound-by-compound basis). The desolvation temperature was 350° C. Mass spectra were acquired by scanning from 100 to 650 or 1000 when required, for example in 1 second using a dwell time of 0.1 sec. Nitrogen was used as the nebulizer gas.

General Procedure C

The LC gradient was supplied by an Acquity HPLC (Waters) system comprising a binary pump, a sample organizer, a column heater (set at 55° C.), a diode-array detector (DAD) and a column as specified in the respective methods below. Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure D

The HPLC gradient was supplied by an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES. Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

C.1 LCMS—Procedure 1

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 µl was used. Cone voltage was 10 V for positive ionization mode and 20 V for negative ionization mode.

C.2 LCMS—Procedure 2

In addition to general procedure A: Reversed phase HPLC was carried out on an Xterra MS C18 column (3.5 µm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 µl was used.

Cone voltage was 10 V for positive ionization mode and 20 V for negative ionization mode.

C.3 LCMS—Procedure 3

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 µl was used. Cone voltage was 10 V for positive ionization mode and 20 V for negative ionization mode.

C.4 LCMS—Procedure 4

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

C.5 LCMS—Procedure 5

In addition to general procedure B: Reversed phase HPLC was carried out on a Waters Xterra MS 5µ C18 column (4.6×100 mm; plus guard cartridge) with a flow rate of 2 ml/min. Two mobile phases (mobile phase A: water with 10 mM ammonium bicarbonate; mobile phase B: acetonitrile) were employed to run a gradient condition from 95% A to 95% B with a flow rate of 2 ml/min in 3.5 minutes and hold for 2 minutes. Typically, injection volumes of between 2 µl and 7 µl, inclusive were used.

C.6 LCMS—Procedure 6

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

C.7 LCMS—Procedure 7

In addition to general procedure A: Reversed phase HPLC was carried out on an Xbridge C18 column (3.5 µm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 µl was used. Cone voltage was 10 V for positive ionization mode and 20 V for negative ionization mode.

C.8 LCMS—Procedure 8

In addition to general procedure C: Reversed phase HPLC was carried out on a bridged ethylsiloxane/silica (BEH) C18 column (1.7 µm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A to 5% A, 95% B in 1.3 minutes and hold for 0.2 minutes. An injection volume of 0.5 µl was used. Cone voltage was 10 V for positive ionization mode and 20 V for negative ionization mode.

C.9 LCMS—Procedure 9

In addition to general procedure D: Reversed phase HPLC was carried out on a YMC ODS-AQ S-5 µm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 90% A and 10% B to 100% B in 3.4 minutes and hold for 0.1 minutes. Typical injection volumes of 2 µl were used. Column temperature was 50° C.

C.10 LCMS—Procedure 10

In addition to general procedure D: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

C.11 LCMS—Procedure 11

In addition to general procedure D: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

Melting Points

Melting points were determined with a DSC823e (Mettler-Toledo), a Buchi melting point apparatus or a WRS-2A digital melting point apparatus (Shanghai Precision and Scientific Instrument Co. Ltd). Values are either peak values or melt ranges, and are obtained with experimental uncertainties that are commonly associated with this analytical method.

Optical Rotation

The optical rotation was measured using a polarimeter. $[\alpha]_D^{20}$ indicates the optical rotation measured with light at the wavelength of the D-line of sodium (589 nm) at a temperature of 20° C. MeOH was used as the solvent. The cell pathlength is 1 dm. Behind the actual value the concentration of the solution which was used to measure the optical rotation is mentioned.

TABLE 6a

LCMS data - $(MH)^+$ and melting points

| Comp. Nr. | $R_t$ | $(MH)^+$ | Procedure | Melting point (° C.) |
|---|---|---|---|---|
| 18 | 2.35 | 319 | 5 | 193.0-194.0° C. |
| 64 | 1.04 | 359 | 1 | 155.9-157.1° C. |
| 82 | 0.99 | 478 | 1 | 166.3-168.3° C. |
| 87 | 5.08 | 368 | 4 | 171.1° C. |
| 73 | 5.67 | 380 | 4 | 165.4° C. |
| 183 | 4.27 | 367 | 4 | 150.3° C. |

TABLE 6a-continued

LCMS data - (MH)+ and melting points

| Comp. Nr. | $R_t$ | (MH)+ | Procedure | Melting point (° C.) |
|---|---|---|---|---|
| 168 | 5.52 | 421 | 4 | 178.4° C. |
| 182 | 4.42 | 362 | 4 | 194.3° C. |
| 33 | 5.27 | 417 | 4 | 216.4° C. |
| 81 | 5.73 | 435 | 6 | 149.2° C. |
| 75 | 5.69 | 393 | 4 | 164.2° C. |
| 74 | 6.20 | 408 | 4 | 159.0° C. |
| 38 | 5.63 | 435 | 4 | 167.4° C. |
| 48 | 5.54 | 419 | 4 | 169.1° C. |
| 136 | 5.55 | 437 | 4 | 217.7° C. |
| 194 | 2.66 | 412 | 9 | 114.3-116.30° C. |
| 72 | 5.63 | 380 | 4 | 160.0° C. |
| 77 | 5.57 | 435 | 4 | 145.6° C. |
| 70 | 5.61 | 378 | 4 | 167.9° C. |
| 80 | 5.72 | 400 | 4 | 182.0° C. |
| 195 | 2.83 | 428 | 9 | n.d. |
| 90 | 5.75 | 398 | 4 | 177.1° C. |
| 78 | 5.35 | 392 | 4 | 173.1° C. |
| 79 | 5.42 | 390 | 4 | 158.8° C. |
| 112 | 5.20 | 424 | 4 | 259.6° C. |
| 211 | 3.28 | 488 | 9 | n.d. |
| 197 | 3.01 | 458 | 9 | n.d. |
| 71 | 5.86 | 392 | 4 | 177.1° C. |
| 76 | 5.78 | 390 | 4 | 152.9° C. |
| 84 | 6.34 | 469 | 4 | 177.7° C. |
| 196 | 3.04 | 458 | 9 | 134.7-136.7° C. |
| 94 | 5.85 | 408 | 4 | 168.0° C. |
| 171 | 5.07 | 340 | 4 | 169.8° C. |
| 127 | 7.40 | 437 | 7 | 185.4° C. |
| 128 | 5.84 | 451 | 4 | 177.2° C. |
| 129 | 6.08 | 465 | 4 | 176.3° C. |
| 192 | 5.54 | 403 | 4 | 149.0° C. |
| 143 | 4.93 | 380 | 4 | 240.4° C. |
| 185 | 5.12 | 387 | 4 | 181.3° C. |
| 83 | 6.10 | 449 | 4 | 187.2° C. |
| 187 | 4.76 | 399 | 4 | 137.3° C. |
| 138 | 5.13 | 409 | 4 | 174.3° C. |
| 125 | 5.44 | 423 | 4 | 190.0° C. |
| 184 | 5.00 | 383 | 4 | 158.8° C. |
| 186 | n.d. | n.d. | — | 203.9° C. |
| 139 | n.d. | n.d. | — | 160.5° C. |
| 135 | 4.70 | 494 | 10 | 113.1-115.1° C. |
| 175 | 5.68 | 372 | 4 | 131.4° C. |
| 27 | 5.35 | 437 | 4 | 171.2° C. |
| 132 | 5.99 | 463 | 4 | 177.3° C. |
| 111 | 5.05 | 439 | 6 | 236.2° C. |
| 100 | 5.36 | 422 | 6 | 204.6° C. |
| 150 | 6.11 | 420 | 4 | 125.5° C. |
| 107 | 5.21 | 409 | 4 | 265.0° C. |
| 146 | 6.66 | 436 | 2 | 241.1° C. |
| 152 | 6.32 | 408 | 4 | n.d. |
| 178 | 4.77 | 374 | 4 | 247.0° C. |
| 177 | 6.05 | 360 | 4 | 150.3° C. |
| 110 | 5.48 | 425 | 4 | 255.1° C. |
| 130 | 6.64 | 466 | 7 | 201.1° C. |
| 151 | 6.11 | 420 | 4 | 207.5° C. |
| 44 | 6.03 | 422 | 4 | 165.8° C. |
| 106 | 5.75 | 422 | 4 | n.d. |
| 93 | 6.91 | 441 | 2 | n.d. |
| 96 | 0.99 | 410 | 1 | 126.5° C. |
| 92 | 5.35 | 397 | 4 | 179.0° C. |
| 98 | 5.63 | 411 | 4 | 164.5° C. |
| 131 | 4.94 | 496 | 6 | 167.7° C. |
| 31 | 7.42 | 430 | 7 | 180.7° C. |
| 29 | 8.46 | 477 | 7 | 156.1° C. |
| 105 | 5.67 | 424 | 4 | 174.4° C. |
| 30 | 7.22 | 481 | 7 | 151.6° C. |
| 179 | 5.27 | 385 | 4 | 222.4° C. |
| 115 | 4.53 | 468 | 6 | 207.1° C. |
| 47 | 5.71 | 390 | 4 | 138.1° C. |
| 55 | 4.63 | 444 | 6 | 166.8° C. |
| 95 | 4.88 | 423 | 6 | n.d. |
| 133 | 5.07 | 478 | 6 | 150.9° C. |
| 148 | 5.72 | 394 | 4 | 130.9° C. |
| 156 | n.d. | n.d. | — | 185.8-191.3° C. |
| 53 | 6.50 | 452 | 7 | 190.2° C. |
| 121 | 5.60 | 451 | 4 | 242.4° C. |
| 117 | 5.34 | 429 | 4 | 199.2° C. |
| 69 | 5.12 | 434 | 6 | n.d. |
| 198 | 5.65 | 390 | 4 | n.d. |
| 200 | 5.15 | 403 | 4 | 227.0° C. |
| 46 | 6.77 | 417 | 7 | 244.9° C. |
| 60 | 0.99 | 452 | 8 | n.d. |
| 59 | 1.32 | 548 | 8 | 182.4° C. |
| 140 | 6.14 | 479 | 4 | 147.2° C. |
| 28 | 5.21 | 437 | 4 | 246.8° C. |
| 149 | 5.98 | 423 | 4 | n.d. |
| 39 | 6.68 | 393 | 7 | 165.1° C. |
| 36 | 4.60 | 392 | 6 | 277.5° C. |
| 56 | 7.88 | 468 | 7 | 117.4° C. |
| 37 | 5.78 | 463 | 4 | 188.7° C. |
| 40 | 5.14 | 390 | 4 | n.d. |
| 174 | 6.93 | 429 | 7 | 181.7° C. |
| 35 | 0.75 | 403 | 1 | 221.6° C. |
| 190 | 5.99 | 434 | 7 | 134.2° C. |
| 120 | 5.36 | 435 | 4 | 251.0° C. |
| 58 | 6.20 | 464 | 7 | n.d. |
| 141 | 5.67 | 434 | 4 | 140.3° C. |
| 191 | 7.30 | 441 | 7 | 194.4° C. |
| 99 | 6.29 | 425 | 7 | n.d. |
| 193 | 5.94 | 446 | 7 | 158.2° C. |
| 103 | 6.42 | 437 | 7 | 176.5° C. |
| 104 | 6.74 | 451 | 7 | 145.8° C. |
| 126 | 5.45 | 437 | 4 | 171.5° C. |
| 49 | 6.87 | 390 | 7 | n.d. |
| 50 | 7.09 | 374 | 7 | 147.8° C. |
| 134 | 6.42 | 478 | 7 | 219.8° C. |
| 158 | 5.37 | 464 | 6 | 188.7° C. |
| 45 | 7.71 | 431 | 7 | 219.3° C. |
| 189 | 5.76 | 420 | 7 | 166.7° C. |
| 145 | 5.00 | 469 | 6 | 211.2° C. |
| 157 | 7.67 | 463 | 7 | 222.4° C. |
| 165 | 7.83 | 489 | 7 | 168.0° C. |
| 160 | 8.02 | 491 | 7 | 153.3° C. |
| 159 | 4.60 | 480 | 10 | 182.5-186.1° C. |
| 188 | 6.64 | 417 | 7 | 199.8° C. |
| 210 | n.d. | n.d. | — | 201.5° C. |
| 203 | n.d. | n.d. | — | 231.3° C. |
| 202 | 5.28 | 437 | 4 | 243.0° C. |
| 61 | 6.80 | 451 | 7 | 242.2° C. |
| 68 | 8.00 | 471 | 7 | 168.8° C. |
| 162 | 4.58 | 448 | 10 | 196.5-206.2° C. |
| 163 | 4.51 | 478 | 10 | 192.7-195.3° C. |
| 119 | 4.73 | 482 | 10 | 215.0-219.2° C. |
| 42 | n.d. | n.d. | — | 146.9° C. |
| 43 | n.d. | n.d. | — | 124.1° C. |
| 201 | 5.36 | 435 | 4 | 223.5° C. |
| 142 | 9.14 | 604 | 7 | n.d. |
| 205 | 5.54 | 443 | 4 | 224.8° C. |
| 206 | 5.73 | 457 | 4 | 229.1° C. |
| 207 | 5.08 | 473 | 4 | 219.7° C. |
| 26 | 5.51 | 443 | 4 | 227.2° C. |
| 167 | 1.01 | 453 | 1 | 157.1° C. |
| 172 | 8.35 | 398 | 7 | 200.0° C. |
| 209 | 5.55 | 445 | 4 | 182.2° C. |
| 204 | 5.14 | 443 | 6 | 260.1° C. |
| 118 | 5.17 | 423 | 4 | 238.6° C. |
| 62 | 7.67 | 465 | 7 | 204.6° C. |
| 212 | 4.90 | 435 | 11 | 214.2-223.5° C. |
| 176 | 6.64 | 429 | 7 | n.d. | n.d. = not determined

TABLE 6b

LCMS data - (MH)⁻ and melting points

| Comp. Nr. | $R_t$ | (MH)⁻ | Procedure | Melting point (° C.) |
|---|---|---|---|---|
| 17 | 0.97 | 347 | 1 | 140.5-142.0 |
| 14 | 0.96 | 348 | 1 | 163.4-165.2 |
| 15 | 0.86 | 374 | 1 | 207.2-207.9 |
| 13 | 1.07 | 442 | 1 | 179.9-182.1 |
| 16 | 0.93 | 348 | 1 | 158.2-159.0 |
| 20 | 1.03 | 428 | 1 | 203.6-206.4 |
| 2 | 0.93 | 348 | 1 | 179.1-180.0 |
| 19 | 0.94 | 361 | 1 | 271.0-272.1 |
| 9 | 0.98 | 375 | 1 | 212.9-214.0 |
| 3 | 9.69 | 405 | 2 | 188.3-190.3 |
| 11 | 0.83 | 389 | 1 | n.d. |
| 4 | 0.95 | 403 | 1 | 164.2-174.2 |
| 21 | 0.86 | 418 | 1 | 225.5 |
| 1 | 1.05 | 432 | 1 | 206.2-207.1 |
| 10 | 4.84 | 432 | 3 | 175.2-176.5 |
| 8 | 0.98 | 470 | 1 | 152.9-154.9 |
| 12 | 0.99 | 446 | 1 | n.d. |
| 5 | 1.02 | 460 | 1 | 213.9-215.0 |
| 6 | 1.03 | 460 | 1 | 195.7-196.6 |
| 22 | 0.97 | 417 | 1 | 196.5-197.2 |
| 23 | 1.00 | 446 | 1 | n.d. |
| 24 | 0.91 | 419 | 1 | 184.2-188.1 |
| 7 | 5.71 | 382 | 4 | n.d. |
| 52 | 5.16 | 362 | 6 | 147.2° C. |
| 85 | 5.10 | 429 | 6 | 182.2° C. |
| 86 | 4.75 | 445 | 6 | n.d. |
| 137 | 5.39 | 449 | 6 | n.d. |
| 88 | 5.70 | 394 | 4 | 183.0° C. |
| 170 | 4.67 | 342 | 6 | 162.2° C. |
| 169 | 4.68 | 340 | 6 | 135.1° C. |
| 91 | 0.95 | 410 | 1 | 157.9° C. |
| 144 | 4.87 | 447 | 6 | 177.2° C. |
| 54 | 6.00 | 508 | 4 | n.d. |
| 101 | 5.36 | 420 | 6 | n.d. |
| 89 | 5.40 | 384 | 4 | 149.4° C. |
| 114 | 4.56 | 422 | 6 | 260.8° C. |
| 113 | 4.49 | 422 | 6 | 256.6° C. |
| 147 | 4.12 | 494 | 6 | n.d. |
| 97 | 4.93 | 394 | 6 | 145.2° C. |
| 102 | 5.30 | 420 | 6 | n.d. |
| 108 | 4.47 | 407 | 6 | 247.1° C. |
| 155 | 4.92 | 431 | 6 | 217.0° C. |
| 124 | 4.98 | 447 | 6 | 172.3° C. |
| 153 | 4.58 | 420 | 6 | 208.6° C. |
| 154 | 4.51 | 409 | 6 | 192.2° C. |
| 116 | 4.44 | 411 | 6 | 249.5° C. |
| 109 | 4.42 | 423 | 6 | 234.8° C. |
| 199 | 5.28 | 417 | 6 | 167.9° C. |
| 180 | 5.07 | 418 | 6 | 259.6° C. |
| 41 | 4.69 | 387 | 6 | 186.1° C. |
| 181 | 0.88 | 443 | 1 | 192.8° C. |
| 164 | 5.06 | 431 | 6 | 190.7° C. |
| 173 | 5.22 | 403 | 6 | n.d. |
| 122 | 7.53 | 477 | 7 | 174.0° C. |
| 123 | 7.75 | 461 | 7 | 213.2° C. |
| 208 | 7.26 | 457 | 7 | 253.8° C. |
| 166 | 5.50 | 488 | 6 | 219.3° C. |
| 161 | 4.93 | 505 | 6 | n.d. | n.d. = not determined

TABLE 7

Optical Rotation data

| Comp. Nr. | $[\alpha]_D^{20}$ | concentration |
|---|---|---|
| 97 | +43.79° | C = 19.98 mg/5 ml |
| 98 | +42.38° | C = 17.46 mg/5 ml |
| 99 | +42.02° | C = 21.06 mg/5 ml |
| 100 | −29.43° | C = 18.18 mg/5 ml |
| 101 | +34.48° | C = 20.30 mg/5 ml |
| 102 | +40.41° | C = 20.29 mg/5 ml |
| 103 | +41.18° | C = 17.12 mg/5 ml |
| 104 | +39.08° | C = 18.68 mg/5 ml |
| 105 | +39.95° | C = 20.40 mg/5 ml |
| 149 | +62.53° | C = 18.47 mg/5 ml |
| 150 | +34.86° | C = 18.79 mg/5 ml |
| 151 | −17.40° | C = 20.98 mg/5 ml |
| 49 | +41.74° | C = 17.25 mg/5 ml |
| 39 | +51.73° | C = 22.81 mg/5 ml |
| 50 | +38.10° | C = 23.36 mg/5 m |
| 41 | +44.05° | C = 20.43 mg/5 ml |
| 172 | +46.06° | C = 22.58 mg/5 ml |
| 174 | +33.80° | C = 19.82 mg/5 ml |
| 175 | +49.60° | C = 20.06 mg/5 ml |
| 176 | +52.31° | C = 10.80 mg/5 ml |
| 198 | +40.73° | C = 20.87 mg/5 ml |
| 199 | +41.40° | C = 23.55 mg/5 ml |

5D. Pharmacological Examples

Example D.1a

Ca²⁺ Flux Imaging (FLIPR) (Protocol A)

Stable expression in mammalian cells in general and rat GH4C1 cells in particular, of cDNA clones encoding the human α7 wild-type sequence (hα7-wt nAChR) and in which the coding region is placed downstream of a promoter results in the appearance of functional α7 nAChRs on the surface of the mammalian cells. This technique has provided a powerful means of assessing the function of α7 wild-type protein. Given the fact that the cation permeability of the α7 nicotinic receptor preferentially favours calcium, fluorescent imaging of $Ca^{2+}$ flux through the hα7-wt nAChR stably expressed in the GH4C1 cell line was used as a first means of assaying modulator activity of the compounds of the present invention.

Materials a) Assay Buffer
   Hanks buffered saline solution (HBSS, Invitrogen, Belgium), supplemented with 10 mM HEPES (Invitrogen, Belgium), CaCl₂ to a final concentration of 5 mM, 0.1% Bovine serum albumin (Sigma-Aldrich NV, Belgium), 2.5 mM probenecid (Sigma-Aldrich NV, Belgium).

b) Calcium-Sensitive Dye—Fluo-4AM
   Fluo-4AM (Molecular Probes, USA) was dissolved in DMSO containing 10% Pluronic acid (Molecular Probes, USA) to give a stock solution which was aliquoted and stored at −20° C. until later use. On the day of the experiment Fluo-4AM stock was defrosted and diluted in DMEM/F12 (Invitrogen, Belgium) to give a final concentration of 4 μM.

c) 96-Well Plates
   BD Biocoat poly-D-lysine 96-well black/clear plates (BD Biosciences, Belgium)

d) Calcium Flux Measurement
   A Fluorimetric Imaging Plate Reader (FLIPR, Molecular Devices Corporation, Sunnyvale, USA) was used to measure intracellular free-calcium flux signals Method Monolayers of hα7-wt nAChR-expressing cells were grown in multi-well plates, in particular black-sided, transparent bottomed 96 well plates coated with poly-D-lysine for 24 hours prior to loading with a fluorescent calcium indicator, in a particular embodiment loading with fluo-3 or fluo-4AM for up to 90 minutes, in an even more particular embodiment loading with fluo-4AM for up to 90 minutes, and in a preferred embodiment loading with fluo-4AM for up to 60 minutes.

PAM activity was detected in real time by applying the compounds to be tested to the loaded cells along with a α7 nicotinic receptor agonist during constant monitoring of cellular fluorescence in a FLIPR. Compounds giving peak fluorescent responses greater than the response due to agonist alone, were considered to be α7 nAChR PAM's. In a particular embodiment, the α7 nicotinic receptor agonist was choline, a more particular embodiment choline applied at a submaximal concentration of 100 μM. In a further setting of the present invention the compounds to be tested were applied prior to the α7 nicotinic receptor agonist, in a particular embodiment up to 20 minutes prior to the agonist, a more particular embodiment up to 10 minutes prior to the agonist, and an even more particular embodiment 10 minutes prior to the agonist.

A control response to choline was calculated on each plate from the difference in peak in fluorescence in wells receiving either choline or assay buffer alone. Compounds of the present invention were tested at a concentration range from 0.1 μM to 50 μM. Compounds were considered to have an interesting activity when their efficacy was at least 500% when tested at the concentration where they have a maximal effect, typically between 0.1 μM and 50 μM (the efficacy of 100 μM choline was defined as 100% in the absence of a PAM). The compounds also have a potentiating effect on the response to choline when measured by whole-cell patch clamp electrophysiology in GH4C1 cells stably over-expressing the human wild-type α7 receptor.

Example D.1 b

Ca$^{2+}$ Flux Imaging (FDSS) (Protocol B)

Materials
a) Assay Buffer
   Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium).
b) Calcium-Sensitive Dye—Fluo-4AM
   Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 μM.
c) 384-Well Plates
   Black 384 well plate black/clear plates, PDL pre-coated (Corning, Incorporated, USA)
d) Calcium Flux Measurement
   A Functional drug screening system (FDSS, Hamamatsu) was used to measure intracellular free-calcium flux signals.
Method
   Monolayers of hα7-wt nAChR-expressing cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.

PAM activity was detected in real time by applying the compounds to be tested to the loaded cells along with a α7 nicotinic receptor agonist during constant monitoring of cellular fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a submaximal concentration of 100 μM. In a further setting of the present invention the compounds to be tested were applied prior to the α7 nicotinic receptor agonist, in a particular embodiment up to 10 minutes prior to the agonist.

A control response to choline was calculated on each plate from the difference in peak in fluorescence in wells receiving either choline or assay buffer alone. Compounds of the present invention were tested at a concentration range from 0.01 μM to 30 μM. Compounds were considered to have an interesting activity when they potentiated the choline signal at least with 500% when tested at a concentration of 30 μM (the efficacy of 100 μM choline was defined as 100% in the absence of a PAM). The compounds also have a potentiating effect on the response to choline when measured by whole-cell patch clamp electrophysiology in GH4C1 cells stably over-expressing the human wild-type α7 receptor.

Example D.2

Patch-Clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important an application system is used which is capable of very rapid switching of solutions (<100 ms) to prevent partial or full desensitisation of receptor responses coincident with the time of agonist application. Consequently, a second convenient technique to assess the enhancement of nicotinic efficacy is patch-clamp recording from hα7-wt nAChR-expressing GH4C1 cells coupled with a rapid-application system.
Materials
a) Assay Buffers
   The external recording solution consisted of 152 mM NaCl, 5 mM KCl, 1 mM MgCl$_2$, 1 mM Calcium, 10 mM HEPES; pH 7.3. The internal recording solution consisted of 140 mM CsCl, 10 mM HEPES, 10 mM EGTA, 1 mM MgCl$_2$, pH 7.3.
b) Patch-clamp recording was carried out using a Patch-clamp amplifier (Multiclamp 700A, Axon Instruments, CA, USA). hα7-wt nAChR-expressing GH4C1 cells were patch-clamp in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1 GΩ and series resistance <15 MΩ with at least 60% series resistance compensation. Membrane potential was clamped at −70 mV.
c) Agonists
   ACh, choline, were purchased from Sigma-Aldrich NV, Belgium.
d) Compound application
   A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 μl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist and even more particularly 5 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by compounds of the invention indicates that they are expected to have useful therapeutic activity. $EC_{50}$ values (potency), maximal effect (% efficacy), and Hill slopes were estimated by fitting the data to the logistic equation using GraphPad Prism (GraphPad Software, Inc., San Diego, Calif.).

An $EC_{50}$ (or $pEC_{50}$) was determined as a concentration relating to half the maximal effect, when a clear sigmoidal curve with top plateau was obtained. The $EC_{50}$ (or $pEC_{50}$) was defined as lower than maximal concentration in case the compound activity did not reach a top plateau at maximal concentration (indicated in table 8 as "<5")

TABLE 8

Potency ($pEC_{50}$) and % efficacy for a number of compounds.

| Comp. Nr. | $pEC_{50}$ | % efficacy | Protocol |
|---|---|---|---|
| 132 | 7.8 | 2764 | B |
| 134 | 7.7 | 2556 | B |
| 129 | 7.4 | 3216 | B |
| 128 | 7.3 | 3494 | B |
| 195 | 7.1 | 2918 | B |
| 162 | 7.1 | 1703 | B |
| 133 | 7.0 | 1846 | B |
| 142 | 7.0 | 3308 | B |
| 130 | 7.0 | 3607 | B |
| 160 | 6.9 | 2343 | B |
| 110 | 6.9 | 1606 | B |
| 197 | 6.9 | 2583 | B |
| 59 | 6.8 | 669 | B |
| 165 | 6.8 | 3241 | B |
| 58 | 6.8 | 2777 | B |
| 180 | 6.8 | 2542 | B |
| 6 | 6.8 | 9502 | A |
| 158 | 6.8 | 2601 | B |
| 5 | 6.7 | 2106 | B |
| 82 | 6.7 | 2100 | B |
| 83 | 6.7 | 3386 | B |
| 144 | 6.7 | 2404 | B |
| 127 | 6.7 | 4738 | B |
| 145 | 6.7 | 1145 | B |
| 166 | 6.7 | 2102 | B |
| 94 | 6.6 | 3569 | B |
| 1 | 6.6 | 2789 | B |
| 111 | 6.6 | 4120 | B |
| 84 | 6.5 | 4326 | B |
| 155 | 6.5 | 4060 | B |
| 194 | 6.5 | 2154 | B |
| 210 | 6.5 | 3926 | B |
| 85 | 6.5 | 6909 | B |
| 62 | 6.5 | 2706 | B |
| 190 | 6.4 | 3850 | B |
| 156 | 6.4 | 1895 | B |
| 131 | 6.4 | 1352 | B |
| 186 | 6.4 | 3840 | B |
| 167 | 6.4 | 3873 | B |
| 209 | 6.4 | 3711 | B |
| 157 | 6.4 | 1766 | B |
| 4 | 6.3 | 3403 | B |
| 168 | 6.3 | 2811 | B |
| 76 | 6.3 | 2045 | B |
| 173 | 6.3 | 2187 | B |
| 91 | 6.3 | 4081 | B |
| 192 | 6.2 | 3317 | B |
| 88 | 6.2 | 4496 | B |
| 140 | 6.2 | 2036 | B |
| 33 | 6.2 | 2652 | B |
| 125 | 6.2 | 3328 | B |
| 48 | 6.2 | 1814 | B |
| 206 | 6.2 | 2880 | B |
| 163 | 6.2 | 1512 | B |
| 204 | 6.2 | 3659 | B |
| 45 | 6.2 | 2903 | B |
| 114 | 6.2 | 4115 | B |
| 101 | 6.2 | 4517 | B |
| 181 | 6.1 | 2674 | B |
| 68 | 6.1 | 1494 | B |
| 71 | 6.1 | 601 | B |
| 28 | 6.1 | 2426 | B |
| 12 | 6.1 | 2298 | B |
| 184 | 6.1 | 2690 | B |
| 205 | 6.1 | 3716 | B |
| 26 | 6.1 | 3541 | B |
| 119 | 6.1 | 974 | B |
| 43 | 6.1 | 1350 | B |
| 189 | 6.1 | 1386 | B |
| 193 | 6.1 | 4792 | B |
| 103 | 6.1 | 5106 | B |
| 159 | 6.1 | 963 | B |
| 188 | 6.1 | 4381 | B |
| 112 | 6.1 | 2440 | B |
| 172 | 6.1 | 812 | B |
| 118 | 6.1 | 2806 | B |
| 149 | 6.0 | 704 | B |
| 54 | 6.0 | 735 | B |
| 146 | 6.0 | 2387 | B |
| 117 | 6.0 | 1906 | B |
| 39 | 6.0 | 1658 | B |
| 139 | 6.0 | 3274 | B |
| 185 | 6.0 | 2404 | B |
| 201 | 6.0 | 5088 | B |
| 42 | 6.0 | 1072 | B |
| 99 | 6.0 | 1500 | B |
| 107 | 6.0 | 2455 | B |
| 211 | 6.0 | 2017 | B |
| 212 | 5.9 | 6400 | B |
| 56 | 5.9 | 717 | B |
| 44 | 5.9 | 818 | B |
| 123 | 5.9 | 1808 | B |
| 116 | 5.9 | 3808 | B |
| 37 | 5.9 | 1126 | B |

TABLE 8-continued

Potency (pEC$_{50}$) and % efficacy for a number of compounds.

| Comp. Nr. | pEC$_{50}$ | % efficacy | Protocol |
|---|---|---|---|
| 21 | 5.9 | 3337 | B |
| 72 | 5.9 | 3557 | B |
| 74 | 5.9 | 2012 | B |
| 191 | 5.9 | 1900 | B |
| 126 | 5.9 | 3008 | B |
| 86 | 5.9 | 4906 | B |
| 161 | 5.8 | 550 | B |
| 137 | 5.8 | 2631 | B |
| 153 | 5.8 | 3750 | B |
| 151 | 5.7 | 1484 | B |
| 95 | 5.7 | 899 | B |
| 70 | 5.7 | 3135 | B |
| 102 | 5.7 | 1960 | B |
| 164 | 5.7 | 4309 | B |
| 69 | 5.7 | 1171 | B |
| 200 | 5.7 | 1359 | B |
| 46 | 5.7 | 4061 | B |
| 10 | 5.7 | 3083 | B |
| 13 | 5.7 | 3422 | A |
| 143 | 5.7 | 3472 | B |
| 122 | 5.7 | 988 | B |
| 113 | 5.7 | 4215 | B |
| 90 | 5.7 | 4519 | B |
| 36 | 5.6 | 2662 | B |
| 124 | 5.6 | 1289 | B |
| 96 | 5.6 | 1531 | B |
| 106 | 5.6 | 2382 | B |
| 77 | 5.6 | 1291 | B |
| 175 | 5.6 | 904 | A |
| 108 | 5.6 | 2025 | B |
| 121 | 5.6 | 1647 | B |
| 199 | 5.6 | 2315 | B |
| 141 | 5.6 | 2083 | B |
| 87 | 5.6 | 2950 | B |
| 75 | 5.6 | 2841 | B |
| 171 | 5.6 | 2085 | B |
| 8 | 5.6 | 4858 | B |
| 93 | 5.5 | 764 | B |
| 203 | 5.5 | 1222 | B |
| 169 | 5.5 | 762 | B |
| 80 | 5.5 | 1619 | A |
| 136 | 5.5 | 4342 | B |
| 196 | 5.5 | 5549 | A |
| 135 | 5.5 | 2942 | A |
| 179 | 5.5 | 1913 | B |
| 92 | 5.5 | 2062 | B |
| 154 | 5.5 | 2126 | B |
| 97 | 5.5 | 3158 | B |
| 73 | 5.5 | 3045 | B |
| 104 | 5.5 | 5655 | B |
| 202 | 5.5 | 4018 | B |
| 3 | 5.5 | 4866 | A |
| 60 | 5.4 | 772 | B |
| 187 | 5.4 | 3150 | B |
| 177 | 5.4 | 1938 | A |
| 100 | 5.4 | 1451 | A |
| 109 | 5.4 | 1869 | B |
| 105 | 5.4 | 1749 | B |
| 120 | 5.4 | 2343 | B |
| 38 | 5.4 | 1440 | A |
| 150 | 5.4 | 3651 | A |
| 152 | 5.4 | 4599 | A |
| 53 | 5.3 | 1390 | B |
| 208 | 5.3 | 909 | B |
| 14 | 5.3 | 1489 | B |
| 61 | 5.3 | 3528 | B |
| 89 | 5.3 | 2420 | B |
| 148 | 5.3 | 3230 | B |
| 50 | 5.2 | 650 | B |
| 7 | 5.2 | 1476 | A |
| 16 | 5.1 | 583 | B |
| 2 | 5.1 | 4206 | B |
| 52 | 5.1 | 641 | A |
| 183 | 5.0 | 1983 | B |
| 22 | 5.0 | 2078 | A |
| 20 | <5 | 1683 | A |
| 81 | <5 | 2290 | A |
| 178 | <5 | 6391 | A |
| 18 | <5 | 1183 | A |
| 41 | <5 | 635 | B |
| 174 | <5 | 667 | B |
| 35 | <5 | 1422 | B |
| 115 | <5 | 1709 | B |
| 147 | <5 | 864 | B |
| 47 | <5 | 2858 | B |
| 198 | <5 | 1087 | B |
| 207 | <5 | 811 | B |
| 138 | <5 | 1492 | B |
| 170 | <5 | 3793 | B |
| 27 | <5 | 1834 | A |
| 98 | <5 | 2904 | B |
| 182 | <5 | 3396 | A |
| 23 | <5 | 1080 | A |
| 24 | <5 | 3829 | B |
| 78 | <5 | 1923 | A |
| 79 | <5 | 2549 | A |
| 11 | <5 | 938 | A |
| 19 | <5 | 4746 | B |
| 9 | <5 | 8016 | B |

The invention claimed is:
1. A compound according to formula (I)

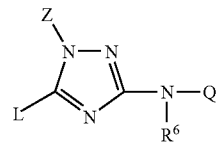

including all stereochemically isomeric forms thereof, wherein

Z is $C_{1-6}$alkyl substituted with one or more substituents independently selected from the group consisting of hydroxy, cyano, $C_{1-6}$alkyl-O—, $R^1R^2N$—C(=O)—, $R^7$—O—C(=O)—$NR^8$—, $R^{10}$—O—C(=O)—, $R^3$—C(=O)—$NR^4$, HO—N—C(=NH)—, oxo, polyhalo$C_{1-6}$alkyl and Het;

Q is phenyl, pyridinyl, indolinyl, benzodioxolyl, 1,4-benzodioxanyl, benzofuranyl, 2,3-dihydrobenzofuranyl, isoxazolyl, oxazolyl, thiazolyl, isothiazolyl, pyrimidinyl, or pyridazinyl, wherein each radical is optionally substituted with one, two or three substituents each independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, Het, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{11}$— and $R^{12}R^{13}N$—C(=O)—;

L is $C_{1-6}$alkyl optionally substituted with one or where possible two or more substituents each independently selected from the group consisting of halo, $C_{1-6}$alkyl-O—, $C_{1-6}$alkylthio, $C_{1-6}$alkyl-O—C(=O)—, polyhalo$C_{1-6}$alkyl and polyhalo$C_{1-6}$alkyl-O—; or is $C_{3-6}$cycloalkyl, phenyl, pyrimidinyl, pyridinyl, pyrimidazolyl, pyridazinyl, tetrahydropyranyl, imidazothiazolyl, benzodioxolyl, indolinyl, isoindolinyl, benzofuranyl, quinolinyl, isoquinolinyl, benzoxazolyl, 5,6,7,8,-tetrahydroquinolinyl, 5,6,7,8,-tetrahydroisoquinolinyl, 2,3-dihydropyrrolopyridinyl, furopyridinyl, 2,3-dihydrobenzofuranyl, benzodioxanyl, dihydrofuropyridinyl, 7-azaindolinyl, and 3,4-dihydro-2H-1,4-benzoxazinyl; wherein each of the aforementioned radicals is optionally substituted with one or two or more substituents, each substituent being independently selected from the group consisting of halo, hydroxyl, cyano, $C_{1-6}$alkyl, $C_{1-6}$alkyl-O—, $C_{1-6}$alkylthio, $C_{1-6}$alkyl-O—C(=O)—, HO—C(=O)—$C_{1-6}$alkyl-, $Het^1$, polyhalo$C_{1-6}$alkyl, HO—$C_{1-6}$alkyl-, polyhalo$C_{1-6}$alkyl-O—, amino, amino-$C_{1-6}$alkyl-, $C_{1-6}$alkyl-S(=O)$_2$—, mono- or di($C_{1-6}$alkyl)amino, formylamino, $C_{1-6}$alkyl-C(=O)—$NR^{14}$—, $R^{15}R^{16}N$—C(=O)—, morpholinyl, $CH_3O$—$C_{1-6}$alkylNH—, HO—$C_{1-6}$alkyl-NH—, benzyloxy, $C_{3-6}$cycloalkyl, $C_{3-6}$cycloalkyl-NH—, $C_{3-6}$cycloalkyl-$C_{1-6}$alkyl-NH—, polyhalo$C_{1-6}$alkyl-C(=O)—$NR^{14}$—, $C_{1-6}$alkyl-C(=O)—, and $C_{1-6}$alkyl-O—$C_{1-6}$alkyl-;

$R^1$ and $R^2$ each independently represent hydrogen, $C_{1-6}$alkyl, $C_{3-6}$cycloalkyl, $C_{1-4}$alkyl-O—$C_{1-6}$alkyl, $Het^2$, HO—$C_{1-6}$alkyl, polyhalo$C_{1-6}$alkyl, $C_{3-6}$cycloalkyl substituted with $C_{1-4}$alkyl, $C_{3-6}$cycloalkyl$C_{1-6}$alkyl, dimethylamino-$C_{1-4}$alkyl or 2-hydroxycyclopentan-1-yl;

or $R^1$ and $R^2$ taken together with the nitrogen atom to which they are attached form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano and $C_{1-6}$alkyl;

$R^3$ represents hydrogen, $C_{1-6}$alkyl, $C_{3-6}$cycloalkyl, $Het^3$ or $C_{1-6}$alkyl substituted with one or more substituents selected from the group consisting of hydroxy, cyano, $C_{1-4}$alkyl-O— and $Het^4$;

$R^4$ and $R^8$ each independently represent hydrogen, $C_{1-6}$alkyl, or $C_{3-6}$cycloalkyl; wherein each of these alkyl-radicals may be substituted with one or more substituents selected from the group consisting of hydroxy, cyano, and $C_{1-4}$alkyl-O—;

$R^6$ represents hydrogen, $C_{1-6}$alkyl, or where Q represents phenyl, $R^6$ may also be a $C_{2-6}$alkanediyl attached to said phenyl ring to form together with the nitrogen to which it is attached and said phenyl ring a fused bicyclic ring system containing 9 to 10 ring atoms such as indolinyl or tetrahydroquinolinyl, each optionally substituted with trifluoromethyl;

$R^7$ and $R^{10}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano, $C_{1-4}$alkyl-O—, $Het^4$ and $NH_2$—C(CH$_3$)=N—;

$R^{11}$ and $R^{14}$ each independently represents hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—;

$R^{12}$ and $R^{13}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano or $C_{1-4}$alkyl-O—; or $R^{12}$ and $R^{13}$ taken together with the nitrogen atom to which they are attached may form a heterocyclic radical selected from the group consisting of pyrrolidinyl, piperidinyl, piperazinyl, morpholinyl, thiomorpholinyl and pyrazolidinyl; wherein said heterocyclic radical is optionally substituted with 1, 2 or 3 substituents each independently selected from the group consisting of halo, hydroxy, amino, cyano, $C_{1-6}$alkyl or polyhalo$C_{1-6}$alkyl;

$R^{15}$ and $R^{16}$ each independently represent hydrogen, $C_{1-6}$alkyl, or $C_{3-6}$cycloalkyl; wherein each of these alkyl-radicals may be substituted with one or more substituents selected from the group consisting of hydroxy, cyano and $C_{1-4}$alkyl-O—; or $R^{15}$ and $R^{16}$ taken together with the nitrogen atom to which they are attached may form a heterocyclic radical selected from the group consisting of pyrrolidinyl, piperidinyl, piperazinyl, morpholinyl, thiomorpholinyl or pyrazolidinyl; wherein said heterocyclic radical is optionally substituted with 1, 2 or 3 substituents each independently selected from the group consisting of halo, hydroxy, amino, cyano, $C_{1-6}$alkyl and polyhalo$C_{1-6}$alkyl;

Het and $Het^1$ each independently represent piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^2$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl, pyrazolyl or tetrahydrofuranyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^3$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano, $C_{1-6}$alkyl and polyhalo$C_{1-6}$alkyl;

$Het^4$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl; wherein each radical is optionally substituted with 1, 2 or 3 substituents, each substituent being independently selected from the group consisting of halo, hydroxy, amino, cyano or $C_{1-6}$alkyl;

an N-oxide, a pharmaceutically acceptable addition salt, or a quaternary amine thereof;

provided that said compound is not N-(2-methoxyphenyl)-1-methyl-5-(2,4-dichlorophenyl)-1H-1,2,4-triazol-3-amine.

2. The compound of claim 1, including all stereochemically isomeric forms thereof, wherein Z is $C_{1-6}$alkyl substituted with one or more substituents independently selected from the group consisting of hydroxy, cyano, $C_{1-6}$alkyl-O—, $R^1R^2N$—C(=O)—, $R^7$—O—C(=O)—$NR^8$—, $R^{10}$—O—C(=O)—, $R^3$—C(=O)—$NR^4$—, HO—N═C(—NH)—, oxo, polyhalo$C_{1-6}$alkyl and Het;

Q is phenyl, pyridinyl, benzodioxolyl, wherein each radical is optionally substituted with one, two or three substituents each independently selected from the group consisting of halo, cyano, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino;

L is phenyl, pyridinyl, benzodioxolyl, indolinyl, quinolinyl, 2,3-dihydropyrrolopyridinyl, furopyridinyl, benzodioxanyl, dihydrofuropyridinyl, 7-azaindolinyl, 3,4-dihydro-2H-1,4-benzoxazinyl; wherein each radical is optionally substituted with one or two or more substituents, each substituent being independently selected from the group consisting of halo, cyano, $C_{1-6}$alkyl, $C_{1-6}$alkyl-O—, polyhalo$C_{1-6}$alkyl, HO—$C_{1-6}$alkyl-, polyhalo$C_{1-6}$alkyl-O—, amino-$C_{1-6}$alkyl-, mono- or di($C_{1-6}$alkyl)amino, $R^{15}R^{16}N$—C(=O)—, morpholinyl, $CH_3O$—$C_{1-6}$alkyl-NH—, HO—$C_{1-6}$alkyl-NH—, benzyloxy, $C_{3-6}$cycloalkyl, $C_{3-6}$cycloalkyl-NH—, $C_{3-6}$cycloalkyl-$C_{1-6}$alkyl-NH—, polyhalo$C_{1-6}$alkyl-C(=O)—$NR^{14}$—, $C_{1-6}$alkyl-C(=O)—, and $C_{1-6}$alkyl-O—$C_{1-6}$alkyl-;

$R^1$ and $R^2$ each independently represent hydrogen, $C_{1-6}$alkyl, $C_{3-6}$cycloalkyl, $C_{1-4}$alkyl-O—$C_{1-6}$alkyl, $Het^2$, HO—$C_{1-6}$alkyl, polyhalo$C_{1-6}$alkyl, $C_{3-6}$cycloalkyl substituted with $C_{1-4}$alkyl, $C_{3-6}$cycloalkyl$C_{1-6}$alkyl, dimethylamino-$C_{1-4}$alkyl or 2-hydroxy-cyclopentan-1-yl;

or $R^1$ and $R^2$ taken together with the nitrogen atom to which they are attached form a heterocyclic radical selected from the group consisting of pyrrolidinyl, and morpholinyl;

$R^3$ represents hydrogen, $C_{1-6}$alkyl, $C_{3-6}$cycloalkyl, or $Het^3$;

$R^4$ and $R^8$ each independently represent hydrogen or $C_{1-6}$alkyl;

$R^6$ represents hydrogen, or where Q represents phenyl, $R^6$ may also be a $C_{2-6}$alkanediyl attached to said phenyl ring to form together with the nitrogen to which it is attached and said phenyl ring indolinyl substituted with trifluoromethyl;

$R^7$ and $R^{10}$ each independently represent $C_{1-6}$alkyl or $C_{3-6}$cycloalkyl;

$R^{11}$ and $R^{14}$ each independently represents hydrogen or $C_{1-6}$alkyl;

$R^{15}$ and $R^{16}$ each independently represent hydrogen or $C_{1-6}$alkyl; or $R^{15}$ and $R^{16}$ taken together with the nitrogen atom to which they are attached may form pyrrolidinyl;

Het and $Het^1$ each independently represent oxazolyl optionally substituted with $C_{1-6}$alkyl;

$Het^2$ represents tetrahydrofuranyl;

$Het^3$ represents oxazolyl;

an N-oxide, a pharmaceutically acceptable addition salt, or a quaternary amine thereof.

3. The compound of claim 1, including all stereochemically isomeric forms thereof, wherein Z is $C_{1-6}$alkyl substituted with hydroxy, $R^1R^2N$—C(=O)—, $R^3$—C(=O)—$NR^4$—;

Q is phenyl, pyridinyl, or benzodioxolyl; wherein each radical is optionally substituted with one, two or three substituents each independently selected from the group consisting of halo, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino;

L is phenyl, pyridinyl, benzodioxolyl, indolinyl, 2,3-dihydropyrrolopyridinyl, furopyridinyl, benzodioxanyl, dihydrofuropyridinyl, 7-azaindolinyl, or 3,4-dihydro-2H-1,4-benzoxazinyl; wherein each radical is optionally substituted with one or two or more substituents, each substituent being independently selected from the group consisting of halo, $C_{1-6}$alkyl, $C_{1-6}$alkyl-O—, HO—$C_{1-6}$alkyl-, mono- or di($C_{1-6}$alkyl)amino, $C_{3-6}$cycloalkyl, $C_{3-6}$cycloalkyl-NH—, $C_{3-6}$cycloalkyl-$C_{1-6}$alkyl-NH—, and $C_{1-6}$alkyl-O—$C_{1-6}$alkyl-;

$R^1$ and $R^2$ each independently represent hydrogen, $C_{1-6}$alkyl, or $C_{3-6}$cycloalkyl;

$R^3$ represents $C_{1-6}$alkyl;

$R^4$ represents hydrogen or $C_{1-6}$alkyl;

$R^6$ represents hydrogen;

an N-oxide, a pharmaceutically acceptable addition salt, or a quaternary amine thereof.

4. The compound of claim 1, including all stereochemically isomeric forms thereof, wherein Z is hydroxy$C_{2-3}$alkyl, or $R^1R^2N$—C(=O)—$C_{1-3}$alkyl;

Q is phenyl, or pyridinyl; wherein each radical is optionally substituted with one, two or three substituents each independently selected from the group consisting of halo, $C_{1-6}$alkyl, $C_{1-6}$alkyl-O—, polyhalo$C_{1-6}$alkyl, polyhalo$C_{1-6}$alkyl-O—, and mono- or di($C_{1-6}$alkyl)amino, or 2,2-difluoro-1,3-benzodioxol-5-yl;

L is phenyl, pyridinyl, indolinyl, 2,3-dihydropyrrolopyridinyl, benzodioxanyl, dihydrofuropyridinyl, 7-azaindolinyl, or 3,4-dihydro-2H-1,4-benzoxazinyl; wherein each radical is optionally substituted with one or two or more substituents, each substituent being independently selected from the group consisting of fluoro, chloro, $C_{1-2}$alkyl, $C_{1-2}$alkyl-O—, mono- or di($C_{1-2}$alkyl)amino, cyclopropyl, cyclopropyl-NH—, cyclopropylmethyl-NH—, and methyl-O-methyl-;

$R^1$ and $R^2$ each independently represent hydrogen, $C_{1-2}$alkyl, or $C_{3-5}$cycloalkyl;

$R^6$ represents hydrogen;

an N-oxide, a pharmaceutically acceptable addition salt, or a quaternary amine thereof.

5. The compound of claim 1 wherein Z is selected from the group consisting of hydroxyethyl; 2-hydroxypropyl; isopropylmethyl-NH—C(=O)—;

methyl-NH—C(=O)-methyl; ethyl-NH—C(=O)-methyl; dimethylamino-C(=O)-ethyl-;

pyrrolidinyl-C(=O)-ethyl-; isopropylamino-C(=O)-methyl-; and isoxazolecarboxamide-propyl wherein said isoxazole ring is optionally substituted with methyl.

6. The compound of claim 1 wherein Q is 2,2-difluoro-1,3 benzodioxol5-yl.

7. The compound of claim 1 wherein L is a selected from the group consisting of phenyl, pyridinyl, or 1,4-benzodioxanyl; wherein said L is optionally substituted with one or more methyl or ethylamino substituents.

8. The compound of claim 1, including all stereochemically isomeric forms thereof, selected from the group consisting of (S)-5-[2-(ethylamino)-4-pyridinyl]-α-methyl-3-[(3,4,5-trifluorophenyl)amino]-1H-1,2,4-triazole-1-ethanol, 3-[(2,2-difluoro-1,3-benzodioxol-5-yl)amino]-N,N-dimethyl-5-(4-pyridinyl)-1H-1,2,4-triazole-1-propanamide, 3-[(2,2-difluoro-1,3-benzodioxol-5-yl)amino]-N-ethyl-5-(2-methyl-4-pyridinyl)-1H-1,2,4-triazole-1-acetamide, 3-[(2,2-difluoro-1,3-benzodioxol-5-yl)amino]-N,N-dimethyl-5-(2-methyl-4-pyridinyl)-1H-1,2,4-triazole-1-propanamide, N-(cyclopropylmethyl)-3-[(2,2-difluoro-1,3-benzo-dioxol-5-yl)amino]-5-(2-methyl-4-pyridinyl)-1H-1,2,4-triazole-1-acetamide,
5-(2,3-dihydro-1,4-benzodioxin-6-yl)-N-methyl-3-[[3-(trifluoromethyl)phenyl]-amino]-1H-1,2,4-triazole-1-acetamide,
5-(2,3-dihydro-1,4-benzodioxin-6-yl)-N-(1-methylethyl)-3-[[3-(trifluoromethyl)-phenyl]amino]-1H-1,2,4-triazole-1-acetamide,
5-(4-pyridinyl)-3-[[3-(trifluoromethyl)phenyl]amino]-1H-1,2,4-triazole-1-ethanol,
5-(2,3-dihydro-1,4-benzodioxin-6-yl)-3-[[3-(trifluoromethyl)phenyl]amino]-1H-1,2,4-triazole-1-ethanol,
5-(2-chloro-4-pyridinyl)-3-[[3-(trifluoromethyl)phenyl]amino]-1H-1,2,4-triazole-1-ethanol,
N,N-dimethyl-5-(4-pyridinyl)-3-[[3-(trifluoromethyl)phenyl]amino]-1H-1,2,4-triazole-1-propanamide,
5-(2,3-dihydro-1,4-benzodioxin-6-yl)-N,N-dimethyl-3-[[3-(trifluoromethyl)-phenyl]-amino]-1H-1,2,4-triazole-1-propanamide,
5-methyl-N-[3-[5-(4-pyridinyl)-3-[[3-(trifluoromethyl)phenyl]amino]-1H-1,2,4-triazol-1-yl]propyl]-3-isoxazolecarboxamide, an N-oxide, a pharmaceutically acceptable addition salt, or a quaternary amine thereof.

9. A pharmaceutical composition comprising a pharmaceutically acceptable carrier and as active ingredient a therapeutically effective amount of a compound selected from the group consisting of the compound of claim 1 and N-(2-methoxyphenyl)-1-methyl-5-(2,4-dichlorophenyl)-1H-1,2,4-triazol-3-amine.

10. A process of preparing a pharmaceutical composition comprising intimately mixing a pharmaceutically acceptable carrier is intimately mixed with a therapeutically effective amount of a compound selected from the group consisting of the compound of claim 1 and N-(2-methoxyphenyl)-1-methyl-5-(2,4-dichlorophenyl)-1H-1,2,4-triazol-3-amine.

11. A product comprising:
   (a) a compound of claim 1 or N-(2-methoxyphenyl)-1-methyl-5-(2,4-dichlorophenyl)-1H-1,2,4-triazol-3-amine, and
   (b) a α7 nicotinic receptor agonist.

* * * * *